US008859516B2

(12) United States Patent
Bumcrot et al.

(10) Patent No.: US 8,859,516 B2
(45) Date of Patent: Oct. 14, 2014

(54) LIPID FORMULATED COMPOSITIONS AND METHODS FOR INHIBITING EXPRESSION OF EG5 AND VEGF GENES

(75) Inventors: David Bumcrot, Belmont, MA (US); Dinah Wen-Yee Sah, Boston, MA (US); Ivanka Toudjarska, Medford, MA (US); Jared Gollob, Boston, MA (US); Akshay Vaishnaw, Arlington, MA (US); Christina Gamba-Vitalo, Cambridge, MA (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 13/496,196

(22) PCT Filed: Sep. 10, 2010

(86) PCT No.: PCT/US2010/048512
§ 371 (c)(1),
(2), (4) Date: Jul. 2, 2012

(87) PCT Pub. No.: WO2011/034798
PCT Pub. Date: Mar. 24, 2011

(65) Prior Publication Data
US 2012/0282341 A1 Nov. 8, 2012

Related U.S. Application Data

(60) Provisional application No. 61/242,693, filed on Sep. 15, 2009, provisional application No. 61/244,792, filed on Sep. 22, 2009, provisional application No. 61/255,692, filed on Oct. 28, 2009, provisional application No. 61/262,046, filed on Nov. 17, 2009, provisional application No. 61/326,071, filed on Apr. 20, 2010, provisional application No. 61/352,128, filed on Jun. 7, 2010.

(51) Int. Cl.
*A61K 48/00* (2006.01)
*C07H 21/02* (2006.01)
*C07H 21/04* (2006.01)

(52) U.S. Cl.
USPC .......................... 514/44; 536/23.1; 536/24.5

(58) Field of Classification Search
None
See application file for complete search history.

(56) References Cited

U.S. PATENT DOCUMENTS

| | | | |
|---|---|---|---|
| 7,427,605 B2 | 9/2008 | Davis et al. |
| 7,718,629 B2 | 5/2010 | Bumcrot et al. |
| 8,058,069 B2 | 11/2011 | Yaworski et al. |
| 8,158,601 B2 | 4/2012 | Chen et al. |
| 8,598,333 B2 | 12/2013 | Maclachlan et al. |
| 2003/0143732 A1 | 7/2003 | Fosnaugh et al. |
| 2003/0170891 A1 | 9/2003 | McSwiggen |
| 2004/0209832 A1 | 10/2004 | McSwiggen et al. |
| 2004/0259247 A1 | 12/2004 | Tuschl et al. |
| 2006/0063751 A1 | 3/2006 | Aquila et al. |
| 2006/0263435 A1 | 11/2006 | Davis et al. |
| 2007/0004664 A1 | 1/2007 | McSwiggen et al. |
| 2007/0031844 A1 | 2/2007 | Khvorova et al. |
| 2007/0135372 A1 | 6/2007 | MacLachlan et al. |
| 2007/0281899 A1 | 12/2007 | Bumcrot et al. |
| 2008/0213350 A1 | 9/2008 | Ko et al. |
| 2009/0099109 A1 | 4/2009 | Shames et al. |
| 2009/0149403 A1 | 6/2009 | MacLachlan |
| 2009/0291131 A1 | 11/2009 | MacLachlan et al. |
| 2010/0087508 A1 | 4/2010 | Bumcrot et al. |
| 2010/0267806 A1 | 10/2010 | Bumcrot et al. |
| 2011/0015250 A1 | 1/2011 | Bumcrot et al. |
| 2012/0136145 A1 | 5/2012 | Bumcrot et al. |
| 2012/0244207 A1 | 9/2012 | Fitzgerald et al. |
| 2013/0023577 A1 | 1/2013 | Bumcrot et al. |
| 2013/0274311 A1 | 10/2013 | Bumcrot et al. |

FOREIGN PATENT DOCUMENTS

| | | |
|---|---|---|
| WO | WO 03/070918 A2 | 8/2003 |
| WO | WO 2004/065601 | 8/2004 |
| WO | WO 2004/080406 | 9/2004 |
| WO | WO 2004/090108 | 10/2004 |
| WO | WO 2005/014782 A2 | 2/2005 |
| WO | WO 2005/089224 | 9/2005 |
| WO | WO 2007/012191 | 2/2007 |
| WO | WO 2007/115168 | 10/2007 |
| WO | WO 2009/111658 | 9/2009 |
| WO | WO 2010/105209 | 9/2010 |
| WO | WO 2010/147992 | 12/2010 |
| WO | WO 2011/017548 | 2/2011 |

OTHER PUBLICATIONS

Agrawal, S., et al., "Antisense oligonucleotides: towards clinical trials." Trends in Biotechnology. Oct. 1996, vol. 14, pp. 376-387.
Australian Government—IP Australia, Patent Examination Report No. 1, Australian Patent Application No. 2010235872, Jun. 21, 2012, 4 pages.
Bass, B., "The short answer," Nature, May 24, 2001, pp. 428-429, vol. 411.
Canadian Intellectual Property Office, Requisition by the Examiner for Canadian Patent Application No. 2,559,161, May 23, 2012, 3 pages.

(Continued)

Primary Examiner — Amy Bowman
(74) Attorney, Agent, or Firm — Fenwick & West LLP

(57) ABSTRACT

This invention relates to compositions containing double-stranded ribonucleic acid (dsRNA) in a SNALP formulation, methods of using the compositions to inhibit the expression of the Eg5/KSP and VEGF, and methods of using the compositions to treat pathological processes mediated by Eg5/KSP and VEGF expression, such as cancer.

20 Claims, 36 Drawing Sheets

(56) References Cited

OTHER PUBLICATIONS

Elbashir, S., et al., "Analysis of gene function in somatic mammalian cells using small interfering RNAs," Methods, 2002, pp. 199-213, vol. 26.
Elbashir, S., et al., "Duplexes of 21-nucleotide RNAs mediate RNA interference in mammalian cell culture," Nature, May 24, 2001, p. 494-498, vol. 411.
Elbashir, S., et al., "Functional Anatomy of siRNAs for Mediating Efficient RNAi in *Drosophila Melanogaster* Embryo Lysate", The EMBO Journal, 2001, pp. 6877-6888, vol. 20, No. 23.
Elbashir, S., et al., "RNA Interference is Mediated by 21-and 22 Nucleotide RNAs," Genes & Development, 2001, pp. 188-200, vol. 15.
Fire, A., "RNA-triggered Gene Silencing," Trends in Genetics, Sep. 1999, pp. 358-363, vol. 15, No. 9.
Fire, A., et al., "Potent and Specific Genetic Interference by Double Stranded RNA in *Caenorhabditis elegans*," Nature, Feb. 19, 1998, pp. 806-811, vol. 391.
Hungarian Intellectual Property Office, Written Opinion and Search Report for Singaporean Patent Application No. 201006379-0, Jul. 6, 2012, 15 pages.
Japanese Patent Office, Notice of Reasons for Rejection, Japanese Patent Application No. 2009-503309, mailed Aug. 10, 2012, 10 pages.
PCT International Search Report and Written Opinion, PCT/US2010/048512, Nov. 16, 2010, 15 pages.
Reynolds, et al. (2004) "Rational siRNA design for RNA interference," Nature Biotechnology, vol. 22, No. 3, pp. 326-330.
Robbins, M., et al., "Stable expression of shRNAs in human CD34+ progenitor cells can avoid induction of interferon responses to siRNAs in vitro," Nature Biotechnology, May 2006, pp. 566-571, vol. 24, No. 5.
Rose, S., et al., "Functional polarity is introduced by Dicer processing of short substrate RNAs," Nucleic Acids Research, 2005, pp. 4140-4156, vol. 33, No. 13.
Takimoto, C., et al., "Safety and anti-tumor activity of sorafenib (Nexavar ®) in combination with other anti-cancer agents: a review of clinical trials," Cancer Chemother Pharmacol, (2008) 61: pp. 535-548.
The State Intellectual Property Office of the People's Republic of China, Notification of the Third Office Action, Chinese Patent Application No. 200780018407.5, Aug. 31, 2012, 9 pages.
Tuschl T., "RNA Interference and Small Interfering RNAs" Chembiochem, 2001, pp. 239-245, vol. 2.
Tuschl, T., "Expanding small RNA interference," Nature Biotechnology, May 2002, pp. 446-448, vol. 20.
Tuschl, T., "Functional genomics: RNA sets the standard," Nature, Jan. 16, 2003, vol. 421, No. 6920, pp. 220-221.
Tuschl, T., "Mammalian RNA Interference," RNAi, a Guide to Gene Silencing, Chapter 13, G.J. Hannon (ed,), 2003, pp. 265-295.
Tuschl, T., et al., "Small Interfering RNAs: A Revolutionary Tool for the Analysis of Gene Function and Gene Therapy," Molecular Interventions, 2002, pp. 158-167, vol. 2, No. 3.
Tuschl, T., et al., "Targeted mRNA Degradation by Double-Stranded RNA in Vitro," Genes & Development, 1999, pp. 3191-3197, vol. 13.
Vickers, T., et al., "Efficient Reduction of Target RNAs by Small Interfering RNA and RNase H-dependent Antisense Agents, " The Journal of Biological Chemistry, Feb. 28, 2003, pp. 7108-7118, vol. 278, No. 9.
Weil, et al (2002) "Targeting the Kinesin Eg5 to Monitor siRNA Transfection in Mammalian Cells," *Biotechniques* 33(6):1244-1248.
Zimmerman, et al. (2006) "RNAi-mediated gene silencing in non-human primates," *Nature*, vol. 441, May 4:111-114.
Zhu, A., (2007) "Development of Sorafenib and Other Molecularly Targeted Agents in Hepatocellular Carcinoma," American Cancer Society, vol. 112(2): 250-259.
European Patent Office, Extended European Search Report, European Patent Application No. 12166396.7, Oct. 31, 2012, 8 Pages.
The State Intellectual Property Office of the People's Republic of China, Notification of the First Office Action, Chinese Patent Application No. 201080020483.1, Sep. 28, 2012, 14 Pages.
The State Intellectual Property Office of the People's Republic of China, Notification of the First Office Action, Chinese Patent Application No. 201080047889.9, Feb. 1, 2013, 10 Pages.
The State Intellectual Property Office of the People's Republic of China, Notification of Second Office Action, Chinese Patent Application No. 200980115656.5, Mar. 13, 2013, 13 Pages.
Harborth, J., et al., "Sequence, Chemical, and Structural Variation on Small Interfering RNAs and Short Hairpin RNAs and the Effect on Mammalian Gene Silencing," Antisense and Nucleic Acid Drug Development, vol. 13, pp. 83-105, 2003.
Harborth, J., et al., "Identification of essential genes in cultured mammalian cells using small interfering RNAs," Journal of Cell Science, 2001, vol. 114, No. 24, pp. 4557-4565.
Winstead, E., "Treatment for Advanced Liver Cancer Increases Survival," NCI Cancer Bulletin, Jun. 12, 2007, 2 pages, vol. 4, No. 19, can be retrieved at <URL:http://www.cancer.gov/ncicancerbulletin/archive/20071061207>.
Office Action for U.S. Appl. No. 13/442,809 mailed Oct. 16, 2013, 10 pages.
Office Action for U.S. Appl. No. 13/797,176 mailed Aug. 22, 2013, 12 pages.

A. SNALP-VSP treated   B. SNALP-Luc treated

SEQUENCE LISTING

```
<160> NUMBER OF SEQ ID NOS: 193

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1
ucgagaaucu aaacuaacut t                                           21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2
aguuaguuua gauucucgat t                                           21

<210> SEQ ID NO 3
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
gcacauagga gagaugagcu u                                           21

<210> SEQ ID NO 4
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
```

-continued

```
<400> SEQUENCE: 4
aagcucaucu cuccuaugug cug                                            23

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 5
ucgagaaucu aaacuaacut t                                              21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 6
aguuaguuua gauuccugat t                                              21

<210> SEQ ID NO 7
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
ucgagaaucu aaacuaacu                                                 19

<210> SEQ ID NO 8
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
gcacauagga gagaugagcu u                                              21

<210> SEQ ID NO 9
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
aagcucaucu cuccuaugug cug                                            23

<210> SEQ ID NO 10
<211> LENGTH: 21
<212> TYPE: RNA
```

<213> ORGANISM: Artificial Sequence
<220> FEATURE:
<223> OTHER INFORMATION: Description of Artificial Sequence: Synthetic oligonucleotide

<400> SEQUENCE: 10
gcacauagga gagaugagcu u                                              21

<210> SEQ ID NO 11
<211> LENGTH: 5101
<212> TYPE: DNA
<213> ORGANISM: Homo sapiens

<400> SEQUENCE: 11

| | | | | | |
|---|---|---|---|---|---|
| agcgcagcca | ttggtccggc | tactctgtct | cttttttcaaa | ttgaggcgcc | gagtcgttgc | 60 |
| ttagtttctg | gggattcggg | cggagacgag | attagtgatt | tggcggctcc | gactggcgcg | 120 |
| ggacaaacgc | cacggccaga | gtaccgggta | gagagcgggg | acgccgacct | gcgtgcgtcg | 180 |
| gtcctccagg | ccacgccagc | gcccgagagg | gaccagggag | actccggccc | ctgtcggccg | 240 |
| ccaagcccct | ccgcccctca | cagcgcccag | gtccgcggcc | gggccttgat | tttttggcgg | 300 |
| ggaccgtcat | ggcgtcgcag | ccaaattcgt | ctgcgaagaa | gaaagaggag | aaggggaaga | 360 |
| acatccaggt | ggtggtgaga | tgcagaccat | ttaatttggc | agagcggaaa | gctagcgccc | 420 |
| attcaatagt | agaatgtgat | cctgtacgaa | aagaagttag | tgtacgaact | ggaggattgg | 480 |
| ctgacaagag | ctcaaggaaa | acatacactt | tgatatggt | gtttggagca | tctactaaac | 540 |
| agattgatgt | ttaccgaagt | gttgtttgtc | caattctgga | tgaagttatt | atgggctata | 600 |
| attgcactat | ctttgcgtat | ggccaaactg | gcactggaaa | aacttttaca | atggaaggtg | 660 |
| aaaggtcacc | taatgaagag | tatacctggg | aagaggatcc | cttggctggt | ataattccac | 720 |
| gtacccttca | tcaaattttt | gagaaactta | ctgataatgg | tactgaatt | tcagtcaaag | 780 |
| tgtctctgtt | ggagatctat | aatgaagagc | ttttttgatct | tcttaatcca | tcatctgatg | 840 |
| tttctgagag | actacagatg | tttgatgatc | cccgtaacaa | gagaggagtg | ataattaaag | 900 |
| gtttagaaga | aattacagta | cacaacaagg | atgaagtcta | tcaaatttta | gaaaaggggg | 960 |
| cagcaaaaag | gacaactgca | gctactctga | tgaatgcata | ctctagtcgt | tcccactcag | 1020 |
| tttttctctgt | tacaatacat | atgaaagaaa | ctacgattga | tggagaagag | cttgttaaaa | 1080 |
| tcggaaagtt | gaacttggtt | gatcttgcag | gaagtgaaaa | cattggccgt | tctggagctg | 1140 |
| ttgataagag | agctcgggaa | gctggaaata | taaatcaatc | cctgttgact | ttgggaaggg | 1200 |
| tcattactgc | ccttgtagaa | agaacacctc | atgttcctta | tcgagaatct | aaactaacta | 1260 |
| gaatcctcca | ggattctctt | ggagggcgta | caagaacatc | tataattgca | caatttctc | 1320 |
| ctgcatctct | caatcttgag | gaaactctga | gtacattgga | atatgctcat | agagcaaaga | 1380 |
| acatattgaa | taagcctgaa | gtgaatcaga | aactcaccaa | aaaagctctt | attaaggagt | 1440 |
| atacggagga | gatagaacgt | ttaaaacgag | atcttgctgc | agcccgtgag | aaaaatggag | 1500 |
| tgtatatttc | tgaagaaaat | tttagagtca | tgagtggaaa | attaactgtt | caagaagagc | 1560 |
| agattgtaga | attgattgaa | aaaattggtg | ctgttgagga | ggagctgaat | agggttacag | 1620 |
| agttgtttat | ggataataaa | aatgaacttg | accagtgtaa | atctgacctg | caaaataaaa | 1680 |
| cacaagaact | tgaaaccact | caaaaacatt | tgcaagaaac | taaattacaa | cttgttaaag | 1740 |
| aagaatatat | cacatcagct | ttggaaagta | ctgaggagaa | acttcatgat | gctgccagca | 1800 |
| agctgcttaa | cacagttgaa | gaaactacaa | aagatgtatc | tggtctccat | tccaaactgg | 1860 |

```
atcgtaagaa ggcagttgac caacacaatg cagaagctca ggatattttt ggcaaaaacc    1920
tgaatagtct gtttaataat atggaagaat taattaagga tggcagctca aagcaaaagg    1980
ccatgctaga agtacataag accttatttg gtaatctgct gtcttccagt gtctctgcat    2040
tagataccat tactacagta gcacttggat ctctcacatc tattccagaa aatgtgtcta    2100
ctcatgtttc tcagattttt aatatgatac taaaagaaca atcattagca gcagaaagta    2160
aaactgtact acaggaattg attaatgtac tcaagactga tcttctaagt tcactggaaa    2220
tgattttatc cccaactgtg gtgtctatac tgaaaatcaa tagtcaacta aagcatattt    2280
tcaagacttc attgacagtg gccgataaga tagaagatca aaaaaaggaa ctagatggct    2340
ttctcagtat actgtgtaac aatctacatg aactacaaga aaataccatt tgttccttgg    2400
ttgagtcaca aaagcaatgt ggaaacctaa ctgaagacct gaagacaata aagcagaccc    2460
attcccagga actttgcaag ttaatgaatc tttggacaga gagattctgt gctttggagg    2520
aaaagtgtga aaatatacag aaaccactta gtagtgtcca ggaaaatata cagcagaaat    2580
ctaaggatat agtcaacaaa atgactttc acagtcaaaa attttgtgct gattctgatg    2640
gcttctcaca ggaactcaga aattttaacc aagaaggtac aaaattggtt gaagaatctg    2700
tgaaacactc tgataaactc aatggcaacc tggaaaaaat atctcaagag actgaacaga    2760
gatgtgaatc tctgaacaca agaacagttt attttctga acagtgggta tcttccttaa    2820
atgaaaggga acaggaactt cacaacttat tggaggttgt aagccaatgt tgtgaggctt    2880
caagttcaga catcactgag aaatcagatg gacgtaaggc agctcatgag aaacagcata    2940
acattttctc tgatcagatg actattgatg aagataaatt gatagcacaa aatctagaac    3000
ttaatgaaac cataaaaatt ggtttgacta agcttaattg ctttctggaa caggatctga    3060
aactggatat cccaacaggt acgacaccac agaggaaaag ttatttatac ccatcaacac    3120
tggtaagaac tgaaccacgt gaacatctcc ttgatcagct gaaaaggaaa cagcctgagc    3180
tgttaatgat gctaaactgt tcagaaaaca acaaagaaga gacaattccg gatgtggatg    3240
tagaagaggc agttctgggg cagtatactg aagaacctct aagtcaagag ccatctgtag    3300
atgctggtgt ggattgttca tcaattggcg gggttccatt tttccagcat aaaaaatcac    3360
atggaaaaga caaagaaaac agaggcatta acacactgga gaggtctaaa gtggaagaaa    3420
ctacagagca cttggttaca aagagcagat tacctctgcg agcccagatc aacctttaat    3480
tcacttgggg gttggcaatt ttattttaa agaaaactta aaaataaaac ctgaaaccc    3540 agaacttgag ccttgtgtat agattttaaa agaatatata tatcagccgg gcgcggtggc    3600
tcatgcctgt aatcccagca ctttgggagg ctgaggcggg tggattgctt gagcccagga    3660
gtttgagacc agcctggcca acgtggcaaa acctcgtctc tgttaaaaat tagccgggcg    3720
tggtggcaca ctcctgtaat cccagctact ggggaggctg aggcacgaga atcacttgaa    3780
cccaggaagc ggggttgcag tgagccaaag gtacaccact acactccagc tgggcaaca    3840 gagcaagact cggtctcaaa acaaaatttt aaaaagata taaggcagta ctgtaaattc    3900
agttgaattt tgatatctac ccatttttct gtcatccta tagttcactt tgtattaaat    3960 tgggttcat ttgggatttg caatgtaaat acgtatttct agttttcata taagtagtt    4020 ctttataac aaatgaaaag tattttctt gtatattatt aagtaatgaa tatataagaa    4080
ctgtactctt tcagcttga gcttacatag gtaaatatca ccaacatctg tccttagaaa    4140
ggaccatctc atgttttttt tcttgctatg acttgtgtat tttcttgcat cctccctaga    4200
cttccctatt tcgctttctc ctcggctcac tttctccctt tttattttc accaaaccat    4260
```

```
ttgtagagct acaaaaggta tcctttctta ttttcagtag tcagaatttt atctagaaat    4320
cttttaacac cttttagtg gttatttcta aaatcactgt caacaataaa tctacccta     4380 gttgtatccc tcctttcagt attttcact tgttgcccca aatgtgaaag catttcattc    4440
ctttaagagg cctaactcat tcaccctgac agagttcaca aaaagcccac ttaagagtat   4500
acattgctat tatgggagac cacccagaca tctgactaat ggctctgtgc ccacactcca   4560
agacctgtgc cttttagaga agctcacaat gatttaagga ctgtttgaaa cttccaatta   4620
tgtctataat ttatattctt tgtttacat gatgaaactt tttgttgttg cttgtttgta    4680
tataatacaa tgtgtacatg tatcttttc tcgattcaaa tcttaaccct taggactctg    4740 gtattttga tctggcaacc atatttctgg aagttgagat gtttcagctt gaagaaccaa    4800
aacagaagga atatgtacaa agaataaatt ttctgctcac gatgagttta gtgtgtaaag   4860
tttagagaca tctgactttg atagctaaat taaaccaaac cctattgaag aattgaatat   4920
atgctacttc aagaaactaa attgatctcg tagaattatc ttaataaaat aatggctata   4980
atttctctgc aaaatcagat gtcagcataa gcgatggata atacctaata aactgccctc   5040
agtaaatcca tggttaataa atgtggtttc tacattaaaa aaaaaaaaa aaaaaaaaa     5100 a                                                                     5101

<210> SEQ ID NO 12
<211> LENGTH: 444
<212> TYPE: RNA
<213> ORGANISM: Homo sapiens

<400> SEQUENCE: 12
augaacuuuc ugcugucuug ggugcauugg agccuugccu ugcugcucua ccuccaccau     60
gccaaguggu cccaggcugc acccauggca gaaggaggag ggcagaauca ucacgaagug    120
gugaaguuca uggaugucua ucagcgcagc uacugccauc caaucgagac ccugguggac    180 aucuccagg aguacccuga ugagaucgag uacaucuuca gccauccug ugugcccug      240 augcgaugcg ggggcugcug caaugacgag ggcuggagu gugugcccac ugaggaguccc    300 aacaucacca ugcagauuau gcggaucaaa ccucaccaag gccagcacau aggagagaug    360
agcuuccuac agcacaacaa augugaaugc agaccaaaga aagauagagc aagacaagaa    420
aaaugugaca agccgaggcg guga                                           444

<210> SEQ ID NO 13

<400> SEQUENCE: 13

000

<210> SEQ ID NO 14
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
accaaggcca gcacauagg                                                   19

<210> SEQ ID NO 15
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 15
ccaaggccag cacauagga                                                   19

<210> SEQ ID NO 16
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
ccaaggccag cacauagga                                                   19

<210> SEQ ID NO 17
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
aaggccagca cauaggaga                                                   19

<210> SEQ ID NO 18
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
aggccagcac auaggagag                                                   19

<210> SEQ ID NO 19
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
ggccagcaca uaggagaga                                                   19

<210> SEQ ID NO 20
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
gccagcacau aggagagau                                                   19

<210> SEQ ID NO 21
<211> LENGTH: 19
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 21
ccagcacaua ggagagaug                                               19

<210> SEQ ID NO 22
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
cagcacauag gagagauga                                               19

<210> SEQ ID NO 23
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
agcacauagg agagaugag                                               19

<210> SEQ ID NO 24
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
cacauaggag agaugagcu                                               19

<210> SEQ ID NO 25
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
acauaggaga gaugagcuu                                               19

<210> SEQ ID NO 26
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
cauaggagag augagcuuc                                               19

<210> SEQ ID NO 27
<211> LENGTH: 19
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 27
auaggagaga ugagcuucc                                                19

<210> SEQ ID NO 28
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
uaggagagau gagcuuccu                                                19

<210> SEQ ID NO 29
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
aggagagaug agcuuccua                                                19

<210> SEQ ID NO 30
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
ggagagauga gcuuccuac                                                19

<210> SEQ ID NO 31
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
gagagaugag cuuccuaca                                                19

<210> SEQ ID NO 32
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
agagaugagc uuccuacag                                                19

<210> SEQ ID NO 33
<211> LENGTH: 19
<212> TYPE: RNA
<213> ORGANISM: Artificial Sequence
<220> FEATURE:
<223> OTHER INFORMATION: Description of Artificial Sequence: Synthetic
```

-continued oligonucleotide

<400> SEQUENCE: 33
gagaugagcu uccuacagc                                                19

<210> SEQ ID NO 34
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
auguuccuua ucgagaauc                                                19

<210> SEQ ID NO 35
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
uguuccuuau cgagaaucu                                                19

<210> SEQ ID NO 36
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
guuccuuauc gagaaucua                                                19

<210> SEQ ID NO 37
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
uuccuuaucg agaaucuaa                                                19

<210> SEQ ID NO 38
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
uccuuaucga gaaucuaaa                                                19

<210> SEQ ID NO 39
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide -continued

<400> SEQUENCE: 39
ccuuaucgag aaucuaaac                                                    19

<210> SEQ ID NO 40
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
cuuaucgaga aucuaaacu                                                    19

<210> SEQ ID NO 41
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
uuaucgagaa ucuaaacua                                                    19

<210> SEQ ID NO 42
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
uaucgagaau cuaaacuaa                                                    19

<210> SEQ ID NO 43
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
aucgagaauc uaaacuaac                                                    19

<210> SEQ ID NO 44
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
cgagaaucua aacuaacua                                                    19

<210> SEQ ID NO 45
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 45
gagaaucuaa acuaacuag                                              19

<210> SEQ ID NO 46
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
agaaucuaaa cuaacuaga                                              19

<210> SEQ ID NO 47
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
gaaucuaaac uaacuagaa                                              19

<210> SEQ ID NO 48
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
aaucuaaacu aacuagaau                                              19

<210> SEQ ID NO 49
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
aucuaaacua acuagaauc                                              19

<210> SEQ ID NO 50
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
ucuaaacuaa cuagaaucc                                              19

<210> SEQ ID NO 51
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
```

```
cuaaacuaac uagaauccu                                                    19

<210> SEQ ID NO 52
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
uaaacuaacu agaauccuc                                                    19

<210> SEQ ID NO 53
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
aaacuaacua gaauccucc                                                    19

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 54
accaaggcca gcacauaggt t                                                 21

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 55
ccuaugugcu ggccuuggut t                                                 21

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 56
ccaaggccag cacauaggat t                                                 21

<210> SEQ ID NO 57
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 57
uccuaugugc uggccuuggt t                                              21

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 58
ccaaggccag cacauaggat t                                              21

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 59
cuccuaugug cuggccuugt t                                              21

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 60
aaggccagca cauaggagat t                                              21

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 61
ucuccuaugu gcuggccuut t                                              21
```

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 62
aggccagcac auaggagagt t                                              21

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 63
cucuccuaug ugcuggccut t                                              21

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 64
ggccagcaca uaggagagat t                                              21

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 65
ucucuccuau gugcuggcct t                                              21

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 66
gccagcacau aggagagaut t                                              21

```
<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 67
aucucuccua ugugcuggct t                                               21

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 68
ccagcacaua ggagagaugt t                                               21

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 69
caucucuccu augugcuggt t                                               21

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 70
cagcacauag gagagaugat t                                               21

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 71
ucaucucucc uaugugcugt t                                               21
```

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 72
agcacauagg agagaugagt t                                              21

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 73
cucaucucuc cuaugugcut t                                              21

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 74
cacauaggag agaugagcut t                                              21

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 75
agcucaucuc uccuaugugt t                                              21

<210> SEQ ID NO 76
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 76
acauaggaga gaugagcuut t            21

<210> SEQ ID NO 77
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 77
aagcucaucu cuccuaugut t            21

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 78
cauaggagag augagcuuct t            21

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 79
gaagcucauc ucuccuaugt t            21

<210> SEQ ID NO 80
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 80
auaggagaga ugagcuucct t            21

<210> SEQ ID NO 81
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 81
ggaagcucau cucuccuaut t                                          21

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 82
uaggagagau gagcuuccut t                                          21

<210> SEQ ID NO 83
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 83
aggaagcuca ucucuccuat t                                          21

<210> SEQ ID NO 84
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 84
aggagagaug agcuuccuat t                                          21

<210> SEQ ID NO 85
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 85
uaggaagcuc aucucccut t                                           21

<210> SEQ ID NO 86
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide -continued

```
<400> SEQUENCE: 86
ggagagauga gcuuccuact t                                          21

<210> SEQ ID NO 87
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 87
guaggaagcu caucucucct t                                          21

<210> SEQ ID NO 88
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 88
gagagaugag cuuccuacat t                                          21

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 89
uguaggaagc ucaucucuct t                                          21

<210> SEQ ID NO 90
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 90
agagaugagc uuccuacagt t                                          21

<210> SEQ ID NO 91
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

-continued

<400> SEQUENCE: 91
cuguaggaag cucaucucut t                                              21

<210> SEQ ID NO 92
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 92
gagaugagcu uccuacagct t                                              21

<210> SEQ ID NO 93
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 93
gcuguaggaa gcucaucuct t                                              21

<210> SEQ ID NO 94
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 94 auguccuua ucgagaauct t                                               21

<210> SEQ ID NO 95
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 95
gauucucgau aaggaacaut t                                              21

<210> SEQ ID NO 96
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 96
uguuccuuau cgagaaucut t                                              21

<210> SEQ ID NO 97
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 97
agauucucga uaaggaacat t                                              21

<210> SEQ ID NO 98
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 98
guuccuuauc gagaaucuat t                                              21

<210> SEQ ID NO 99
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 99
uagauucucg auaaggaact t                                              21

<210> SEQ ID NO 100
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 100
uuccuuaucg agaaucuaat t                                              21

<210> SEQ ID NO 101
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<223> OTHER INFORMATION: Description of Combined DNA/RNA Molecule:
      Synthetic oligonucleotide

<400> SEQUENCE: 101
uuagauucuc gauaaggaat t                                              21

<210> SEQ ID NO 102
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 102
uccuuaucga gaaucuaaat t                                              21

<210> SEQ ID NO 103
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 103
uuuagauucu cgauaaggat t                                              21

<210> SEQ ID NO 104
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 104
ccuuaucgag aaucuaaact t                                              21

<210> SEQ ID NO 105
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 105
guuuagauuc ucgauaaggt t                                              21

<210> SEQ ID NO 106
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 106
cuuaucgaga aucuaaacut t                                              21

<210> SEQ ID NO 107
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 107
aguuuagauu cucgauaagt t                                              21

<210> SEQ ID NO 108
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 108
uuaucgagaa ucuaaacuat t                                              21

<210> SEQ ID NO 109
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 109
uaguuuagau ucucgauaat t                                              21

<210> SEQ ID NO 110
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 110
uaucgagaau cuaaacuaat t                                              21

<210> SEQ ID NO 111
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
      oligonucleotide
<220> FEATURE:
<223> OTHER INFORMATION: Description of Combined DNA/RNA Molecule:
      Synthetic oligonucleotide

<400> SEQUENCE: 111
uuaguuuaga uucucgauat t                                          21

<210> SEQ ID NO 112
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 112
aucgagaauc uaaacuaact t                                          21

<210> SEQ ID NO 113
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 113
guuaguuuag auucucgaut t                                          21

<210> SEQ ID NO 114
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 114
cgagaaucua aacuaacuat t                                          21

<210> SEQ ID NO 115
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 115
uaguuaguuu agauucucgt t                                          21

<210> SEQ ID NO 116
<211> LENGTH: 21
<212> TYPE: DNA
<213> ORGANISM: Artificial Sequence
<220> FEATURE:
```

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 116
gagaaucuaa acuaacuagt t                                            21

<210> SEQ ID NO 117
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 117
cuaguuaguu uagauucuct t                                            21

<210> SEQ ID NO 118
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 118
agaaucuaaa cuaacuagat t                                            21

<210> SEQ ID NO 119
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 119
ucuaguuagu uuagauucut t                                            21

<210> SEQ ID NO 120
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 120
gaaucuaaac uaacuagaat t                                            21

<210> SEQ ID NO 121
<211> LENGTH: 21
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 121
uucuaguuag uuuagauuct t                                              21

<210> SEQ ID NO 122
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 122
aaucuaaacu aacagaaaut t                                              21

<210> SEQ ID NO 123
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 123
auucuaguua guuuagauut t                                              21

<210> SEQ ID NO 124
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 124
aucuaaacua acagaauct t                                               21

<210> SEQ ID NO 125
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 125 gauucaguu aguuuagaut t                                               21

<210> SEQ ID NO 126
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 126
ucuaaacuaa cuagaaucct t                                              21

<210> SEQ ID NO 127
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 127
ggauucuagu uaguuuagat t                                              21

<210> SEQ ID NO 128
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 128
cuaaacuaac uagaauccut t                                              21

<210> SEQ ID NO 129
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 129
aggauucuag uuaguuuagt t                                              21

<210> SEQ ID NO 130
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 130
uaaacuaacu agaauccuct t                                              21

<210> SEQ ID NO 131
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 131
gaggauucua guuaguuuat t                                              21

<210> SEQ ID NO 132
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 132
aaacuaacua gaauccucct t                                              21

<210> SEQ ID NO 133
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 133
ggaggauucu aguuaguuut t                                              21

<210> SEQ ID NO 134
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 134
accaaggcca gcacauagg                                                 19

<210> SEQ ID NO 135
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 135
ccaaggccag cacauagga                                                 19

<210> SEQ ID NO 136
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 136
caaggccagc acauaggag                                                    19

<210> SEQ ID NO 137
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 137
aaggccagca cauaggaga                                                    19

<210> SEQ ID NO 138
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 138
aggccagcac auaggagag                                                    19

<210> SEQ ID NO 139
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 139
ggccagcaca uaggagaga                                                    19

<210> SEQ ID NO 140
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 140
gccagcacau aggagagau                                                    19

<210> SEQ ID NO 141
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 141
ccagcacaua ggagagaug                                                    19

<210> SEQ ID NO 142
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 142
cagcacauag gagagauga                                                19

<210> SEQ ID NO 143
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 143
agcacauagg agagaugag                                                19

<210> SEQ ID NO 144
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 144
cacauaggag agaugagcu                                                19

<210> SEQ ID NO 145
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 145
acauaggaga gaugagcuu                                                19

<210> SEQ ID NO 146
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 146
cauaggagag augagcuuc                                                19

<210> SEQ ID NO 147
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 147
auaggagaga ugagcuucc                                                19

<210> SEQ ID NO 148
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 148
```
uaggagagau gagcuuccu 19

<210> SEQ ID NO 149
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 149
aggagagaug agcuuccua 19

<210> SEQ ID NO 150
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 150
ggagagauga gcuuccuac 19

<210> SEQ ID NO 151
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 151
gagagaugag cuuccuaca 19

<210> SEQ ID NO 152
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 152
agagaugagc uuccuacag 19

<210> SEQ ID NO 153
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 153
gagaugagcu uccuacagc 19

<210> SEQ ID NO 154
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 154
accaaggcca gcacauagga g                                         21

<210> SEQ ID NO 155
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 155
cuccuaugug cuggccuugg uga                                       23

<210> SEQ ID NO 156
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 156
ccaaggccag cacauaggag a                                         21

<210> SEQ ID NO 157
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 157
ucuccuaugu gcuggccuug gug                                       23

<210> SEQ ID NO 158
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 158
caaggccagc acauaggaga g                                         21

<210> SEQ ID NO 159
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 159
cucuccuaug ugcuggccuu ggu                                       23

<210> SEQ ID NO 160
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 160
aaggccagca cauaggagag a                                         21

-continued

```
<210> SEQ ID NO 161
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 161
ucucuccuau gugcuggccu ugg                                                 23

<210> SEQ ID NO 162
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 162
aggccagcac auaggagaga u                                                   21

<210> SEQ ID NO 163
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 163
aucucuccua ugugcuggcc uug                                                 23

<210> SEQ ID NO 164
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 164
ggccagcaca uaggagagau g                                                   21

<210> SEQ ID NO 165
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 165
caucucuccu augugcuggc cuu                                                 23

<210> SEQ ID NO 166
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 166
gccagcacau aggagagaug a                                                   21
```

```
<210> SEQ ID NO 167
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 167
ucaucucucc uaugugcugg ccu                                             23

<210> SEQ ID NO 168
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 168
ccagcacaua ggagagauga g                                               21

<210> SEQ ID NO 169
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 169
cucaucucuc cuaugugcug gcc                                             23

<210> SEQ ID NO 170
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 170
cagcacauag gagagaugag c                                               21

<210> SEQ ID NO 171
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 171
gcucaucucu ccuaugugcu ggc                                             23

<210> SEQ ID NO 172
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 172
agcacauagg agagaugagc u                                               21
```

```
<210> SEQ ID NO 173
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 173
agcucaucuc uccaugugc ugg                                              23

<210> SEQ ID NO 174
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 174
cacauaggag agaugagcuu c                                               21

<210> SEQ ID NO 175
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 175
gaagcucauc ucuccuaugu gcu                                             23

<210> SEQ ID NO 176
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 176
acauaggaga gaugagcuuc c                                               21

<210> SEQ ID NO 177
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 177
ggaagcucau cucuccuaug ugc                                             23

<210> SEQ ID NO 178
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 178
cauaggagag augagcuucc u                                               21

<210> SEQ ID NO 179
```

<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 179
aggaagcuca ucucuccuau gug                                          23

<210> SEQ ID NO 180
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 180
auaggagaga ugagcuuccu a                                            21

<210> SEQ ID NO 181
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 181
uaggaagcuc aucucuccua ugu                                          23

<210> SEQ ID NO 182
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 182
uaggagagau gagcuuccua c                                            21

<210> SEQ ID NO 183
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 183
guaggaagcu caucucuccu aug                                          23

<210> SEQ ID NO 184
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 184
aggagagaug agcuuccuac a                                            21

<210> SEQ ID NO 185
<211> LENGTH: 23

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 185
uguaggaagc ucaucucucc uau                                           23

<210> SEQ ID NO 186
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 186
ggagagauga gcuuccuaca g                                             21

<210> SEQ ID NO 187
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 187
cuguaggaag cucaucucuc cua                                           23

<210> SEQ ID NO 188
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 188
gagagaugag cuuccuacag c                                             21

<210> SEQ ID NO 189
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 189
gcuguaggaa gcucaucucu ccu                                           23

<210> SEQ ID NO 190
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 190
agagaugagc uuccuacagc a                                             21

<210> SEQ ID NO 191
<211> LENGTH: 23
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 191
ugcuguagga agcucaucuc ucc                                              23

<210> SEQ ID NO 192
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 192
gagaugagcu uccuacagca c                                                21

<210> SEQ ID NO 193
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 193
gugcuguagg aagcucaucu cuc                                              23
```

LIPID FORMULATED COMPOSITIONS AND METHODS FOR INHIBITING EXPRESSION OF EG5 AND VEGF GENES

RELATED APPLICATIONS

This application claims the benefit of U.S. Provisional Application No. 61/242,693, filed Sep. 15, 2009; U.S. Provisional Application No. 61/244,792, filed Sep. 22, 2009; U.S. Provisional Application No. 61/255,692, filed Oct. 28, 2009; U.S. Provisional Application No. 61/262,046, filed Nov. 17, 2009; U.S. Provisional Application No. 61/326,071, filed Apr. 20, 2010; and U.S. Provisional Application No. 61/352,128, filed Jun. 7, 2010, which are hereby incorporated in their entirety by reference.

SEQUENCE LISTING

This application includes a Sequence Listing submitted electronically as a text file named 17331US_sequencelisting.txt, created on Mar. 14, 2012, with a size of 60,584 bytes. The sequence listing is incorporated by reference.

FIELD OF THE INVENTION

This invention relates to administration of lipid formulated compositions containing double-stranded ribonucleic acid (dsRNA) to inhibit the expression of the human kinesin family member 11 (Eg5/KSP) and vascular endothelial growth factor (VEGF) genes, and the use of the compositions to treat pathological processes mediated by Eg5/KSP and VEGF expression, such as cancer, e.g., liver cancer.

BACKGROUND OF THE INVENTION

The maintenance of cell populations within an organism is governed by the cellular processes of cell division and programmed cell death. Within normal cells, the cellular events associated with the initiation and completion of each process is highly regulated. In proliferative disease such as cancer, one or both of these processes may be perturbed. For example, a cancer cell may have lost its regulation (checkpoint control) of the cell division cycle through either the overexpression of a positive regulator or the loss of a negative regulator, perhaps by mutation. Alternatively, a cancer cell may have lost the ability to undergo programmed cell death through the overexpression of a negative regulator. Hence, there is a need to develop new chemotherapeutic drugs that will restore the processes of checkpoint control and programmed cell death to cancerous cells.

One approach to the treatment of human cancers is to target a protein that is essential for cell cycle progression. In order for the cell cycle to proceed from one phase to the next, certain prerequisite events must be completed. There are checkpoints within the cell cycle that enforce the proper order of events and phases. One such checkpoint is the spindle checkpoint that occurs during the metaphase stage of mitosis. Small molecules that target proteins with essential functions in mitosis may initiate the spindle checkpoint to arrest cells in mitosis. Of the small molecules that arrest cells in mitosis, those which display anti-tumor activity in the clinic also induce apoptosis, the morphological changes associated with programmed cell death. An effective chemotherapeutic for the treatment of cancer may thus be one which induces checkpoint control and programmed cell death. Unfortunately, there are few compounds available for controlling these processes within the cell. Most compounds known to cause mitotic arrest and apoptosis act as tubulin binding agents. These compounds alter the dynamic instability of microtubules and indirectly alter the function/structure of the mitotic spindle thereby causing mitotic arrest. Because most of these compounds specifically target the tubulin protein which is a component of all microtubules, they may also affect one or more of the numerous normal cellular processes in which microtubules have a role. Hence, there is also a need for agents that more specifically target proteins associated with proliferating cells.

Human kinesin family member 11, e.g., Eg5 or KSP, is one of several kinesin-like motor proteins that are localized to the mitotic spindle and known to be required for formation and/or function of the bipolar mitotic spindle. There is a report of a small molecule that disturbs bipolarity of the mitotic spindle (Mayer, T. U. et. al. 1999. Science 286(5441) 971-4, herein incorporated by reference). More specifically, the small molecule induced the formation of an aberrant mitotic spindle wherein a monoastral array of microtubules emanated from a central pair of centrosomes, with chromosomes attached to the distal ends of the microtubules. The small molecule was dubbed "monastrol" after the monoastral array. This monoastral array phenotype had been previously observed in mitotic cells that were immunodepleted of the Eg5 motor protein. This distinctive monoastral array phenotype facilitated identification of monastrol as a potential inhibitor of Eg5. Indeed, monastrol was further shown to inhibit the Eg5 motor-driven motility of microtubules in an in vitro assay. The Eg5 inhibitor monastrol had no apparent effect upon the related kinesin motor or upon the motor(s) responsible for golgi apparatus movement within the cell. Cells that display the monoastral array phenotype either through immunodepletion of Eg5 or monastrol inhibition of Eg5 arrest in M-phase of the cell cycle. However, the mitotic arrest induced by either immunodepletion or inhibition of Eg5 is transient (Kapoor, T. M., 2000. J Cell Biol 150(5) 975-80). Both the monoastral array phenotype and the cell cycle arrest in mitosis induced by monastrol are reversible. Cells recover to form a normal bipolar mitotic spindle, to complete mitosis and to proceed through the cell cycle and normal cell proliferation. These data suggest that an inhibitor of Eg5 which induced a transient mitotic arrest may not be effective for the treatment of cancer cell proliferation.

Vascular endothelial growth factor (VEGF), also known as vascular permeability factor, VPF) is a multifunctional cytokine that stimulates angiogenesis, epithelial cell proliferation, and endothelial cell survival. VEGF can be produced by a wide variety of tissues, and its overexpression or aberrant expression can result in a variety disorders, including cancers and retinal disorders such as age-related macular degeneration and other angiogenic disorders.

Therefore, there is a need to explore the use of compounds that modulate both Eg5/KSP and VEGF expression to treat human disorders, e.g., cancer.

Recently, double-stranded RNA molecules (dsRNA) have been shown to block gene expression in a highly conserved regulatory mechanism known as RNA interference (RNAi). WO 99/32619 (Fire et al.) discloses the use of a dsRNA of at least 25 nucleotides in length to inhibit the expression of genes in *C. elegans*. dsRNA has also been shown to degrade target RNA in other organisms, including plants (see, e.g., WO 99/53050, Waterhouse et al.; and WO 99/61631, Heifetz et al.), *Drosophila* (see, e.g., Yang, D., et al., *Curr. Biol.* (2000) 10:1191-1200), and mammals (see WO 00/44895, Limmer; and DE 101 00 586.5, Kreutzer et al.). This natural mechanism has now become the focus for the development of a new class of pharmaceutical agents for treating disorders that are caused by the aberrant or unwanted regulation of a gene.

Sequences of siRNA targeting VEGF, including AD-3133, are described in U.S. patent application Ser. No. 11/078,073 filed Mar. 11, 2005 (US Patent publication no 2006-0094032) and US continuation-in-part patent application Ser. No. 12/754,110, filed Jan. 25, 2006 (US patent application publication no. 2006-0223770).

Sequences of siRNA targeting Eg5/KSP including AD-12115 are described in U.S. patent application Ser. No. 11/694,215 filed Mar. 30, 2007 (now U.S. Pat. No. 7,718,629) and U.S. divisional patent application Ser. No. 12/754,110, filed Apr. 5, 2010 (US patent application publication no. 2011/0015250).

Lipid formulations, including DLinDMA comprising formulations, of siRNA targeting VEGF including AD-3133 and siRNA targeting Eg5/KSP including AD-12115 are described in U.S. patent application Ser. No. 12/552,207 filed Sep. 1, 2009 (US patent publication no. 2010/0087508) and International patent application no. PCT/US2009/036223, filed Mar. 5, 2009 (WO 2009/111658).

Lipid formulations of VEGF targeting siRNA including AD-3133 and Eg5/KSP targeting siRNA including AD-12115 are also described in U.S. patent application Ser. No. 12/723,471 filed Mar. 12, 2010 (US patent publication no. 2010/0267806) and International patent application no. PCT/US2010/027210, filed Mar. 12, 2010 (WO 2010/105209).

The contents of these applications are incorporated by reference for all purposes. In particular, the sequences of the siRNA disclosed in these applications, e.g., Tables 1 and 2, are incorporated by reference for all purposes.

SUMMARY OF THE INVENTION

Disclosed are methods for treating a subject in need of a treatment, comprising administering to the subject a dosage of a composition comprising ALN-VSP02 via intravenous (IV) infusion once every 2 weeks. Also disclosed are methods for treating a subject in need of treatment, comprising administering to the subject a composition comprising ALN-VSP02, the composition administered via intravenous infusion in a dosage selected form the group consisting of at least 0.1, 0.2, 0.3, 0.4, 0.7, 1.0, 1.25, 1.5, 1.7, 2.0, 3.0, and 6.0 mg/kg.

In one embodiment, the subject has cancer. In a further embodiment, the subject has advanced cancer with liver involvement. In one aspect, the dosage of ALN-VSP02 is selected from a group consisting of, e.g., at least 0.1, 0.2, 0.3, 0.4, 0.7, 1.0, 1.25, 1.5, 1.7, 2.0, 3.0, and at least 6.0 mg/kg; or e.g., 0.1, 0.2, 0.4, and at 0.7 mg/kg. In another aspect, the dosage is at least 0.4 mg/kg. In yet another aspect, the dosage is at least 0.7 mg/kg.

As described herein, the duration of each IV infusion in one embodiment is 15 minutes. In another embodiment, the composition is administered to the subject, e.g., once every two weeks for at least four weeks, or, e.g., once every two weeks for at least eight weeks. In one aspect, the invention comprises preadministration with at least one compound selected from the group consisting of dexamethasone, H1 and H2 blockers, and acetaminophen.

Included in the inventions are compositions comprising ALN-VSP02, wherein the $C_{max}$ and AUC of the composition as measurable in the subject's plasma are dose-proportional after the composition is administered to a subject. Also included in the inventions are a method of treating a human having advanced cancer with liver involvement, comprising administering to the human a dosage of a composition comprising at least 0.7 mg/kg ALN-VSP02 via 15 minute intravenous (IV) infusion once every 2 weeks for eight weeks.

In one aspect of the invention, the ALN-VSP02 provides a mean KSP siRNA $AUC_{0-last}$ from 10 to 800 µg*min/mL, a mean KSP siRNA $C_{max}$ from 0.4 to 13 µg/mL, a mean VEGF siRNA $AUC_{0-last}$ from 10 to 800 µg*min/mL and a mean VEGF siRNA $C_{max}$ from 0.4 to 13 µg/mL as measurable in the subject's plasma after the composition is administered to the subject. In another aspect, the $AUC_{0-last}$ of KSP siRNA is within about 80% to about 120% of a value selected, wherein said value is 30.9±21.1 µg*min/mL, 130.7±44.9 µg*min/mL, 201.3±38.6 µg*min/mL or 501.2±203.9 µg*min/mL as measurable in the subject's plasma after the composition is administered to the subject. In still another aspect, the $AUC_{0-last}$ of VEGF siRNA is within about 80% to about 120% of a value selected, wherein said value is 36.3±20.8 µg*min/mL, 140.3±56.1 µg*min/mL, 207.7±36.3 µg*min/mL or 610.9±223.3 µg*min/mL as measurable in the subject's plasma after the composition is administered to the subject. In one embodiment of the invention, the $C_{max}$ of KSP siRNA is within about 80% to about 120% of a value selected, wherein said value is 0.76±0.36 µg/mL, 2.3±0.54 µg/mL, 3.2±1.2 µg/mL and 9.8±4.1 µg/mL as measurable in the subject's plasma after the composition is administered to the subject. In another embodiment of the invention, the $C_{max}$ of VEGF siRNA is within about 80% to about 120% of a value selected, wherein said value is 0.86±0.43 µg/mL, 2.5±0.56 µg/mL, 3.7±1.2 µg/mL and 9.7±2.7 µg/mL as measurable in the subject's plasma after the composition is administered to the subject.

In one embodiment of the invention, the composition has a dose-proportional $C_{max}$ and AUC as measurable in the subject's plasma after the composition is administered to the subject. In a further embodiment, the dosage is about 0.1 to about 0.7 mg/kg.

In some embodiments, the dose-proportional AUC of KSP siRNA or VEGF siRNA is 10 to 800 µg*min/mL as is measurable in the subject's plasma after the composition is administered to the subject. In another embodiment, the dose-proportional $C_{max}$ of KSP siRNA or VEGF siRNA is 0.4 to 13 µg/mL as is measurable in the subject's plasma after the composition is administered to the subject. In yet another embodiment, the AUC value is within an error of ±3 to 4-fold of a predicted AUC value, both for VEGF siRNA and for KSP siRNA after the composition is administered to the subject. In one aspect, the rate of clearance for the composition (CL) is 103 mL/min as measurable in the subject's plasma after the composition is administered to the subject.

DETAILED DESCRIPTION OF THE INVENTION

Figure 1:
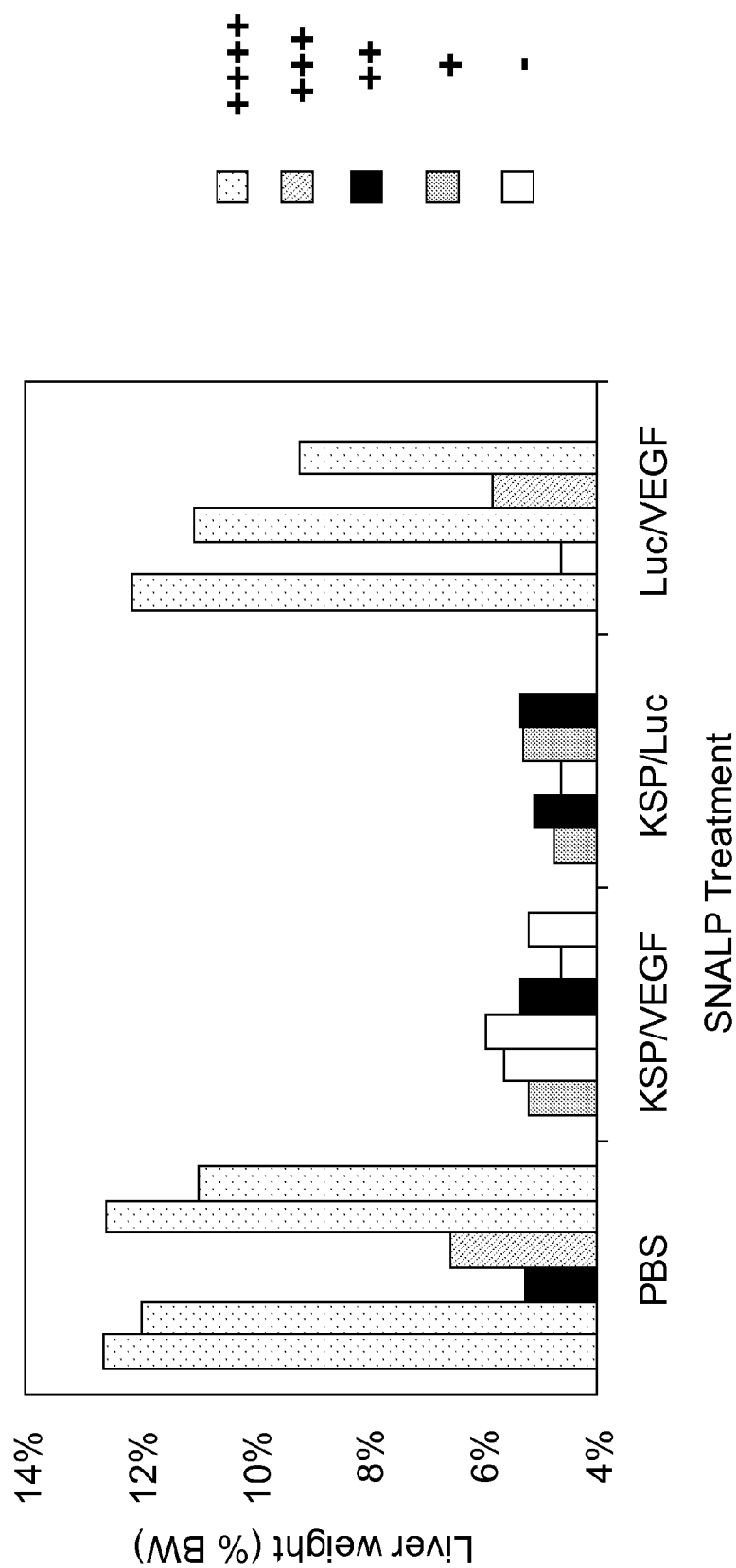
FIG. 1 is a graph showing liver weights as percentage of body weight following administration of SNALP-siRNAs in a Hep3B mouse model.
Figure 2A:
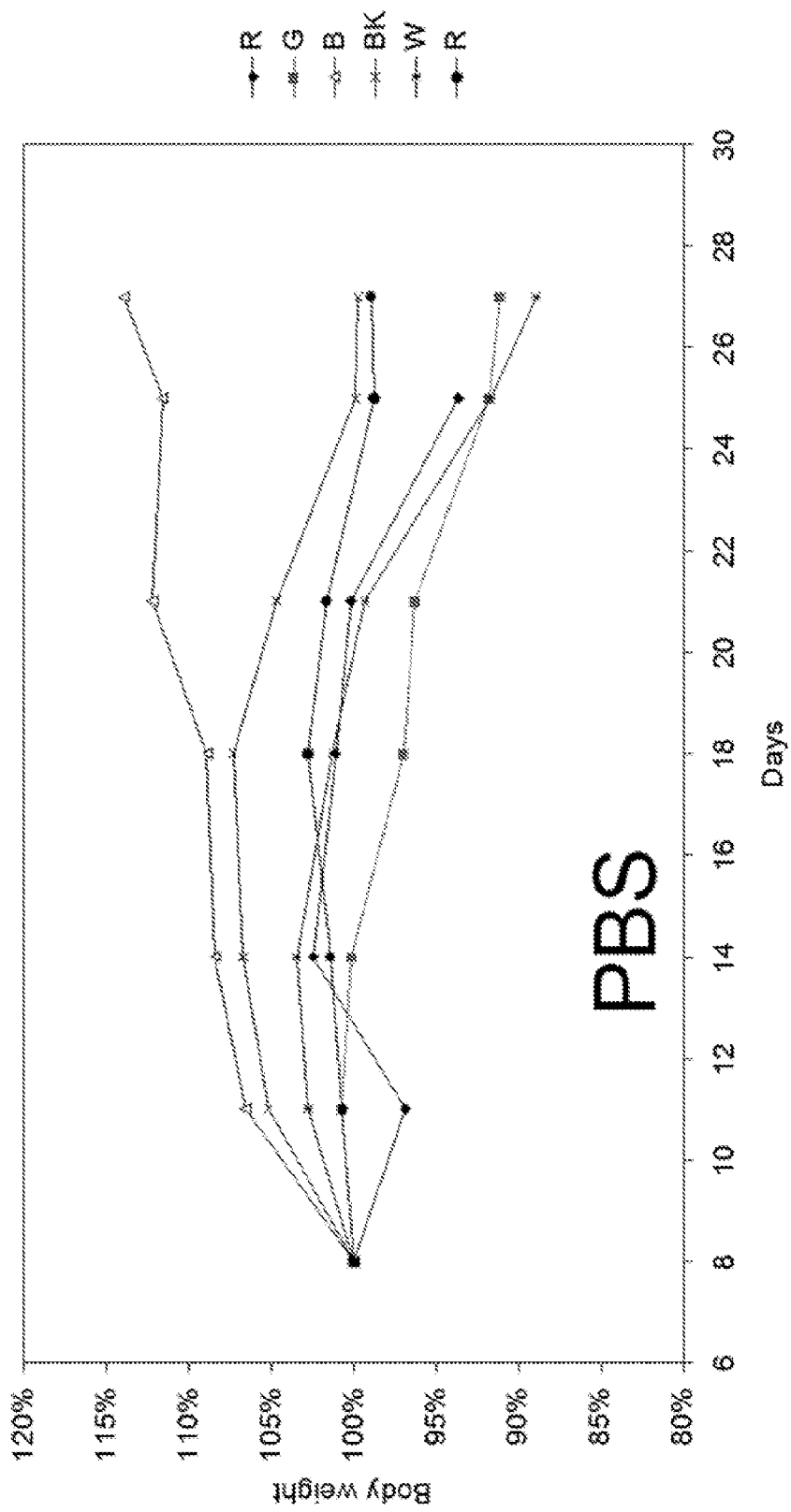
FIGS. 2A-2D are graphs showing the effects of SNALP-siRNAs on body weight in a Hep3B mouse model.
Figure 2B:
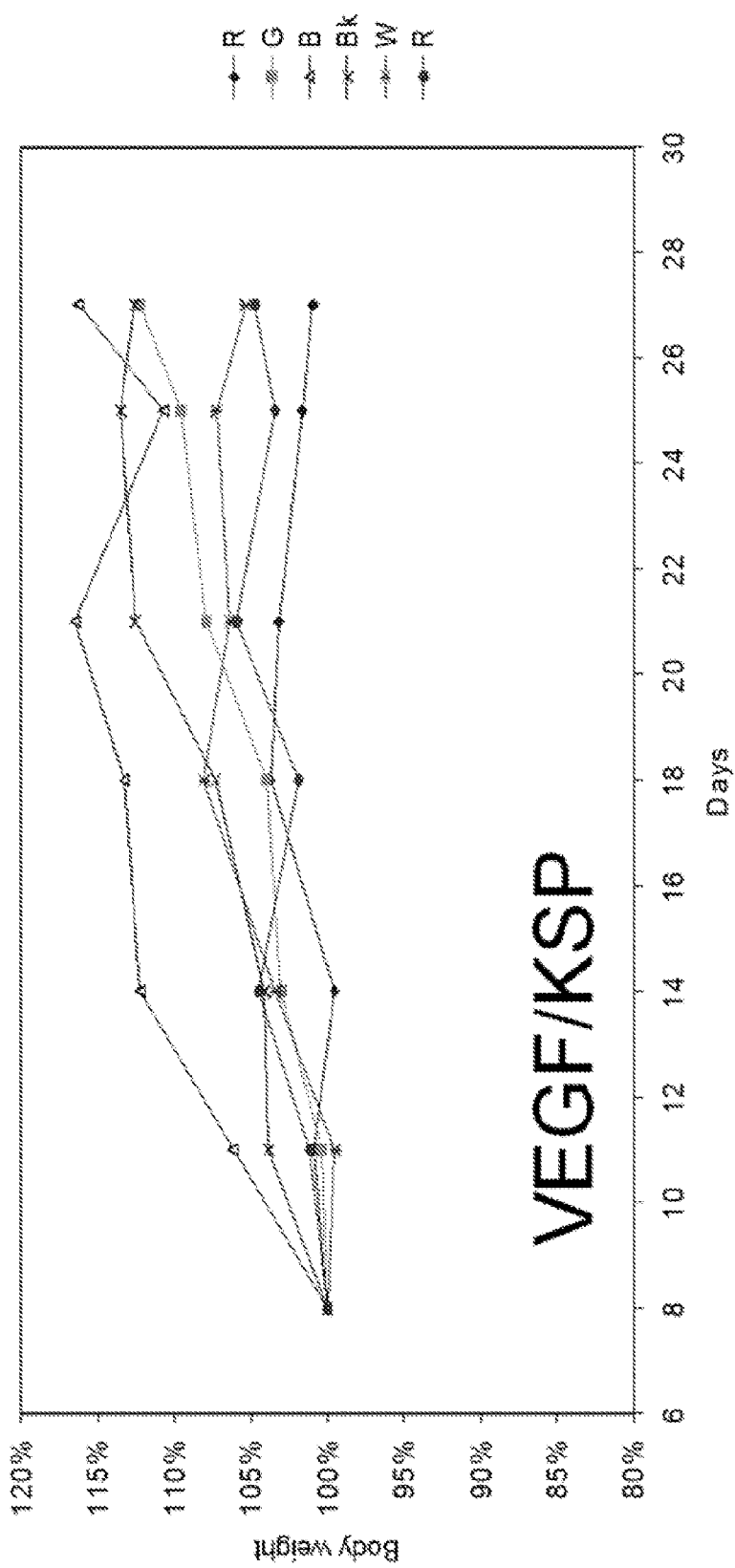
Figure 2C:
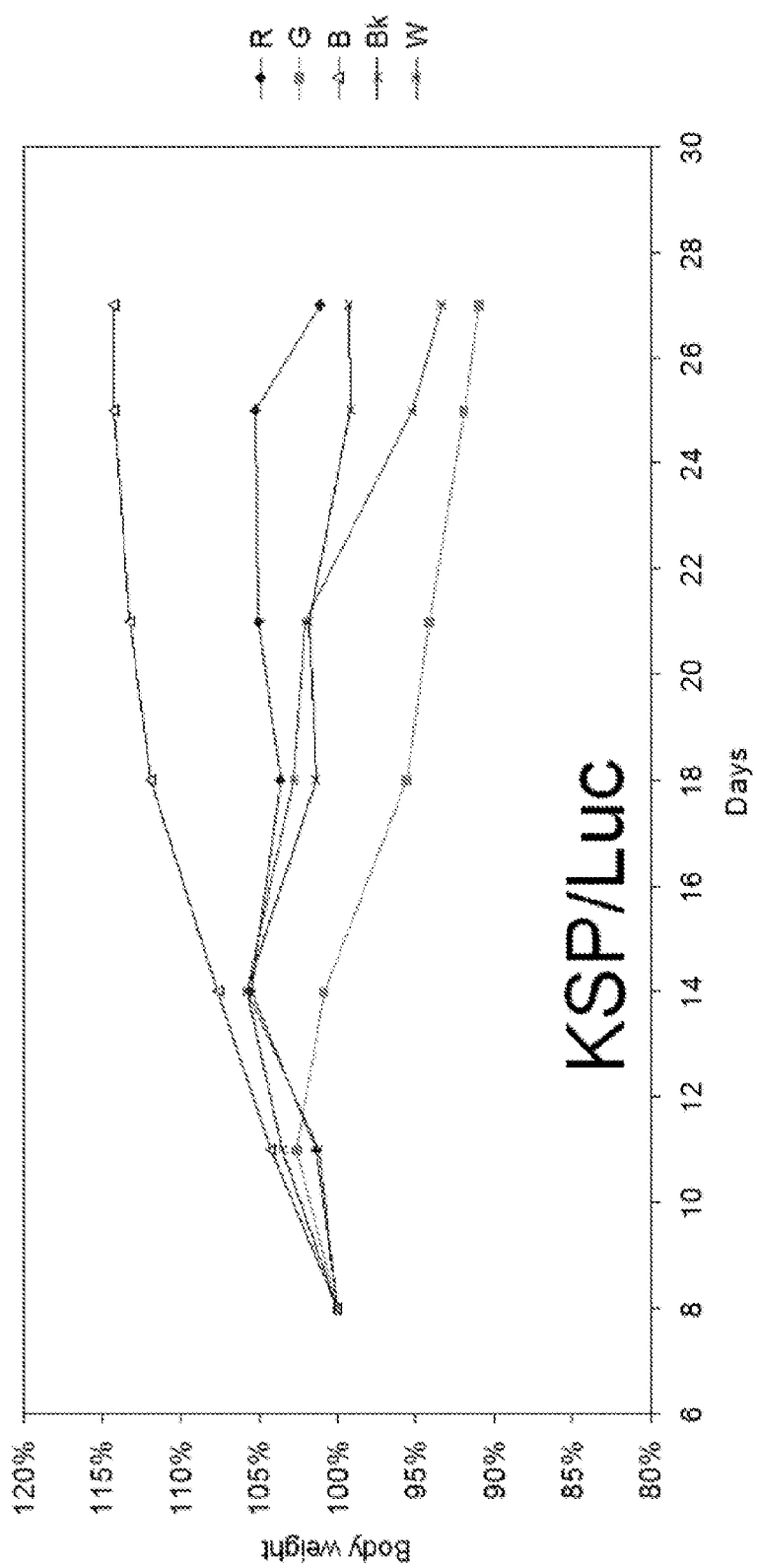
Figure 2D:
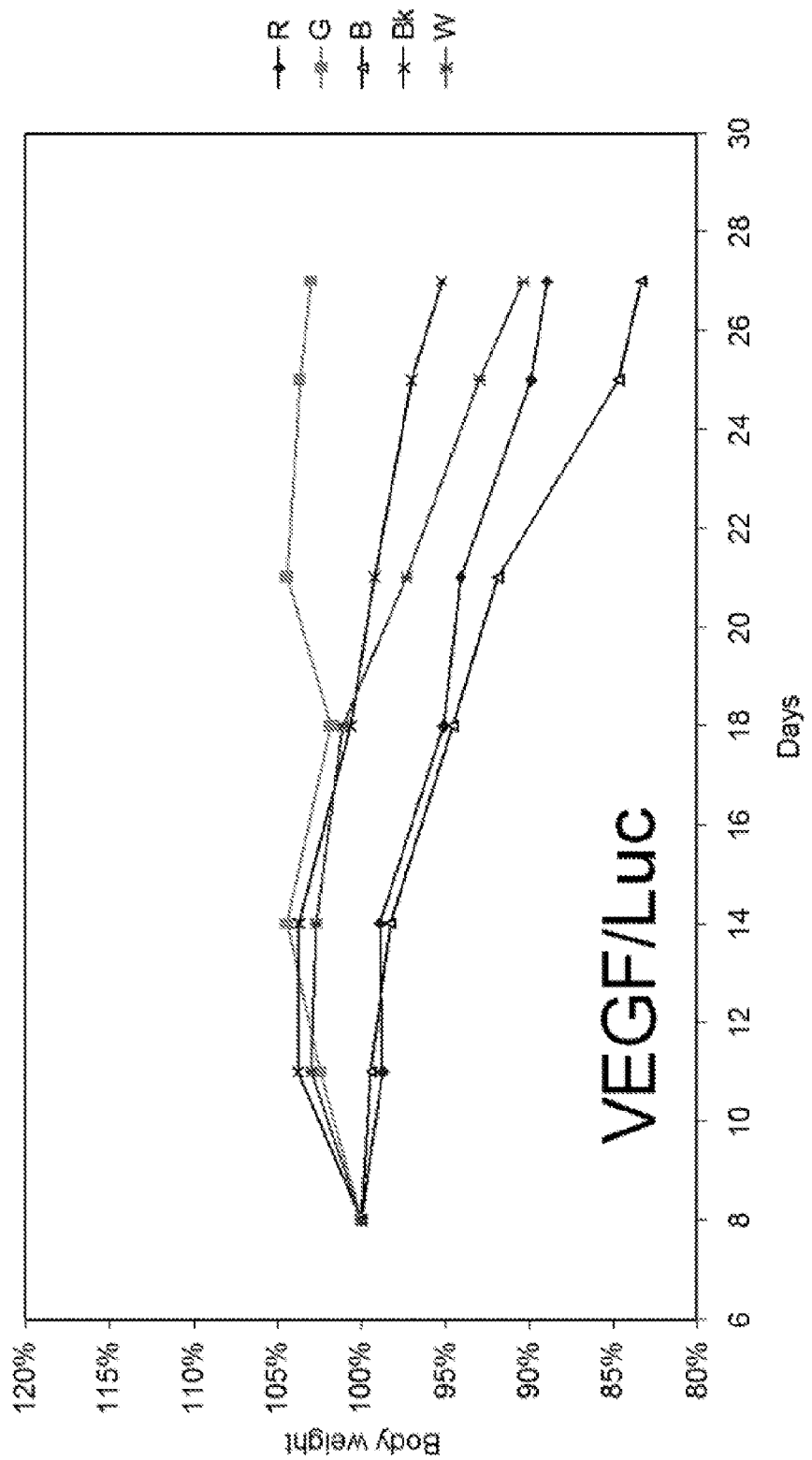

The invention provide methods of treatment, e.g., methods of treatment of liver cancer, via IV infusion administration of a lipid formulated composition having two siRNAs, one targeting the Eg5/KSP gene, and one targeting the VEGF gene. In some embodiments the composition is ALN-VSP02, as described herein. The composition can be administered once every two weeks, e.g., once every two weeks for at least 8 weeks. The composition can be administered at a dosage of at least 0.4 mg/kg or at least 0.7 mg/kg. The described method of treatment is well tolerated in patients. Measurement of siRNA concentrations in plasma after administration of the composition shows dose proportional Cmax and AUC with no evidence of drug accumulation.

I. Definitions

For convenience, the meaning of certain terms and phrases used in the specification, examples, and appended claims, are provided below. If there is an apparent discrepancy between the usage of a term in other parts of this specification and its definition provided in this section, the definition in this section shall prevail.

"G,", "C," "A" and "U" each generally stand for a nucleotide that contains guanine, cytosine, adenine, and uracil as a base, respectively. "T" and "dT" are used interchangeably herein and refer to a deoxyribonucleotide wherein the nucleobase is thymine, e.g., deoxyribothymine. However, it will be understood that the term "ribonucleotide" or "nucleotide" can also refer to a modified nucleotide, as further detailed below, or a surrogate replacement moiety. The skilled person is well aware that guanine, cytosine, adenine, and uracil may be replaced by other moieties without substantially altering the base pairing properties of an oligonucleotide comprising a nucleotide bearing such replacement moiety. For example, without limitation, a nucleotide comprising inosine as its base may base pair with nucleotides containing adenine, cytosine, or uracil. Hence, nucleotides containing uracil, guanine, or adenine may be replaced in the nucleotide sequences of the invention by a nucleotide containing, for example, inosine. In another example, adenine and cytosine anywhere in the oligonucleotide can be replaced with guanine and uracil, respectively to form G-U Wobble base pairing with the target mRNA. Sequences comprising such replacement moieties are embodiments of the invention.

As used herein, "Eg5" refers to the human kinesin family member 11, which is also known as KIF11, Eg5, HKSP, KSP, KNSL1 or TRIPS. Eg5 sequence can be found as NCBI GeneID:3832, HGNC ID: HGNC:6388 and RefSeq ID number: NM 004523. The terms "Eg5" and "KSP" and "Eg5/KSP" are used interchangeably.

As used herein, vascular endothelial growth factor (VEGF), also known as vascular permeability factor, is an angiogenic growth factor. VEGF is a homodimeric 45 kDa glycoprotein that exists in at least three different isoforms. VEGF isoforms are expressed in endothelial cells. The VEGF gene contains 8 exons that express a 189-amino acid protein isoform. A 165-amino acid isoform lacks the residues encoded by exon 6, whereas a 121-amino acid isoform lacks the residues encoded by exons 6 and 7. VEGF145 is an isoform predicted to contain 145 amino acids and to lack exon 7. VEGF can act on endothelial cells by binding to an endothelial tyrosine kinase receptor, such as Flt-1 (VEGFR-1) or KDR/flk-1 (VEGFR-2). VEGFR-2 is expressed in endothelial cells and is involved in endothelial cell differentiation and vasculogenesis. A third receptor, VEGFR-3, has been implicated in lymphogenesis.

The various isoforms have different biologic activities and clinical implications. For example, VEGF145 induces angiogenesis and like VEGF189 (but unlike VEGF165) VEGF 145 binds efficiently to the extracellular matrix by a mechanism that is not dependent on extracellular matrix-associated heparin sulfates. VEGF displays activity as an endothelial cell mitogen and chemoattractant in vitro and induces vascular permeability and angiogenesis in vivo. VEGF is secreted by a wide variety of cancer cell types and promotes the growth of tumors by inducing the development of tumor-associated vasculature. Inhibition of VEGF function has been shown to limit both the growth of primary experimental tumors as well as the incidence of metastases in immunocompromised mice.

As used herein, "target sequence" refers to a contiguous portion of the nucleotide sequence of an mRNA molecule formed during the transcription of the Eg5/KSP and/or VEGF gene, including mRNA that is a product of RNA processing of a primary transcription product.

As used herein, the term "strand comprising a sequence" refers to an oligonucleotide comprising a chain of nucleotides that is described by the sequence referred to using the standard nucleotide nomenclature.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions may include: 400 mM NaCl, 40 mM PIPES pH 6.4, 1 mM EDTA, 50° C. or 70° C. for 12-16 hours followed by washing. Other conditions, such as physiologically relevant conditions as may be encountered inside an organism, can apply. The skilled person will be able to determine the set of conditions most appropriate for a test of complementarity of two sequences in accordance with the ultimate application of the hybridized nucleotides.

This includes base-pairing of the oligonucleotide or polynucleotide comprising the first nucleotide sequence to the oligonucleotide or polynucleotide comprising the second nucleotide sequence over the entire length of the first and second nucleotide sequence. Such sequences can be referred to as "fully complementary" with respect to each other herein. However, where a first sequence is referred to as "substantially complementary" with respect to a second sequence herein, the two sequences can be fully complementary, or they may form one or more, but generally not more than 4, 3 or 2 mismatched base pairs upon hybridization, while retaining the ability to hybridize under the conditions most relevant to their ultimate application. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, may yet be referred to as "fully complementary" for the purposes of the invention.

"Complementary" sequences, as used herein, may also include, or be formed entirely from, non-Watson-Crick base pairs and/or base pairs formed from non-natural and modified nucleotides, in as far as the above requirements with respect to their ability to hybridize are fulfilled. Such non-Watson-Crick base pairs includes, but not limited to, G:U Wobble or Hoogstein base pairing.

The terms "complementary", "fully complementary" and "substantially complementary" herein may be used with respect to the base matching between the sense strand and the antisense strand of a dsRNA, or between the antisense strand of a dsRNA and a target sequence, as will be understood from the context of their use.

As used herein, a polynucleotide which is "substantially complementary to at least part of" a messenger RNA (mRNA) refers to a polynucleotide which is substantially complementary to a contiguous portion of the mRNA of interest (e.g., encoding Eg5/KSP and/or VEGF) including a 5' UTR, an open reading frame (ORF), or a 3' UTR. For example, a polynucleotide is complementary to at least a part of a Eg5 mRNA if the sequence is substantially complementary to a non-interrupted portion of a mRNA encoding Eg5.

The term "double-stranded RNA" or "dsRNA", as used herein, refers to a duplex structure comprising two anti-parallel and substantially complementary, as defined above, nucleic acid strands. The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5' end of the respective other strand forming the duplex structure, the connecting RNA chain is referred to as a "hairpin loop". Where the two strands are connected covalently by means other than an uninterrupted chain of nucleotides between the 3'-end of one strand and the 5'end of the respective other strand forming the duplex structure, the connecting structure is referred to as a "linker". The RNA strands may have the same or a different number of nucleotides. The maximum number of base pairs is the number of nucleotides in the shortest strand of the dsRNA minus any overhangs that are present in the duplex. In addition to the duplex structure, a dsRNA may comprise one or more nucleotide overhangs. In general, the majority of nucleotides of each strand are ribonucleotides, but as described in detail herein, each or both strands can also include at least one non-ribonucleotide, e.g., a deoxyribonucleotide and/or a modified nucleotide. In addition, as used in this specification, "dsRNA" may include chemical modifications to ribonucleotides, including substantial modifications at multiple nucleotides and including all types of modifications disclosed herein or known in the art. Any such modifications, as used in an siRNA type molecule, are encompassed by "dsRNA" for the purposes of this specification and claims.

As used herein, a "nucleotide overhang" refers to the unpaired nucleotide or nucleotides that protrude from the duplex structure of a dsRNA when a 3'-end of one strand of the dsRNA extends beyond the 5'-end of the other strand, or vice versa. "Blunt" or "blunt end" means that there are no unpaired nucleotides at that end of the dsRNA, i.e., no nucleotide overhang. A "blunt ended" dsRNA is a dsRNA that is double-stranded over its entire length, i.e., no nucleotide overhang at either end of the molecule. In some embodiments the dsRNA can have a nucleotide overhang at one end of the duplex and a blunt end at the other end.

The term "antisense strand" refers to the strand of a dsRNA which includes a region that is substantially complementary to a target sequence. As used herein, the term "region of complementarity" refers to the region on the antisense strand that is substantially complementary to a sequence, for example a target sequence, as defined herein. Where the region of complementarity is not fully complementary to the target sequence, the mismatches may be in the internal or terminal regions of the molecule. Generally the most tolerated mismatches are in the terminal regions, e.g., within 6, 5, 4, 3, or 2 nucleotides of the 5' and/or 3' terminus.

The term "sense strand," as used herein, refers to the strand of a dsRNA that includes a region that is substantially complementary to a region of the antisense strand.

As used herein, the term "SNALP" refers to a stable nucleic acid-lipid particle. A SNALP represents a vesicle of lipids coating a reduced aqueous interior comprising a nucleic acid such as an iRNA agent or a plasmid from which an iRNA agent is transcribed.

"Introducing into a cell", when referring to a dsRNA, means facilitating uptake or absorption into the cell, as is understood by those skilled in the art. Absorption or uptake of dsRNA can occur through unaided diffusive or active cellular processes, or by auxiliary agents or devices. The meaning of this term is not limited to cells in vitro; a dsRNA may also be "introduced into a cell", wherein the cell is part of a living organism. In such instance, introduction into the cell will include the delivery to the organism. For example, for in vivo delivery, dsRNA can be injected into a tissue site or administered systemically. In vitro introduction into a cell includes methods known in the art such as electroporation and lipofection.

The terms "silence" and "inhibit the expression of" "downregulate the expression of," "suppress the expression of" and the like in as far as they refer to the Eg5 and/or VEGF gene, herein refer to the at least partial suppression of the expression of the Eg5 and/or VEGF gene, as manifested by a reduction of the amount of Eg5 mRNA and/or VEGF mRNA which may be isolated from a first cell or group of cells in which the Eg5 and/or VEGF gene is transcribed and which has or have been treated such that the expression of the Eg5 and/or VEGF gene is inhibited, as compared to a second cell or group of cells substantially identical to the first cell or group of cells but which has or have not been so treated (control cells). The degree of inhibition is usually expressed in terms of $$\frac{(mRNA \text{ in control cells}) - (mRNA \text{ in treated cells})}{(mRNA \text{ in control cells})} \cdot 100\%$$

Alternatively, the degree of inhibition may be given in terms of a reduction of a parameter that is functionally linked to Eg5 and/or VEGF gene expression, e.g. the amount of protein encoded by the Eg5 and/or VEGF gene which is produced by a cell, or the number of cells displaying a certain phenotype, e.g. apoptosis. In principle, target gene silencing can be determined in any cell expressing the target, either constitutively or by genomic engineering, and by any appropriate assay. However, when a reference is needed in order to determine whether a given dsRNA inhibits the expression of the Eg5 and/or VEGF gene by a certain degree and therefore is encompassed by the instant invention, the assay provided in the Examples below shall serve as such reference.

For example, in certain instances, expression of the Eg5 and/or VEGF is suppressed by at least about 5%, 10%, 15%, 20%, 25%, 30%, 35%, 40%, 45%, or 50% by administration of the double-stranded oligonucleotide of the invention. In some embodiments, the Eg5 and/or VEGF gene is suppressed by at least about 60%, 70%, or 80% by administration of the double-stranded oligonucleotide of the invention. In other embodiments, the Eg5 and/or VEGF gene is suppressed by at least about 85%, 90%, or 95% by administration of the double-stranded oligonucleotide of the invention. The Example below provides values for inhibition of expression using various Eg5 and/or VEGF dsRNA molecules at various concentrations.

As used herein in the context of Eg5 and/or VEGF the terms "treat", "treatment", and the like, refer to relief from or alleviation of pathological processes mediated by Eg5 and/or VEGF expression. In the context of the present invention insofar as it relates to any of the other conditions recited herein below (other than pathological processes mediated by Eg5 and/or VEGF expression), the terms "treat", "treatment", and the like mean to relieve or alleviate at least one symptom associated with such condition, or to slow or reverse the progression of such condition, such as the slowing and progression of hepatic carcinoma.

As used herein, the phrases "therapeutically effective amount" refers to an amount that provides a therapeutic benefit in the treatment or management of pathological processes mediated by Eg5 and/or VEGF expression or an overt symptom of pathological processes mediated by Eg5 and/or VEGF expression. The specific amount that is therapeutically effective can be readily determined by ordinary medical practitioner, and can vary depending on factors known in the art, such as, e.g. the type of pathological processes mediated by Eg5 and/or VEGF expression, the patient's history and age, the stage of pathological processes mediated by Eg5 and/or VEGF expression, and the administration of other anti-pathological processes mediated by Eg5 and/or VEGF expression agents.

As used herein, a "pharmaceutical composition" comprises a pharmacologically effective amount of a dsRNA and a pharmaceutically acceptable carrier. As used herein, "pharmacologically effective amount," "therapeutically effective amount" or simply "effective amount" refers to that amount of an RNA effective to produce the intended pharmacological or therapeutic result. For example, if a given clinical treatment is considered effective when there is at least a 25% reduction in a measurable parameter associated with a disease or disorder, a therapeutically effective amount of a drug for the treatment of that disease or disorder is the amount necessary to effect at least a 25% reduction in that parameter.

The term "pharmaceutically acceptable carrier" refers to a carrier for administration of a therapeutic agent. As described in more detail below, such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

As used herein, a "transformed cell" is a cell into which a vector has been introduced from which a dsRNA molecule may be expressed.

The term "ALN-VSP02" refers to a SNALP formulated composition comprising two siRNAs: an siRNA targeting Eg5/KSP (AD12115), and an siRNA targeting VEGF (AD3133). A detailed description of ALN-VSP02 is described below in Example 9. The sequence of each ALN-VSP02 siRNA is as follows:

| Duplex ID | Target | Sense (5' to 3') | Antisense (5' to 3') |
|---|---|---|---|
| AD12115 | Eg5/KSP | ucGAGAAucuAAAcuAAcuTsT (SEQ ID NO: 1) | AGUuAGUUuAGAUUCUCGATsT (SEQ ID NO: 2) |
| AD3133 | VEGF | GcAcAuAGGAGAGAuGAGCUsU (SEQ ID NO: 3) | AAGCUcAUCUCUCCuAuGuGCusG (SEQ ID NO: 4) |

Key: A, G, C, U-ribonucleotides; c, u-2'-O-Me ribonucleotides; s-phosphorothioate.

The SNALP formulation is as follows:

| Component | Proportion (mg/mL) |
|---|---|
| AD12115 and AD3133 | 2.0* |
| DLinDMA (1,2-Dilinoleyloxy-N,N-dimethyl-3-aminopropane), | 7.3 |
| DPPC (R-1,2-Dipalmitoyl-sn-glycero-3-phosphocholine) | 1.1 |
| Cholesterol, Synthetic | 2.8 |
| PEG2000-C-DMA (3-N-[(ω-Methoxy poly(ethylene glycol) 2000) carbamoyl]-1,2-dimyristyloxy-propylamine) | 0.8 |
| Phosphate Buffered Saline (PBS) | q.s. |

The corresponding mol % for the proportions described in this table are as follows: 57.1/7.1/34.4/1.4 (DLinDMA/DPPC/Cholesterol/PEG2000-C-DMA).

As used herein, the term "intravenous (IV) infusion" refers to a method of administration of a composition directly into the vein of a patient. IV infusion allows for direct administration of a composition to the bloodstream of a patient. This can be performed, for example, via subcutaneous or intradermal infusion. IV infusion can be performed in many ways, including through the use of an injection needle, or possibly with an infusion pump. It can be provided as, for example, a continuous infusion, an intermittent infusion, a patient-controlled infusion, or a circadian infusion.

As used herein, the term "Area Under the Curve" or "AUC" refers to the overall amount of drug in the bloodstream after a dose. It is calculated as the integral of the plasma drug concentration after the drug is administered. AUC is obtained through collecting blood samples a multiple time points after administering a dose of a composition until a time where the amount of composition in the plasma is negligible.

The term "$C_{max}$" refers to the peak plasma concentration of a composition after administration of the composition.

As used herein, the term "dose-proportional" describes a quantity which has a linear relationship with the amount of a composition administered to a patient, i.e., the magnitude of increase or decrease of a quantity dependent on dosage is about the same as the dosage. For example, if a dosage increase of about 2-fold correlates with an AUC increase of about 2-fold, then the AUC is dose-proportional.

As used herein, the term "plasma" refers to the fluid portion of the blood in which particulate components, e.g. ALN-VSP02 composition, are suspended. It can be obtained by sedimentation or centrifugation of the blood. Plasma represents approximately 50% of the total volume of blood and contains glucose, proteins, amino acids, and other nutritive materials; urea and other excretory products; and hormones, enzymes, vitamins, minerals, etc.

The term "blood plasma concentration" or "plasma concentration" refers to the concentration of a composition, such as ALN-VSP02 or either of the dsRNA of ALN-VSP02, in the plasma component of blood of a subject or patient population. It is understood that the plasma concentration of a composition, such as ALN-VSP02, may vary significantly between subjects, due to variability with respect to metabolism and/or possible interactions with other therapeutic agents.

II. Double-Stranded Ribonucleic Acid (DSRNA)

As described in more detail below, the invention provides double-stranded ribonucleic acid (dsRNA) molecules for inhibiting the expression of the Eg5 and/or VEGF gene in a cell or mammal, and methods of treatment using the dsRNA. The dsRNA comprises an antisense strand comprising a region of complementarity which is complementary to at least a part of an mRNA formed in the expression of the Eg5 and/or VEGF gene, and wherein the region of complementarity is less than 30 nucleotides in length, generally 19-24 nucleotides in length, and wherein said dsRNA, upon contact with a cell expressing said Eg5 and/or VEGF gene, inhibits the expression of said Eg5 and/or VEGF gene.

ALN-VSP02 is a lipid formulated composition that includes two dsRNA, one targeting Eg5/KSP and one targeting VEGF. The sequences of two dsRNAs are as follows:

| Duplex ID | Target | Sense (5' to 3') | Antisense (5' to 3') |
|---|---|---|---|
| AD12115 | Eg5/KSP | ucGAGAAucuAAAcuAAcuTsT (SEQ ID NO: 1) | AGUuAGUUuAGAUUCUCGATsT (SEQ ID NO: 2) |
| AD3133 | VEGF | GcAcAuAGGAGAGAuGAGCUsU (SEQ ID NO: 3) | AAGCUcAUCUCUCCuAuGuGCusG (SEQ ID NO: 4) |

Key: A, G, C, U-ribonucleotides; c, u-2'-O-Me ribonucleotides; s-phosphorothioate.

The dsRNA can be synthesized by standard methods known in the art as further discussed below, e.g., by use of an automated DNA synthesizer, such as are commercially available from, for example, Biosearch, Applied Biosystems, Inc. Additional synthesis methods are described below.

Additional siRNA, e.g., dsRNA targeting Eg5 and/or VEGF are also contemplated. Sequences of siRNA targeting VEGF, including AD-3133, are described in U.S. patent application Ser. No. 11/078,073 filed Mar. 11, 2005 (US Patent publication no 2006-0094032) and US continuation-in-part patent application Ser. No. 12/754,110, filed Jan. 25, 2006 (US patent application publication no. 2006-0223770). Sequences of siRNA targeting Eg5/KSP including AD-12115 are described in U.S. patent application Ser. No. 11/694,215 filed Mar. 30, 2007 (now U.S. Pat. No. 7,718,629). The contents of these applications are incorporated by reference for all purposes. In particular, the sequences of the siRNA disclosed in these applications, e.g., Tables 1 and 2, are incorporated by reference for all purposes.

Additional dsRNA can be designed and described as follows.

The dsRNA comprises two strands that are sufficiently complementary to hybridize to form a duplex structure. One strand of the dsRNA (the antisense strand) comprises a region of complementarity that is substantially complementary, and generally fully complementary, to a target sequence, derived from the sequence of an mRNA formed during the expression of the Eg5 and/or VEGF gene, the other strand (the sense strand) comprises a region which is complementary to the antisense strand, such that the two strands hybridize and form a duplex structure when combined under suitable conditions. Generally, the duplex structure is between 15 and 30, more generally between 18 and 25, yet more generally between 19 and 24, and most generally between 19 and 21 base pairs in length. In other embodiments the duplex structure is 25-30 base pairs in length.

In one embodiment the duplex is 19 base pairs in length. In another embodiment the duplex is 21 base pairs in length. When two different siRNAs are used in combination, the duplex lengths can be identical or can differ. For example, a composition can include a first dsRNA targeted to Eg5 with a duplex length of 19 base pairs and a second dsRNA targeted to VEGF with a duplex length of 21 base pairs.

Similarly, the region of complementarity to the target sequence is between 15 and 30, more generally between 18 and 25, yet more generally between 19 and 24, and most generally between 19 and 21 nucleotides in length. In other embodiments the region of complementarity is 25-30 nucleotides in length. In one embodiment, the region of complementarity is 15, 16, 17, 18, 19, 20, 21, 22, 23, 24, or 24 nucleotides in length.

In one embodiment the region of complementarity is 19 nucleotides in length. In another embodiment the region of complementarity is 21 nucleotides in length. When two different siRNAs are used in combination, the region of complementarity can be identical or can differ. For example, a composition can include a first dsRNA targeted to Eg5 with a region of complementarity of 19 nucleotides and a second dsRNA targeted to VEGF with a region of complementarity of 21 nucleotides.

Each strand of the dsRNA of invention is generally between 15 and 30, or between 18 and 25, or 18, 19, 20, 21, 22, 23, or 24 nucleotides in length. In other embodiments, each is strand is 25-30 base pairs in length. Each strand of the duplex can be the same length or of different lengths. When two different siRNAs are used in combination, the lengths of each strand of each siRNA can be identical or can differ. For example, a composition can include a dsRNA targeted to Eg5 with a sense strand of 21 nucleotides and an antisense strand of 21 nucleotides, and a second dsRNA targeted to VEGF with a sense strand of 21 nucleotides and an antisense strand of 23 nucleotides.

The dsRNA of the invention can include one or more single-stranded overhang(s) of one or more nucleotides. In one embodiment, at least one end of the dsRNA has a single-stranded nucleotide overhang of 1 to 4, generally 1 or 2 nucleotides. In another embodiment, the antisense strand of the dsRNA has 1-10 nucleotides overhangs each at the 3' end and the 5' end over the sense strand. In further embodiments, the sense strand of the dsRNA has 1-10 nucleotides overhangs each at the 3' end and the 5' end over the antisense strand.

A dsRNAs having at least one nucleotide overhang can have unexpectedly superior inhibitory properties than the blunt-ended counterpart. In some embodiments the presence of only one nucleotide overhang strengthens the interference activity of the dsRNA, without affecting its overall stability. A dsRNA having only one overhang has proven particularly stable and effective in vivo, as well as in a variety of cells, cell culture mediums, blood, and serum. Generally, the single-stranded overhang is located at the 3'-terminal end of the antisense strand or, alternatively, at the 3'-terminal end of the sense strand. The dsRNA can also have a blunt end, generally located at the 5'-end of the antisense strand. Such dsRNAs can have improved stability and inhibitory activity, thus allowing administration at low dosages, i.e., less than 5 mg/kg body weight of the recipient per day. Generally, the antisense strand of the dsRNA has a nucleotide overhang at the 3'-end, and the 5'-end is blunt. In another embodiment, one or more of the nucleotides in the overhang is replaced with a nucleoside thiophosphate.

As described in more detail herein, the composition of the invention includes a first dsRNA targeting Eg5 and a second dsRNA targeting VEGF. The first and second dsRNA can have the same overhang architecture, e.g., number of nucleotide overhangs on each strand, or each dsRNA can have a different architecture. In one embodiment, the first dsRNA targeting Eg5 includes a 2 nucleotide overhang at the 3' end of each strand and the second dsRNA targeting VEGF includes a 2 nucleotide overhang on the 3' end of the antisense strand and a blunt end at the 5' end of the antisense strand (e.g., the 3' end of the sense strand).

The skilled person is well aware that dsRNAs comprising a duplex structure of between 20 and 23, but specifically 21, base pairs have been hailed as particularly effective in inducing RNA interference (Elbashir et al., EMBO 2001, 20:6877-6888). However, others have found that shorter or longer dsRNAs can be effective as well It can be reasonably expected that shorter dsRNAs comprising one of the sequences of ALN-VSP02 minus only a few nucleotides on one or both ends may be similarly effective as compared to the dsRNAs described above. Hence, dsRNAs comprising a partial sequence of at least 15, 16, 17, 18, 19, 20, or more contiguous nucleotides from one of the sequences of ALN-VSP02, and differing in their ability to inhibit the expression of the Eg5 and/or VEGF gene in am assay as described herein by not more than 5, 10, 15, 20, 25, or 30% inhibition from a dsRNA comprising the full sequence, are contemplated by the invention. Further dsRNAs that cleave within the target sequences of ALN-VSP02 can readily be made using the ALN-VSP02 sequences and the target sequence provided.

In addition, ALN-VSP02 identifies a site in the Eg5 mRNA and a site in the VEGF gene that is susceptible to RNAi based cleavage. As such the present invention further includes RNAi agents, e.g., dsRNA, that target within the sequence targeted by ALN-VSP02. As used herein a second RNAi agent is said to target within the sequence of a first RNAi agent if the second RNAi agent cleaves the message anywhere within the mRNA that is complementary to the antisense strand of the first RNAi agent. Such a second agent will generally consist of at least 15 contiguous nucleotides from one of the sequences of ALN-VSP02 to additional nucleotide sequences taken from the region contiguous to the selected sequence in the Eg5/KSP and/or VEGF gene.

The dsRNA of the invention can contain one or more mismatches to the target sequence. In a preferred embodiment, the dsRNA of the invention contains no more than 3 mismatches. If the antisense strand of the dsRNA contains mismatches to a target sequence, it is preferable that the area of mismatch not be located in the center of the region of complementarity. If the antisense strand of the dsRNA contains mismatches to the target sequence, it is preferable that the mismatch be restricted to 5 nucleotides from either end, for example 5, 4, 3, 2, or 1 nucleotide from either the 5' or 3' end of the region of complementarity. For example, for a 23 nucleotide dsRNA strand which is complementary to a region of the Eg5 gene, the dsRNA generally does not contain any mismatch within the central 13 nucleotides. The methods described within the invention can be used to determine whether a dsRNA containing a mismatch to a target sequence is effective in inhibiting the expression of the Eg5/KSP and/or VEGF gene. Consideration of the efficacy of dsRNAs with mismatches in inhibiting expression of the Eg5/KSP and/or VEGF gene is important, especially if the particular region of complementarity in the Eg5/KSP and/or VEGF gene is known to have polymorphic sequence variation within the population.

Modifications

The sequences of ALN-VSP02 include chemical modifications. In other embodiments, the Eg5/KSP and/or VEGF targeting dsRNA used in the methods include the same primary sequences as ALN-VSP02, but either no modifications, a subset of the modifications of the sequences of ALN-VSP02, and/or additional modifications. Additional dsRNA targeting Eg5/KSP and/or VEGF with sequences found in the patent applications cited herein can be used in the described methods. These dsRNA can be chemically modified.

In some embodiments, the dsRNA is further chemically modified to enhance stability. The nucleic acids of the invention may be synthesized and/or modified by methods well established in the art, such as those described in "Current protocols in nucleic acid chemistry", Beaucage, S. L. et al. (Edrs.), John Wiley & Sons, Inc., New York, N.Y., USA, which is hereby incorporated herein by reference. Specific examples of preferred dsRNA compounds useful in this invention include dsRNAs containing modified backbones or no natural internucleoside linkages. As defined in this specification, dsRNAs having modified backbones include those that retain a phosphorus atom in the backbone and those that do not have a phosphorus atom in the backbone. For the purposes of this specification, and as sometimes referenced in the art, modified dsRNAs that do not have a phosphorus atom in their internucleoside backbone can also be considered to be oligonucleosides.

Preferred modified dsRNA backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; and 5,625,050, each of which is herein incorporated by reference Preferred modified dsRNA backbones that do not include a phosphorus atom therein have backbones that are formed by short chain alkyl or cycloalkyl internucleoside linkages, mixed heteroatoms and alkyl or cycloalkyl internucleoside linkages, or ore or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, each of which is herein incorporated by reference.

In other preferred dsRNA mimetics, both the sugar and the internucleoside linkage, i.e., the backbone, of the nucleotide units are replaced with novel groups. The base units are maintained for hybridization with an appropriate nucleic acid target compound. One such oligomeric compound, an dsRNA mimetic that has been shown to have excellent hybridization properties, is referred to as a peptide nucleic acid (PNA). In PNA compounds, the sugar backbone of an dsRNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

Most preferred embodiments of the invention are dsRNAs with phosphorothioate backbones and oligonucleosides with heteroatom backbones, and in particular —$CH_2$—NH—$CH_2$—, —$CH_2$—N($CH_3$)—O—$CH_2$—[known as a methylene (methylimino) or MMI backbone], —$CH_2$—O—N($CH_3$)—$CH_2$—, —$CH_2$—N($CH_3$)—N($CH_3$)—$CH_2$— and —N($CH_3$)—$CH_2$—$CH_2$— [wherein the native phosphodiester backbone is represented as —O—P—O—$CH_2$—] of the above-referenced U.S. Pat. No. 5,489,677, and the amide backbones of the above-referenced U.S. Pat. No. 5,602,240. Also preferred are dsRNAs having morpholino backbone structures of the above-referenced U.S. Pat. No. 5,034,506.

Modified dsRNAs may also contain one or more substituted sugar moieties. Preferred dsRNAs comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_3$, O($CH_2$)$_n$NH$_2$, O($CH_2$)$_n$$CH_3$, O($CH_2$)$_n$ONH$_2$, and O($CH_2$)$_n$ON[($CH_2$)$_n$$CH_3$)]$_2$, where n and m are from 1 to about 10. Other preferred dsRNAs comprise one of the following at the 2' position: $C_1$ to $C_{10}$ lower alkyl, substituted lower alkyl, alkaryl, aralkyl, O-alkaryl or O-aralkyl, SH, S$CH_3$, OCN, Cl, Br, CN, $CF_3$, OC$F_3$, SO$CH_3$, SO$_2$$CH_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an dsRNA, or a group for improving the pharmacodynamic properties of an dsRNA, and other substituents having similar properties. A preferred modification includes 2'-methoxyethoxy (2'-O—CH$_2$CH$_2$OCH$_3$, also known as 2'-O-(2-methoxyethyl) or 2'-MOE) (Martin et al., Helv. Chim. Acta, 1995, 78, 486-504) i.e., an alkoxy-alkoxy group. A further preferred modification includes 2'-dimethylaminooxyethoxy, i.e., a O(CH$_2$)$_2$ON (CH$_3$)$_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—CH$_2$—O—CH$_2$—N(CH$_2$)$_2$, also described in examples herein below.

Other preferred modifications include 2'-methoxy (2'-OCH$_3$), 2'-aminopropoxy (2'-OCH$_2$CH$_2$CH$_2$NH$_2$) and 2'-fluoro (2'-F). Similar modifications may also be made at other positions on the dsRNA, particularly the 3' position of the sugar on the 3' terminal nucleotide or in 2'-5' linked dsRNAs and the 5' position of 5' terminal nucleotide. DsRNAs may also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application, and each of which is herein incorporated by reference in its entirety.

The dsRNAs may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosine's, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687,808, those disclosed in The Concise Encyclopedia Of Polymer Science And Engineering, pages 858-859, Kroschwitz, J. L, ed. John Wiley & Sons, 1990, these disclosed by Englisch et al., Angewandte Chemie, International Edition, 1991, 30, 613, and those disclosed by Sanghvi, Y S., Chapter 15, DsRNA Research and Applications, pages 289-302, Crooke, S. T. and Lebleu, B., Ed., CRC Press, 1993. Certain of these nucleobases are particularly useful for increasing the binding affinity of the oligomeric compounds of the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., DsRNA Research and Applications, CRC Press, Boca Raton, 1993, pp. 276-278) and are presently preferred base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,30; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; and 5,681,941, each of which is herein incorporated by reference, and U.S. Pat. No. 5,750,692, also herein incorporated by reference.

Conjugates

Another modification of the dsRNAs of the invention involves chemically linking to the dsRNA one or more moieties or conjugates which enhance the activity, cellular distribution or cellular uptake of the dsRNA. Such moieties include but are not limited to lipid moieties such as a cholesterol moiety (Letsinger et al., Proc. Natl. Acid. Sci. USA, 199, 86, 6553-6556), cholic acid (Manoharan et al., Biorg. Med. Chem. Let., 1994 4 1053-1060), a thioether, e.g., beryl-5-tritylthiol (Manoharan et al., Ann N.Y. Acad. Sci., 1992, 660, 306-309; Manoharan et al., Biorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J, 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-Hphosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim Biophys. Acta, 1995, 1264, 229-237), or an octadecylamine or hexylamino-carbonyloxycholesterol moiety (Crooke et al., J. Pharmacol. Exp. Ther., 1996, 277, 923-937).

Representative U.S. patents that teach the preparation of such dsRNA conjugates include, but are not limited to, U.S. Pat. Nos. 4,828,979; 4,948,882; 5,218,105; 5,525,465; 5,541, 313; 5,545,730; 5,552,538; 5,578,717, 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

It is not necessary for all positions in a given compound to be uniformly modified, and in fact more than one of the aforementioned modifications may be incorporated in a single compound or even at a single nucleoside within an dsRNA. The present invention also includes dsRNA compounds which are chimeric compounds. "Chimeric" dsRNA compounds or "chimeras," in the context of this invention, are dsRNA compounds, particularly dsRNAs, which contain two or more chemically distinct regions, each made up of at least one monomer unit, i.e., a nucleotide in the case of an dsRNA compound. These dsRNAs typically contain at least one region wherein the dsRNA is modified so as to confer upon the dsRNA increased resistance to nuclease degradation, increased cellular uptake, and/or increased binding affinity for the target nucleic acid. An additional region of the dsRNA may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of dsRNA inhibition of gene expression. Consequently, comparable results can often be obtained with shorter dsRNAs when chimeric dsRNAs are used, compared to phosphorothioate deoxy dsRNAs hybridizing to the same target region. Cleavage of the RNA target can be routinely detected by gel electrophoresis and, if necessary, associated nucleic acid hybridization techniques known in the art.

In certain instances, the dsRNA may be modified by a non-ligand group. A number of non-ligand molecules have been conjugated to dsRNAs in order to enhance the activity, cellular distribution or cellular uptake of the dsRNA, and procedures for performing such conjugations are available in the scientific literature. Such non-ligand moieties have included lipid moieties, such as cholesterol (Letsinger et al., Proc. Natl. Acad. Sci. USA, 1989, 86:6553), cholic acid (Manoharan et al., Bioorg. Med. Chem. Lett., 1994, 4:1053), a thioether, e.g., hexyl-5-tritylthiol (Manoharan et al., Ann. N.Y. Acad. Sci., 1992, 660:306; Manoharan et al., Bioorg. Med. Chem. Let., 1993, 3:2765), a thiocholesterol (Oberhauser et al., Nucl. Acids Res., 1992, 20:533), an aliphatic chain, e.g., dodecandiol or undecyl residues (Saison-Behmoaras et al., EMBO J., 1991, 10:111; Kabanov et al., FEBS Lett., 1990, 259:327; Svinarchuk et al., Biochimie, 1993, 75:49), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36:3651; Shea et al., Nucl. Acids Res., 1990, 18:3777), a polyamine or a polyethylene glycol chain (Manoharan et al., Nucleosides & Nucleotides, 1995, 14:969), or adamantane acetic acid (Manoharan et al., Tetrahedron Lett., 1995, 36:3651), a palmityl moiety (Mishra et al., Biochim. Biophys. Acta, 1995, 1264:229), or an octadecylamine or hexylamino-carbonyl-oxycholesterol moiety (Crooke et al., J. Pharmacol. Exp. Ther., 1996, 277:923). Representative United States patents that teach the preparation of such dsRNA conjugates have been listed above. Typical conjugation protocols involve the synthesis of dsRNAs bearing an aminolinker at one or more positions of the sequence. The amino group is then reacted with the molecule being conjugated using appropriate coupling or activating reagents. The conjugation reaction may be performed either with the dsRNA still bound to the solid support or following cleavage of the dsRNA in solution phase. Purification of the dsRNA conjugate by HPLC typically affords the pure conjugate.

In some cases, a ligand can be multifunctional and/or a dsRNA can be conjugated to more than one ligand. For example, the dsRNA can be conjugated to one ligand for improved uptake and to a second ligand for improved release.

Pharmaceutical Compositions Containing dsRNA

In one embodiment, the invention provides pharmaceutical compositions containing a dsRNA, as described herein, and a pharmaceutically acceptable carrier and methods of administering the same. The pharmaceutical composition containing the dsRNA is useful for treating a disease or disorder associated with the expression or activity of a Eg5/KSP and/or VEGF gene, such as pathological processes mediated by Eg5/KSP and/or VEGF expression, e.g., liver cancer. Such pharmaceutical compositions are formulated based on the mode of delivery.

Dosage

The composition, e.g., ALN-VSP02, is administered in a dosage sufficient to inhibit expression of Eg5/KSP and/or VEGF genes. Unless described otherwise, dosage refers to the dose of total dsRNA. If more than one dsRNA is administered at the same time, dosage refers to the dosage of both dsRNA. For example, ALN-VSP02 includes two different dsRNA; a dosage of ALN-VSP02 refers to the total dosage of both dsRNA.

In general, a suitable dose of dsRNA will be in the range of 0.01 to 200.0 milligrams dsRNA per kilogram body weight of the recipient per day, generally in the range of 1 to 50 mg per kilogram body weight per day. In some embodiments a suitable dose of dsRNA is in the ranges of 0.1 to 2.0 mg/kg.

For example, the dsRNA can be administered at a dosage of 0.1, 0.2, 0.3, 0.4, 0.5, 0.6, 0.7, 0.8, 0.9, 1.0, 1.05, 1.1, 1.15, 1.2, 1.25, 1.3, 1.35, 1.4, 1.45, 1.5, 1.55, 1.6, 1.65, 1.7, 1.75, 1.8, 1.85, 1.9, 1.95, or 2.0 mg/kg.

The dosage can be 0.1, 0.2, 0.3, 0.4, 0.7, 1.0, 1.25, 1.5, 1.7, 2.0, 3.0, and 6.0 mg/kg.

The dosage can be 0.1, 0.2, 0.3, 0.4, 0.7, 1.25, 1.5, 1.7, and 6.0 mg/kg.

In one embodiment the dosage is at least 0.4 mg/kg. In another embodiment the dosage is at least 0.7 mg/kg.

In some embodiments, the method includes administering the composition, e.g., ALN-VSP02, once every two weeks. The course of administration can be 2 weeks, 4 weeks, 6 weeks, 8 weeks, 10 weeks, 12, weeks, 14 weeks, or longer. The patient can receive 1-20, or 1-10, or 1-5 doses. the patient can receive 1, 2, 3, 4, 5, 6, 7, 8, 9, or 10 or more doses.

In one embodiment, the composition is administered in a single dose every other week for four weeks for a total of two doses. In another embodiment, the composition is administered in a single dose every other week for eight weeks for a total of four doses.

The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual dsRNAs encompassed by the invention can be made using conventional methodologies or on the basis of in vivo testing using an appropriate animal model, as described elsewhere herein.

Administration

The compositions of the present invention may be administered in a number of ways depending upon whether local or systemic treatment is desired and upon the area to be treated. Administration may be topical, pulmonary, e.g., by inhalation or insufflation of powders or aerosols, including by nebulizer; intratracheal, intranasal, epidermal and transdermal, and subdermal, oral or parenteral, e.g., subcutaneous.

In one embodiment, the composition, e.g., ALN-VSP02, is administered systemically via parental means. Parenteral administration includes intravenous (IV), intra-arterial, subcutaneous, intraperitoneal or intramuscular injection or infusion; or intracranial, e.g., intraparenchymal, intrathecal or intraventricular, administration. For example, ALN-VSP02 can be administered intravenously to a patient.

Intravenous infusion or injection can be administered for 15 minutes. Intravenous infusion or injection can also be administered over the course of 1-5 minutes, 5-10 minutes, 10-20 minutes, 20-30 minutes, or longer.

In certain instances, administration of siRNA treatment via IV infusion can cause an acute adverse reaction. Accordingly, in one embodiment of the invention, the duration of the IV infusion is extended if it is observed or predicted that a patient had or will have an acute adverse reaction to an siRNA treatment. In one aspect, the duration of IV infusion is extended to more than 15, 30, 45, or 60 minutes. In another aspect, the duration of IV infusion is extended to more than 1, 2, 3, or 4 hours. In a particular embodiment, the duration of IV infusion is extended to up to 3 hours in the event of an acute infusion reaction. For such, a dsRNA molecule can be formulated into compositions such as sterile and non-sterile aqueous solutions, non-aqueous solutions in common solvents such as alcohols, or solutions in liquid or solid oil bases. Such solutions also can contain buffers, diluents, and other suitable additives. For parenteral, intrathecal, or intraventricular administration, a dsRNA molecule can be formulated into compositions such as sterile aqueous solutions, which also can contain buffers, diluents, and other suitable additives (e.g., penetration enhancers, carrier compounds, and other pharmaceutically acceptable carriers). Formulations are described in more detail herein.

The composition, e.g., ALN-VSP02, can be delivered in a manner to target a particular tissue, such as the liver (e.g., the hepatocytes of the liver).

It is well known to one of skill in the art that, in certain instances, siRNA treatment can generate an off-target global or acute inflammatory response, leading to possible unwanted inflammation, toxic side effects, and discomfort. Several compounds are capable of mitigating an unwanted inflammatory or pain response when provided in advance of siRNA treatment.

Accordingly, in some embodiments of the invention, the administration of the composition, e.g., ALN-VSP02, is preceded by the administration of at least one compound capable of mitigating an inflammatory response. In one embodiment the compound selected from the group consisting of dexamethasone, H1 and H2 blockers, and acetaminophen.

The administration of a compound for mitigating unwanted off-target effects can occur simultaneously to, just before, or several minutes before administration of an siRNA treatment. In one embodiment, administration of a compound to mitigate unwanted off-target effects occurs more than about 10, 15, 30, 45, or 60 minutes prior to administration of an siRNA treatment.

Formulations

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids. In one aspect are formulations that target the liver when treating hepatic disorders such as hyperlipidemia.

In addition, dsRNA that target the EG5/KSP and/or VEGF gene can be formulated into compositions containing the dsRNA admixed, encapsulated, conjugated, or otherwise associated with other molecules, molecular structures, or mixtures of nucleic acids. For example, a composition containing one or more dsRNA agents that target the Eg5/KSP and/or VEGF gene can contain other therapeutic agents, such as other cancer therapeutics or one or more dsRNA compounds that target non-EG5/KSP AND/OR VEGF genes.

Oral, Parenteral, Topical, and Biologic Formulations

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. In some embodiments, oral formulations are those in which dsRNAs featured in the invention are administered in conjunction with one or more penetration enhancers surfactants and chelators. Suitable surfactants include fatty acids and/or esters or salts thereof, bile acids and/or salts thereof. Suitable bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate and sodium glycodihydrofusidate. Suitable fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g., sodium). In some embodiments, combinations of penetration enhancers are used, for example, fatty acids/salts in combination with bile acids/salts. One exemplary combination is the sodium salt of lauric acid, capric acid and UDCA. Further penetration enhancers include polyoxyethylene-9-lauryl ether, polyoxyethylene-20-cetyl ether. dsRNAs featured in the invention may be delivered orally, in granular form including sprayed dried particles, or complexed to form micro or nanoparticles. dsRNA complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Suitable complexing agents include chitosan, N-trimethylchitosan, poly-L-lysine, polyhistidine, polyornithine, polyspermines, protamine, polyvinylpyridine, polythiodiethylaminomethylethylene P(TDAE), polyaminostyrene (e.g., p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for dsRNAs and their preparation are described in detail in U.S. Pat. No. 6,887,906, U.S. Patent Publication. No. 20030027780, and U.S. Pat. No. 6,747,014, each of which is incorporated herein by reference.

Compositions and formulations for parenteral, intraparenchymal (into the brain), intrathecal, intraventricular or intrahepatic administration may include sterile aqueous solutions which may also contain buffers, diluents and other suitable additives such as, but not limited to, penetration enhancers, carrier compounds and other pharmaceutically acceptable carriers or excipients.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Suitable topical formulations include those in which the dsRNAs featured in the invention are in admixture with a topical delivery agent such as lipids, liposomes, fatty acids, fatty acid esters, steroids, chelating agents and surfactants. Suitable lipids and liposomes include neutral (e.g., dioleoylphosphatidyl DOPE ethanolamine, dimyristoylphosphatidyl choline DMPC, distearolyphosphatidyl choline) negative (e.g., dimyristoylphosphatidyl glycerol DMPG) and cationic (e.g., dioleoyltetramethylaminopropyl DOTAP and dioleoylphosphatidyl ethanolamine DOTMA). dsRNAs featured in the invention may be encapsulated within liposomes or may form complexes thereto, in particular to cationic liposomes. Alternatively, dsRNAs may be complexed to lipids, in particular to cationic lipids. Suitable fatty acids and esters include but are not limited to arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (e.g., isopropylmyristate IPM), monoglyceride, diglyceride or pharmaceutically acceptable salt thereof. Topical formulations are described in detail in U.S. Pat. No. 6,747,014, which is incorporated herein by reference.

In addition, dsRNA molecules can be administered to a mammal as biologic or abiologic means as described in, for example, U.S. Pat. No. 6,271,359. Abiologic delivery can be accomplished by a variety of methods including, without limitation, (1) loading liposomes with a dsRNA acid molecule provided herein and (2) complexing a dsRNA molecule with lipids or liposomes to form nucleic acid-lipid or nucleic acid-liposome complexes. The liposome can be composed of cationic and neutral lipids commonly used to transfect cells in vitro. Cationic lipids can complex (e.g., charge-associate) with negatively charged nucleic acids to form liposomes. Examples of cationic liposomes include, without limitation, lipofectin, lipofectamine, lipofectace, and DOTAP. Procedures for forming liposomes are well known in the art. Liposome compositions can be formed, for example, from phosphatidylcholine, dimyristoyl phosphatidylcholine, dipalmitoyl phosphatidylcholine, dimyristoyl phosphatidylglycerol, or dioleoyl phosphatidylethanolamine. Numerous lipophilic agents are commercially available, including Lipofectin™ (Invitrogen/Life Technologies, Carlsbad, Calif.) and Effectene™ (Qiagen, Valencia, Calif.). In addition, systemic delivery methods can be optimized using commercially available cationic lipids such as DDAB or DOTAP, each of which can be mixed with a neutral lipid such as DOPE or cholesterol. In some cases, liposomes such as those described by Templeton et al. (Nature Biotechnology, 15: 647-652 (1997)) can be used. In other embodiments, polycations such as polyethyleneimine can be used to achieve delivery in vivo and ex vivo (Boletta et al., J. Am. Soc. Nephrol. 7: 1728 (1996)). Additional information regarding the use of liposomes to deliver nucleic acids can be found in U.S. Pat. No. 6,271,359, PCT Publication WO 96/40964 and Morrissey, D. et al. 2005. Nat. Biotechnol. 23(8):1002-7.

Biologic delivery can be accomplished by a variety of methods including, without limitation, the use of viral vectors. For example, viral vectors (e.g., adenovirus and herpes virus vectors) can be used to deliver dsRNA molecules to liver cells. Standard molecular biology techniques can be used to introduce one or more of the dsRNAs provided herein into one of the many different viral vectors previously developed to deliver nucleic acid to cells. These resulting viral vectors can be used to deliver the one or more dsRNAs to cells by, for example, infection.

Liposomal Formulations

The compositions used in the invention can be in a liposome formulation. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include: liposomes obtained from natural phospholipids are biocompatible and biodegradable; liposomes can incorporate a wide range of water and lipid soluble drugs; and liposomes can protect encapsulated drugs in their internal compartments from metabolism and degradation (Rosoff, in Pharmaceutical Dosage Forms, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes and as the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., Biochem. Biophys. Res. Commun., 1987, 147, 980-985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., Journal of Controlled Release, 1992, 19, 269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g., as a solution or as an emulsion) were ineffective (Weiner et al., Journal of Drug Targeting, 1992, 2, 405-410). Further, an additional study tested the efficacy of interferon administered as part of a liposomal formulation to the administration of interferon using an aqueous system, and concluded that the liposomal formulation was superior to aqueous administration (du Plessis et al., Antiviral Research, 1992, 18, 259-265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/po-lyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al., S.T.P. Pharma. Sci., 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., FEBS Letters, 1987, 223, 42; Wu et al., Cancer Research, 1993, 53, 3765).

Various liposomes comprising one or more glycolipids are known in the art. Papahadjopoulos et al. (Ann. N.Y. Acad. Sci., 1987, 507, 64) reported the ability of monosialoganglioside $G_{M1}$, galactocerebroside sulfate and phosphatidylinositol to improve blood half-lives of liposomes. These findings were expounded upon by Gabizon et al. (Proc. Natl. Acad. Sci. U.S.A., 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphat-idylcholine are disclosed in WO 97/13499 (Lim et al.).

Many liposomes comprising lipids derivatized with one or more hydrophilic polymers, and methods of preparation thereof, are known in the art. Sunamoto et al. (Bull. Chem. Soc. Jpn., 1980, 53, 2778) described liposomes comprising a nonionic detergent, $2C_{1215G}$, that contains a PEG moiety. Illum et al. (FEBS Lett., 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (FEBS Lett., 1990, 268, 235) described experiments demonstrating that liposomes comprising phosphatidylethanolamine (PE) derivatized with PEG or PEG stearate have significant increases in blood circulation half-lives. Blume et al. (Biochimica et Biophysica Acta, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1-20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al). U.S. Pat. No. 5,540,935 (Miyazaki et al.) and U.S. Pat. No. 5,556,948 (Tagawa et al.) describe PEG-containing liposomes that can be further derivatized with functional moieties on their surfaces.

A number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include a dsRNA. U.S. Pat. No. 5,665,710 to Rahman et al. describes certain methods of encapsulating oligodeoxynucleotides in liposomes. WO 97/04787 to Love et al. discloses liposomes comprising dsRNAs targeted to the raf gene.

Transfersomes are yet another type of liposomes and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g., they are self-optimizing (adaptive to the shape of pores in the skin), self-repairing, frequently reach their targets without fragmenting, and often self-loading. To make transfersomes, it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in Pharmaceutical Dosage Forms, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in Pharmaceutical Dosage Forms, Marcel Dekker, Inc., New York, N.Y., 1988, p. 285).

Nucleic Acid Lipid Particles

In one embodiment, a dsRNA featured in the invention is fully encapsulated in the lipid formulation, e.g., to form a nucleic acid lipid particle. Nucleic acid-lipid particles typically contain a cationic lipid, a non-cationic lipid, a sterol, and a lipid that prevents aggregation of the particle (e.g., a PEG-lipid conjugate). Nucleic acid-lipid particles are extremely useful for systemic applications, as they exhibit extended circulation lifetimes following intravenous (i.v.) injection and accumulate at distal sites (e.g., sites physically separated from the administration site). In addition, the nucleic acids when present in the nucleic acid-lipid particles of the present invention are resistant in aqueous solution to degradation with a nuclease. Nucleic acid-lipid particles and their method of preparation are disclosed in, e.g., U.S. Pat. Nos. 5,976,567; 5,981,501; 6,534,484; 6,586,410; 6,815,432; and PCT Publication No. WO 96/40964.

Nucleic acid-lipid particles can further include one or more additional lipids and/or other components such as cholesterol. Other lipids may be included in the liposome compositions for a variety of purposes, such as to prevent lipid oxidation or to attach ligands onto the liposome surface. Any of a number of lipids may be present, including amphipathic, neutral, cationic, and anionic lipids. Such lipids can be used alone or in combination. Specific examples of additional lipid components that may be present are described herein.

Additional components that may be present in a nucleic acid-lipid particle include bilayer stabilizing components such as polyamide oligomers (see, e.g., U.S. Pat. No. 6,320, 017), peptides, proteins, detergents, lipid-derivatives, such as PEG coupled to phosphatidylethanolamine and PEG conjugated to ceramides (see, U.S. Patent No. 5,885,613).

A nucleic acid-lipid particle can include one or more of a second amino lipid or cationic lipid, a neutral lipid, a sterol, and a lipid selected to reduce aggregation of lipid particles during formation, which may result from steric stabilization of particles which prevents charge-induced aggregation during formation.

Nucleic acid-lipid particles include, e.g., a SPLP, pSPLP, and SNALP. The term "SNALP" refers to a stable nucleic acid-lipid particle, including SPLP. The term "SPLP" refers to a nucleic acid-lipid particle comprising plasmid DNA encapsulated within a lipid vesicle. SPLPs include "pSPLP," which include an encapsulated condensing agent-nucleic acid complex as set forth in PCT Publication No. WO 00/03683.

The nucleic acid-lipid particles of the present invention typically have a mean diameter of about 50 nm to about 150 nm, more typically about 60 nm to about 130 nm, more typically about 70 nm to about 110 nm, most typically about 70 nm to about 90 nm, or about 50, 60, 70, 80, 90, 100, 110, 120, 130, 140, or about 150 nm such that the particles are substantially nontoxic In one embodiment, the lipid to drug ratio (mass/mass ratio) (e.g., lipid to dsRNA ratio) will be in the range of from about 1:1 to about 50:1, from about 1:1 to about 25:1, from about 3:1 to about 15:1, from about 4:1 to about 10:1, from about 5:1 to about 9:1, or about 6:1 to about 9:1, or about 6:1, 7:1, 8:1, 9:1, 10:1, 11:1, 12:1, or 33:1.

Cationic Lipids

The nucleic acid-lipid particles of the invention typically include a cationic lipid. The cationic lipid may be, for example, N,N-dioleyl-N,N-dimethylammonium chloride (DODAC), N,N-distearyl-N,N-dimethylammonium bromide (DDAB), N-(1-(2,3-dioleoyloxy)propyl)-N,N,N-trimethylammonium chloride (DOTAP), N-(1-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-Dilinoleylcarbamoyloxy-3-dimethylaminopropane (DLin-C-DAP), 1,2-Dilinoleyoxy-3-(dimethylamino)acetoxypropane (DLin-DAC), 1,2-Dilinoleyoxy-3- morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA.Cl), 1,2-Dilinoleoyl-3-trimethylaminopropane chloride salt (DLin-TAP.Cl), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanedio (DOAP), 1,2-Dilinoleyloxo-3-(2-N,N-dimethylamino)ethoxypropane (DLin-EG-DMA), 1,2-Dilinolenyloxy-N,N-dimethylaminopropane (DLinDMA), 2,2-Dilinoleyl-4-dimethylaminomethyl-[1,3]-dioxolane (DLin-K-DMA) or analogs thereof, (3aR,5s,6aS)-N,N-dimethyl-2,2-di((9Z,12Z)-octadeca-9,12-dienyl)tetrahydro-3aH-cyclopenta[d][1,3]dioxol-5-amine (ALNY-100), (6Z,9Z,28Z,31Z)-heptatriaconta-6,9,28,31-tetraen-19-yl 4-(dimethylamino)butanoate (MC3), 1,1'-(2-(4-(24(2-(bis(2-hydroxydodecyl)amino)ethyl)(2-hydroxydodecyl)amino)ethyl)piperazin-1-yl)ethylazanediyl)didodecan-2-ol (C12-200), or a mixture thereof.

Other cationic lipids, which carry a net positive charge at about physiological pH, in addition to those specifically described above, may also be included in lipid particles of the invention. Such cationic lipids include, but are not limited to, N,N-dioleyl-N,N-dimethylammonium chloride ("DODAC"); N-(2,3-dioleyloxy)propyl-N,N—N-triethylammonium chloride ("DOTMA"); N,N-distearyl-N,N-dimethylammonium bromide ("DDAB"); N-(2,3-dioleoyloxy)propyl)-N,N,N-trimethylammonium chloride ("DOTAP"); 1,2-Dioleyloxy-3-trimethylaminopropane chloride salt ("DOTAP.Cl"); 3β-(N—(N',N'-dimethylaminoethane)-carbamoyl)cholesterol ("DC-Chol"), N-(1-(2,3-dioleyloxy)propyl)-N-2-(sperminecarboxamido)ethyl)-N,N-dimethylammonium trifluoracetate ("DOSPA"), dioctadecylamidoglycyl carboxyspermine ("DOGS"), 1,2-dileoyl-sn-3-phosphoethanolamine ("DOPE"), 1,2-dioleoyl-3-dimethylammonium propane ("DODAP"), N,N-dimethyl-2,3-dioleyloxy)propylamine ("DODMA"), and N-(1,2-dimyristyloxyprop-3-yl)-N,N-dimethyl-N-hydroxyethyl ammonium bromide ("DMRIE"). Additionally, a number of commercial preparations of cationic lipids can be used, such as, e.g., LIPOFECTIN (including DOTMA and DOPE, available from GIBCO/BRL), and LIPOFECTAMINE (comprising DOSPA and DOPE, available from GIBCO/BRL). In particular embodiments, a cationic lipid is an amino lipid.

As used herein, the term "amino lipid" is meant to include those lipids having one or two fatty acid or fatty alkyl chains and an amino head group (including an alkylamino or dialkylamino group) that may be protonated to form a cationic lipid at physiological pH.

Other amino lipids would include those having alternative fatty acid groups and other dialkylamino groups, including those in which the alkyl substituents are different (e.g., N-ethyl-N-methylamino-, N-propyl-N-ethylamino- and the like). For those embodiments in which $R^{11}$ and $R^{12}$ are both long chain alkyl or acyl groups, they can be the same or different. In general, amino lipids having less saturated acyl chains are more easily sized, particularly when the complexes must be sized below about 0.3 microns, for purposes of filter sterilization. Amino lipids containing unsaturated fatty acids with carbon chain lengths in the range of $C_{14}$ to $C_{22}$ are preferred. Other scaffolds can also be used to separate the amino group and the fatty acid or fatty alkyl portion of the amino lipid. Suitable scaffolds are known to those of skill in the art.

In certain embodiments, amino or cationic lipids of the invention have at least one protonatable or deprotonatable group, such that the lipid is positively charged at a pH at or below physiological pH (e.g. pH 7.4), and neutral at a second pH, preferably at or above physiological pH. It will, of course, be understood that the addition or removal of protons as a function of pH is an equilibrium process, and that the reference to a charged or a neutral lipid refers to the nature of the predominant species and does not require that all of the lipid be present in the charged or neutral form. Lipids that have more than one protonatable or deprotonatable group, or which are zwitterionic, are not excluded from use in the invention.

In certain embodiments, protonatable lipids according to the invention have a pKa of the protonatable group in the range of about 4 to about 11. Most preferred is pKa of about 4 to about 7, because these lipids will be cationic at a lower pH formulation stage, while particles will be largely (though not completely) surface neutralized at physiological pH around pH 7.4. One of the benefits of this pKa is that at least some nucleic acid associated with the outside surface of the particle will lose its electrostatic interaction at physiological pH and be removed by simple dialysis; thus greatly reducing the particle's susceptibility to clearance.

In one embodiment, the cationic lipid is 1,2-Dilinolenyloxy-N,N-dimethylaminopropane (DLinDMA). Synthesis and preparation of nucleic acid-lipid particles including DLinDMA is described in International application number PCT/CA2009/00496, filed Apr. 15, 2009.

In one embodiment, the cationic lipid XTC (2,2-Dilinoleyl-4-dimethylaminoethyl-[1,3]-dioxolane) is used to prepare nucleic acid-lipid particles. Synthesis of XTC is described in U.S. provisional patent application No. 61/107,998 filed on Oct. 23, 2008, which is herein incorporated by reference.

In another embodiment, the cationic lipid MC3 ((6Z,9Z,28Z,31Z)-heptatriaconta-6,9,28,31-tetraen-19-yl-4-(dimethylamino)butanoate), (e.g., DLin-M-C3-DMA) is used to prepare nucleic acid-lipid particles. Synthesis of MC3 and MC3 comprising formulations are described, e.g., in U.S. Provisional Ser. No. 61/244,834, filed Sep. 22, 2009, and U.S. Provisional Ser. No. 61/185,800, filed Jun. 10, 2009, which are hereby incorporated by reference.

In another embodiment, the cationic lipid ALNY-100 ((3aR,5s,6aS)-N,N-dimethyl-2,2-di((9Z,12Z)-octadeca-9,12-dienyl)tetrahydro-3aH-cyclopenta[d][1,3]dioxol-5-amine) is used to prepare nucleic acid-lipid particles. Synthesis of ALNY-100 is described in International patent application number PCT/US09/63933 filed on Nov. 10, 2009, which is herein incorporated by reference.

In another embodiment, the cationic lipid 1,1'-(2-(4-(2-((2-(bis(2-hydroxydodecyl)amino)ethyl)(2-hydroxydodecyl)amino)ethyl)piperazin-1-yl)ethylazanediyl)didodecan-2-ol (C12-200) is used to prepare nucleic acid lipid particles. C12-200 is also known as Tech G1. Synthesis of C12-200 and formulations using C12-200 are described in International patent application no. PCT/US10/33777 filed May 5, 2010 and in Love et al (Love et al. (2010) PNAS 107(5); 1864-69).

The cationic lipid, e.g., DLinDMA, can comprise from about 20 mol % to about 70 mol % or about 45-65 mol % or about 20, 25, 30, 35, 40, 45, 50, 55, 60, 65, or about 70 mol % of the total lipid present in the particle. In one embodiment the cationic lipid comprises about 57.1 mol % of the total lipid present.

Non-Cationic Lipids

The nucleic acid-lipid particles of the invention can include a non-cationic lipid. The non-cationic lipid may be an anionic lipid or a neutral lipid. Examples include but not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoylphosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, or a mixture thereof.

Anionic lipids suitable for use in lipid particles of the invention include, but are not limited to, phosphatidylglycerol, cardiolipin, diacylphosphatidylserine, diacylphosphatidic acid, N-dodecanoyl phosphatidylethanoloamine, N-succinyl phosphatidylethanolamine, N-glutaryl phosphatidylethanolamine, lysylphosphatidylglycerol, and other anionic modifying groups joined to neutral lipids.

Neutral lipids, when present in the lipid particle, can be any of a number of lipid species which exist either in an uncharged or neutral zwitterionic form at physiological pH. Such lipids include, for example diacylphosphatidylcholine, diacylphosphatidylethanolamine, ceramide, sphingomyelin, dihydrosphingomyelin, cephalin, and cerebrosides. The selection of neutral lipids for use in the particles described herein is generally guided by consideration of, e.g., liposome size and stability of the liposomes in the bloodstream. Preferably, the neutral lipid component is a lipid having two acyl groups, (i.e., diacylphosphatidylcholine and diacylphosphatidylethanolamine). Lipids having a variety of acyl chain groups of varying chain length and degree of saturation are available or may be isolated or synthesized by well-known techniques. In one group of embodiments, lipids containing saturated fatty acids with carbon chain lengths in the range of $C_{14}$ to $C_{22}$ are preferred. In another group of embodiments, lipids with mono- or di-unsaturated fatty acids with carbon chain lengths in the range of $C_{14}$ to $C_{22}$ are used. Additionally, lipids having mixtures of saturated and unsaturated fatty acid chains can be used. Preferably, the neutral lipids used in the invention are DOPE, DSPC, POPC, or any related phosphatidylcholine. The neutral lipids useful in the invention may also be composed of sphingomyelin, dihydrosphingomyeline, or phospholipids with other head groups, such as serine and inositol.

In one embodiment the non-cationic lipid is distearoylphosphatidylcholine (DSPC). In another embodiment the non-cationic lipid is dipalmitoylphosphatidylcholine (DPPC).

The non-cationic lipid, e.g., DPPC, can be from about 5 mol % to about 90 mol %, about 5 mol % to about 10 mol %, about 5, 10, 15, 20, 25, 30, 35, 40, 45, 50, 55, 60, 65, 70, 75, 80, 85, or about 90 mol % of the total lipid present in the particle. In one embodiment, the cationic lipid, e.g., DPPC, comprises 7.1 mol % of the nucleic acid-lipid particle.

Conjugated Lipids

Conjugated lipids can be used in nucleic acid-lipid particle to prevent aggregation, including polyethylene glycol (PEG)-modified lipids, monosialoganglioside Gm1, and polyamide oligomers ("PAO") such as (described in U.S. Pat. No. 6,320,017). Other compounds with uncharged, hydrophilic, steric-barrier moieties, which prevent aggregation during formulation, like PEG, Gm1 or ATTA, can also be coupled to lipids for use as in the methods and compositions of the invention. ATTA-lipids are described, e.g., in U.S. Pat. No. 6,320,017, and PEG-lipid conjugates are described, e.g., in U.S. Pat. Nos. 5,820,873, 5,534,499 and 5,885,613. Typically, the concentration of the lipid component selected to reduce aggregation is about 1 to 15% (by mole percent of lipids).

Specific examples of PEG-modified lipids (or lipid-polyoxyethylene conjugates) that are useful in the invention can have a variety of "anchoring" lipid portions to secure the PEG portion to the surface of the lipid vesicle. Examples of suitable PEG-modified lipids include PEG-modified phosphatidylethanolamine and phosphatidic acid, PEG-ceramide conjugates (e.g., PEG-CerC14 or PEG-CerC20) which are described in co-pending U.S. Ser. No. 08/486,214, incorporated herein by reference, PEG-modified dialkylamines and PEG-modified 1,2-diacyloxypropan-3-amines. Particularly preferred are PEG-modified diacylglycerols and dialkylglycerols.

In embodiments where a sterically-large moiety such as PEG or ATTA are conjugated to a lipid anchor, the selection of the lipid anchor depends on what type of association the conjugate is to have with the lipid particle. It is well known that mePEG (mw2000)-diastearoylphosphatidylethanolamine (PEG-DSPE) will remain associated with a liposome until the particle is cleared from the circulation, possibly a matter of days. Other conjugates, such as PEG-CerC20 have similar staying capacity. PEG-CerC14, however, rapidly exchanges out of the formulation upon exposure to serum, with a $T_{1/2}$ less than 60 mins. in some assays. As illustrated in U.S. patent application Ser. No. 08/486,214, at least three characteristics influence the rate of exchange: length of acyl chain, saturation of acyl chain, and size of the steric-barrier head group. Compounds having suitable variations of these features may be useful for the invention. For some therapeutic applications, it may be preferable for the PEG-modified lipid to be rapidly lost from the nucleic acid-lipid particle in vivo and hence the PEG-modified lipid will possess relatively short lipid anchors. In other therapeutic applications, it may be preferable for the nucleic acid-lipid particle to exhibit a longer plasma circulation lifetime and hence the PEG-modified lipid will possess relatively longer lipid anchors. Exemplary lipid anchors include those having lengths of from about $C_{14}$ to about $C_{22}$, preferably from about $C_{14}$ to about $C_{16}$. In some embodiments, a PEG moiety, for example an mPEG-$NH_2$, has a size of about 1000, 2000, 5000, 10,000, 15,000 or 20,000 daltons.

It should be noted that aggregation preventing compounds do not necessarily require lipid conjugation to function properly. Free PEG or free ATTA in solution may be sufficient to prevent aggregation. If the particles are stable after formulation, the PEG or ATTA can be dialyzed away before administration to a subject.

The conjugated lipid that inhibits aggregation of particles may be, for example, a polyethyleneglycol (PEG)-lipid including, without limitation, a PEG-diacylglycerol (DAG), a PEG-dialkyloxypropyl (DAA), a PEG-phospholipid, a PEG-ceramide (Cer), or a mixture thereof. The PEG-DAA conjugate may be, for example, a PEG-dilauryloxypropyl ($C_{12}$), a PEG-dimyristyloxypropyl ($C_{14}$), a PEG-dipalmityloxypropyl ($C_{16}$), or a PEG-distearyloxypropyl ($C_{18}$). Additional conjugated lipids include polyethylene glycol-didimyristoyl glycerol (C14-PEG or PEG-C14, where PEG has an average molecular weight of 2000 Da) (PEG-DMG); (R)-2,3-bis(octadecyloxy)propyl]-(methoxy poly(ethylene glycol)2000) propylcarbamate) (PEG-DSG); PEG-carbamoyl-1,2-dimyristyloxypropylamine, in which PEG has an average molecular weight of 2000 Da (PEG-cDMA); N-Acetylgalactosamine-((R)-2,3-bis(octadecyloxy)propyl1-(methoxy poly(ethylene glycol)2000)propylcarbamate)) (GalNAc-PEG-DSG); and polyethylene glycol-dipalmitoylglycerol (PEG-DPG).

In one embodiment the conjugated lipid is PEG-DMG or PEG-DSG. In another embodiment the conjugated lipid is PEG-cDMA. In still another embodiment the conjugated lipid is PEG-DPG. Alternatively the conjugated lipid is GalNAc-PEG-DSG.

In some embodiments the conjugated lipid that prevents aggregation of particles is from 0 mol % to about 20 mol % or about 0.5 to about 5.0 mol % or about or about 1.5 mol % or about 2.0 mol % of the total lipid present in the particle. The conjugated lipid can be about 0.5, 1.0, 1.1, 1.2, 1.3, 1.4, 1.5, 1.6, 1.7, 1.8, 1.9, 2.0, 2.5, 3.0, 3.5, 4.0, 4.5, or about 5.0 mol % of the total lipid present in the particle. In one embodiment, the conjugated lipid, e.g., PEG-cDMA, is 1.4 mol %.

The sterol component of the lipid mixture, when present, can be any of those sterols conventionally used in the field of liposome, lipid vesicle or lipid particle preparation. A preferred sterol is cholesterol.

In some embodiments, the nucleic acid-lipid particle further includes a sterol, e.g., cholesterol. The sterol can be about 10 to about 60 mol % or about 25 to about 40 mol % of the nucleic acid-lipid particle. In some embodiment the sterol is about 10, 15, 20, 25, 30, 35, 40, 45, 50, 55, or about 60 mol % of the total lipid present in the article. The sterol, e.g., cholesterol, can be about 34.3 or 34.4 mol % of the total lipid in the particle.

Lipoproteins

In one embodiment, the formulations of the invention further comprise an apolipoprotein. As used herein, the term "apolipoprotein" or "lipoprotein" refers to apolipoproteins known to those of skill in the art and variants and fragments thereof and to apolipoprotein agonists, analogues or fragments thereof described below.

Suitable apolipoproteins include, but are not limited to, ApoA-I, ApoA-II, ApoA-IV, ApoA-V and ApoE, and active polymorphic forms, isoforms, variants and mutants as well as fragments or truncated forms thereof. In certain embodiments, the apolipoprotein is a thiol containing apolipoprotein. "Thiol containing apolipoprotein" refers to an apolipoprotein, variant, fragment or isoform that contains at least one cysteine residue. The most common thiol containing apolipoproteins are ApoA-I Milano (ApoA-$I_M$) and ApoA-I Paris (ApoA-$I_P$) which contain one cysteine residue (Jia et al., 2002, Biochem. Biophys. Res. Comm. 297: 206-13; Bielicki and Oda, 2002, Biochemistry 41: 2089-96). ApoA-II, ApoE2 and ApoE3 are also thiol containing apolipoproteins. Isolated ApoE and/or active fragments and polypeptide analogues thereof, including recombinantly produced forms thereof, are described in U.S. Pat. Nos. 5,672,685; 5,525,472; 5,473,039; 5,182,364; 5,177,189; 5,168,045; 5,116,739; the disclosures of which are herein incorporated by reference. ApoE3 is disclosed in Weisgraber, et al., "Human E apoprotein heterogeneity: cysteine-arginine interchanges in the amino acid sequence of the apo-E isoforms," J. Biol. Chem. (1981) 256: 9077-9083; and Rall, et al., "Structural basis for receptor binding heterogeneity of apolipoprotein E from type III hyperlipoproteinemic subjects," Proc. Nat. Acad. Sci. (1982) 79: 4696-4700. (See also GenBank accession number K00396.)

In certain embodiments, the apolipoprotein can be in its mature form, in its preproapolipoprotein form or in its proapolipoprotein form. Homo- and heterodimers (where feasible) of pro- and mature ApoA-I (Duverger et al., 1996, Arterioscler. Thromb. Vasc. Biol. 16(12):1424-29), ApoA-I Milano (Klon et al., 2000, Biophys. J. 79:(3)1679-87; Franceschini et al., 1985, J. Biol. Chem. 260: 1632-35), ApoA-I Paris (Daum et al., 1999, J. Mol. Med. 77:614-22), ApoA-II (Shelness et al., 1985, J. Biol. Chem. 260(14):8637-46; Shelness et al., 1984, J. Biol. Chem. 259(15):9929-35), ApoA-IV (Duverger et al., 1991, Euro. J. Biochem. 201(2):373-83), and ApoE (McLean et al., 1983, J. Biol. Chem. 258(14):8993-9000) can also be utilized within the scope of the invention.

In certain embodiments, the apolipoprotein can be a fragment, variant or isoform of the apolipoprotein. The term "fragment" refers to any apolipoprotein having an amino acid sequence shorter than that of a native apolipoprotein and which fragment retains the activity of native apolipoprotein, including lipid binding properties. By "variant" is meant substitutions or alterations in the amino acid sequences of the apolipoprotein, which substitutions or alterations, e.g., additions and deletions of amino acid residues, do not abolish the activity of native apolipoprotein, including lipid binding properties. Thus, a variant can comprise a protein or peptide having a substantially identical amino acid sequence to a native apolipoprotein provided herein in which one or more amino acid residues have been conservatively substituted with chemically similar amino acids. Examples of conservative substitutions include the substitution of at least one hydrophobic residue such as isoleucine, valine, leucine or methionine for another. Likewise, the present invention contemplates, for example, the substitution of at least one hydrophilic residue such as, for example, between arginine and lysine, between glutamine and asparagine, and between glycine and serine (see U.S. Pat. Nos. 6,004,925, 6,037,323 and 6,046,166). The term "isoform" refers to a protein having the same, greater or partial function and similar, identical or partial sequence, and may or may not be the product of the same gene and usually tissue specific (see Weisgraber 1990, J. Lipid Res. 31(8):1503-11; Hixson and Powers 1991, J. Lipid Res. 32(9):1529-35; Lackner et al., 1985, J. Biol. Chem. 260(2):703-6; Hoeg et al., 1986, J. Biol. Chem. 261(9):3911-4; Gordon et al., 1984, J. Biol. Chem. 259(1):468-74; Powell et al., 1987, Cell 50(6):831-40; Aviram et al., 1998, Arterioscler. Thromb. Vasc. Biol. 18(10):1617-24; Aviram et al., 1998, J. Clin. Invest. 101(8):1581-90; Billecke et al., 2000, Drug Metab. Dispos. 28(11):1335-42; Draganov et al., 2000, J. Biol. Chem. 275(43):33435-42; Steinmetz and Utermann 1985, J. Biol. Chem. 260(4):2258-64; Widler et al., 1980, J. Biol. Chem. 255(21):10464-71; Dyer et al., 1995, J. Lipid Res. 36(1):80-8; Sacre et al., 2003, FEBS Lett. 540(1-3):181-7; Weers, et al., 2003, Biophys. Chem. 100(1-3):481-92; Gong et al., 2002, J. Biol. Chem. 277(33):29919-26; Ohta et al., 1984, J. Biol. Chem. 259(23):14888-93 and U.S. Pat. No. 6,372,886).

In certain embodiments, the methods and compositions of the present invention include the use of a chimeric construction of an apolipoprotein. For example, a chimeric construction of an apolipoprotein can be comprised of an apolipoprotein domain with high lipid binding capacity associated with an apolipoprotein domain containing ischemia reperfusion protective properties. A chimeric construction of an apolipoprotein can be a construction that includes separate regions within an apolipoprotein (i.e., homologous construction) or a chimeric construction can be a construction that includes separate regions between different apolipoproteins (i.e., heterologous constructions). Compositions comprising a chimeric construction can also include segments that are apolipoprotein variants or segments designed to have a specific character (e.g., lipid binding, receptor binding, enzymatic, enzyme activating, antioxidant or reduction-oxidation property) (see Weisgraber 1990, J. Lipid Res. 31(8):1503-11; Hixson and Powers 1991, J. Lipid Res. 32(9):1529-35; Lackner et al., 1985, J. Biol. Chem. 260(2):703-6; Hoeg et al., 1986, J. Biol. Chem. 261(9):3911-4; Gordon et al., 1984, J. Biol. Chem. 259(1):468-74; Powell et al., 1987, Cell 50(6):

831-40; Aviram et al., 1998, Arterioscler. Thromb. Vasc. Biol. 18(10):1617-24; Aviram et al., 1998, J. Clin. Invest. 101(8): 1581-90; Billecke et al., 2000, Drug Metab. Dispos. 28(11): 1335-42; Draganov et al., 2000, J. Biol. Chem. 275(43): 33435-42; Steinmetz and Utermann 1985, J. Biol. Chem. 260(4):2258-64; Widler et al., 1980, J. Biol. Chem. 255(21): 10464-71; Dyer et al., 1995, J. Lipid Res. 36(1):80-8; Sorenson et al., 1999, Arterioscler. Thromb. Vasc. Biol. 19(9):2214-25; Palgunachari 1996, Arterioscler. Throb. Vasc. Biol. 16(2): 328-38: Thurberg et al., J. Biol. Chem. 271(11):6062-70; Dyer 1991, J. Biol. Chem. 266(23):150009-15; Hill 1998, J. Biol. Chem. 273(47):30979-84).

Apolipoproteins utilized in the invention also include recombinant, synthetic, semi-synthetic or purified apolipoproteins. Methods for obtaining apolipoproteins or equivalents thereof, utilized by the invention are well-known in the art. For example, apolipoproteins can be separated from plasma or natural products by, for example, density gradient centrifugation or immunoaffinity chromatography, or produced synthetically, semi-synthetically or using recombinant DNA techniques known to those of the art (see, e.g., Mulugeta et al., 1998, J. Chromatogr. 798(1-2): 83-90; Chung et al., 1980, J. Lipid Res. 21(3):284-91; Cheung et al., 1987, J. Lipid Res. 28(8):913-29; Persson, et al., 1998, J. Chromatogr. 711: 97-109; U.S. Pat. Nos. 5,059,528, 5,834,596, 5,876,968 and 5,721,114; and PCT Publications WO 86/04920 and WO 87/02062).

Apolipoproteins utilized in the invention further include apolipoprotein agonists such as peptides and peptide analogues that mimic the activity of ApoA-I, ApoA-I Milano (ApoA-$I_M$), ApoA-I Paris (ApoA-$I_P$), ApoA-II, ApoA-IV, and ApoE. For example, the apolipoprotein can be any of those described in U.S. Pat. Nos. 6,004,925, 6,037,323, 6,046,166, and 5,840,688, the contents of which are incorporated herein by reference in their entireties.

Apolipoprotein agonist peptides or peptide analogues can be synthesized or manufactured using any technique for peptide synthesis known in the art including, e.g., the techniques described in U.S. Pat. Nos. 6,004,925, 6,037,323 and 6,046, 166. For example, the peptides may be prepared using the solid-phase synthetic technique initially described by Merrifield (1963, J. Am. Chem. Soc. 85:2149-2154). Other peptide synthesis techniques may be found in Bodanszky et al., Peptide Synthesis, John Wiley & Sons, 2d Ed., (1976) and other references readily available to those skilled in the art. A summary of polypeptide synthesis techniques can be found in Stuart and Young, Solid Phase Peptide. Synthesis, Pierce Chemical Company, Rockford, Ill., (1984). Peptides may also be synthesized by solution methods as described in The Proteins, Vol. II, 3d Ed., Neurath et al., Eds., p. 105-237, Academic Press, New York, N.Y. (1976). Appropriate protective groups for use in different peptide syntheses are described in the above-mentioned texts as well as in McOmie, Protective Groups in Organic Chemistry, Plenum Press, New York, N.Y. (1973). The peptides of the present invention might also be prepared by chemical or enzymatic cleavage from larger portions of, for example, apolipoprotein A-I.

In certain embodiments, the apolipoprotein can be a mixture of apolipoproteins. In one embodiment, the apolipoprotein can be a homogeneous mixture, that is, a single type of apolipoprotein. In another embodiment, the apolipoprotein can be a heterogeneous mixture of apolipoproteins, that is, a mixture of two or more different apolipoproteins. Embodiments of heterogenous mixtures of apolipoproteins can comprise, for example, a mixture of an apolipoprotein from an animal source and an apolipoprotein from a semi-synthetic source. In certain embodiments, a heterogenous mixture can comprise, for example, a mixture of ApoA-I and ApoA-I Milano. In certain embodiments, a heterogeneous mixture can comprise, for example, a mixture of ApoA-I Milano and ApoA-I Paris. Suitable mixtures for use in the methods and compositions of the invention will be apparent to one of skill in the art.

If the apolipoprotein is obtained from natural sources, it can be obtained from a plant or animal source. If the apolipoprotein is obtained from an animal source, the apolipoprotein can be from any species. In certain embodiments, the apolipoprotien can be obtained from an animal source. In certain embodiments, the apolipoprotein can be obtained from a human source. In preferred embodiments of the invention, the apolipoprotein is derived from the same species as the individual to which the apolipoprotein is administered.

Other Components

In numerous embodiments, amphipathic lipids are included in lipid particles of the invention. "Amphipathic lipids" refer to any suitable material, wherein the hydrophobic portion of the lipid material orients into a hydrophobic phase, while the hydrophilic portion orients toward the aqueous phase. Such compounds include, but are not limited to, phospholipids, aminolipids, and sphingolipids. Representative phospholipids include sphingomyelin, phosphatidylcholine, phosphatidylethanolamine, phosphatidylserine, phosphatidylinositol, phosphatidic acid, palmitoyloleoyl phosphatdylcholine, lysophosphatidylcholine, lysophosphatidylethanolamine, dipalmitoylphosphatidylcholine, dioleoylphosphatidylcholine, distearoylphosphatidylcholine, or dilinoleylphosphatidylcholine. Other phosphorus-lacking compounds, such as sphingolipids, glycosphingolipid families, diacylglycerols, and 13-acyloxyacids, can also be used. Additionally, such amphipathic lipids can be readily mixed with other lipids, such as triglycerides and sterols.

Also suitable for inclusion in the lipid particles of the invention are programmable fusion lipids. Such lipid particles have little tendency to fuse with cell membranes and deliver their payload until a given signal event occurs. This allows the lipid particle to distribute more evenly after injection into an organism or disease site before it starts fusing with cells. The signal event can be, for example, a change in pH, temperature, ionic environment, or time. In the latter case, a fusion delaying or "cloaking" component, such as an ATTA-lipid conjugate or a PEG-lipid conjugate, can simply exchange out of the lipid particle membrane over time. Exemplary lipid anchors include those having lengths of from about $C_{14}$ to about $C_{22}$, preferably from about $C_{14}$ to about $C_{16}$. In some embodiments, a PEG moiety, for example an mPEG-$NH_2$, has a size of about 1000, 2000, 5000, 10,000, 15,000 or 20,000 daltons.

A lipid particle conjugated to a nucleic acid agent can also include a targeting moiety, e.g., a targeting moiety that is specific to a cell type or tissue. Targeting of lipid particles using a variety of targeting moieties, such as ligands, cell surface receptors, glycoproteins, vitamins (e.g., riboflavin) and monoclonal antibodies, has been previously described (see, e.g., U.S. Pat. Nos. 4,957,773 and 4,603,044). The targeting moieties can include the entire protein or fragments thereof. Targeting mechanisms generally require that the targeting agents be positioned on the surface of the lipid particle in such a manner that the targeting moiety is available for interaction with the target, for example, a cell surface receptor. A variety of different targeting agents and methods are known and available in the art, including those described, e.g., in Sapra, P. and Allen, T M, Prog. Lipid Res. 42(5):439-62 (2003); and Abra, R M et al., J. Liposome Res. 12:1-3, (2002).

The use of lipid particles, i.e., liposomes, with a surface coating of hydrophilic polymer chains, such as polyethylene glycol (PEG) chains, for targeting has been proposed (Allen, et al., *Biochimica et Biophysica Acta* 1237: 99-108 (1995); DeFrees, et al., *Journal of the American Chemistry Society* 118: 6101-6104 (1996); Blume, et al., *Biochimica et Biophysica Acta* 1149: 180-184 (1993); Klibanov, et al., *Journal of Liposome Research* 2: 321-334 (1992); U.S. Pat. No. 5,013,556; Zalipsky, Bioconjugate Chemistry 4: 296-299 (1993); Zalipsky, *FEBS Letters* 353: 71-74 (1994); Zalipsky, in Stealth Liposomes Chapter 9 (Lasic and Martin, Eds) CRC Press, Boca Raton Fla. (1995). In one approach, a ligand, such as an antibody, for targeting the lipid particle is linked to the polar head group of lipids forming the lipid particle. In another approach, the targeting ligand is attached to the distal ends of the PEG chains forming the hydrophilic polymer coating (Klibanov, et al., *Journal of Liposome Research* 2: 321-334 (1992); Kirpotin et al., *FEBS Letters* 388: 115-118 (1996)).

Standard methods for coupling the target agents can be used. For example, phosphatidylethanolamine, which can be activated for attachment of target agents, or derivatized lipophilic compounds, such as lipid-derivatized bleomycin, can be used. Antibody-targeted liposomes can be constructed using, for instance, liposomes that incorporate protein A (see, Renneisen, et al., *J. Bio. Chem.*, 265:16337-16342 (1990) and Leonetti, et al., *Proc. Natl. Acad. Sci.* (USA), 87:2448-2451 (1990). Other examples of antibody conjugation are disclosed in U.S. Pat. No. 6,027,726, the teachings of which are incorporated herein by reference. Examples of targeting moieties can also include other proteins, specific to cellular components, including antigens associated with neoplasms or tumors. Proteins used as targeting moieties can be attached to the liposomes via covalent bonds (see, Heath, *Covalent Attachment of Proteins to Liposomes,* 149 *Methods in Enzymology* 111-119 (Academic Press, Inc. 1987)). Other targeting methods include the biotin-avidin system.

Production of Nucleic Acid-Lipid Particles

In one embodiment, the nucleic acid-lipid particle formulations of the invention are produced via an extrusion method or an in-line mixing method.

The extrusion method (also referred to as preformed method or batch process) is a method where the empty liposomes (i.e. no nucleic acid) are prepared first, followed by the addition of nucleic acid to the empty liposome. Extrusion of liposome compositions through a small-pore polycarbonate membrane or an asymmetric ceramic membrane results in a relatively well-defined size distribution. Typically, the suspension is cycled through the membrane one or more times until the desired liposome complex size distribution is achieved. The liposomes may be extruded through successively smaller-pore membranes, to achieve a gradual reduction in liposome size. In some instances, the lipid-nucleic acid compositions which are formed can be used without any sizing. These methods are disclosed in the U.S. Pat. No. 5,008,050; U.S. Pat. No. 4,927,637; U.S. Pat. No. 4,737,323; *Biochim Biophys Acta.* 1979 Oct. 19; 557(1):9-23; *Biochim Biophys Acta.* 1980 Oct. 2; 601(3):559-7; *Biochim Biophys Acta.* 1986 Jun. 13; 858(1):161-8; and *Biochim. Biophys. Acta* 1985 812, 55-65, which are hereby incorporated by reference in their entirety.

The in-line mixing method is a method wherein both the lipids and the nucleic acid are added in parallel into a mixing chamber. The mixing chamber can be a simple T-connector or any other mixing chamber that is known to one skill in the art. These methods are disclosed in U.S. Pat. No. 6,534,018 and U.S. Pat. No. 6,855,277; US publication 2007/0042031 and *Pharmaceuticals Research*, Vol. 22, No. 3, March 2005, p. 362-372, which are hereby incorporated by reference in their entirety.

It is further understood that the formulations of the invention can be prepared by any methods known to one of ordinary skill in the art.

Characterization of Nucleic Acid-Lipid Particles

Formulations prepared by either the standard or extrusion-free method can be characterized in similar manners. For example, formulations are typically characterized by visual inspection. They should be whitish translucent solutions free from aggregates or sediment. Particle size and particle size distribution of lipid-nanoparticles can be measured by light scattering using, for example, a Malvern Zetasizer Nano ZS (Malvern, USA). Particles should be about 20-300 nm, such as 40-100 nm in size. The particle size distribution should be unimodal. The total siRNA concentration in the formulation, as well as the entrapped fraction, is estimated using a dye exclusion assay. A sample of the formulated siRNA can be incubated with an RNA-binding dye, such as Ribogreen (Molecular Probes) in the presence or absence of a formulation disrupting surfactant, e.g., 0.5% Triton-X100. The total siRNA in the formulation can be determined by the signal from the sample containing the surfactant, relative to a standard curve. The entrapped fraction is determined by subtracting the "free" siRNA content (as measured by the signal in the absence of surfactant) from the total siRNA content. Percent entrapped siRNA is typically >85%. In one embodiment, the formulations of the invention are entrapped by at least 75%, at least 80% or at least 90%.

For nucleic acid-lipid particle formulations, the particle size is at least 30 nm, at least 40 nm, at least 50 nm, at least 60 nm, at least 70 nm, at least 80 nm, at least 90 nm, at least 100 nm, at least 110 nm, and at least 120 nm. The suitable range is typically about at least 50 nm to about at least 110 nm, about at least 60 nm to about at least 100 nm, or about at least 80 nm to about at least 90 nm.

LNP01

One example of synthesis of a nucleic acid-lipid particle is as follows. Nucleic acid-lipid particles are synthesized using the lipidoid ND98.4HCl (MW 1487) (Formula I), Cholesterol (Sigma-Aldrich), and PEG-Ceramide C16 (Avanti Polar Lipids). This nucleic acid-lipid particle is sometimes referred to as a LNP01 particles. Stock solutions of each in ethanol can be prepared as follows: ND98, 133 mg/ml; Cholesterol, 25 mg/ml, PEG-Ceramide C16, 100 mg/ml. The ND98, Cholesterol, and PEG-Ceramide C16 stock solutions can then be combined in a, e.g., 42:48:10 molar ratio. The combined lipid solution can be mixed with aqueous siRNA (e.g., in sodium acetate pH 5) such that the final ethanol concentration is about 35-45% and the final sodium acetate concentration is about 100-300 mM. Lipid-siRNA nanoparticles typically form spontaneously upon mixing. Depending on the desired particle size distribution, the resultant nanoparticle mixture can be extruded through a polycarbonate membrane (e.g., 100 nm cut-off) using, for example, a thermobarrel extruder, such as Lipex Extruder (Northern Lipids, Inc). In some cases, the extrusion step can be omitted. Ethanol removal and simultaneous buffer exchange can be accomplished by, for example, dialysis or tangential flow filtration. Buffer can be exchanged with, for example, phosphate buffered saline (PBS) at about pH 7, e.g., about pH 6.9, about pH 7.0, about pH 7.1, about pH 7.2, about pH 7.3, or about pH 7.4.

Formula 1

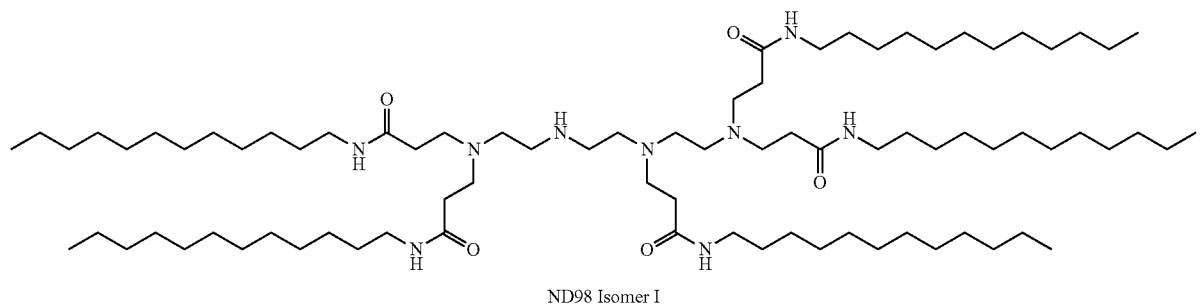

ND98 Isomer I

LNP01 formulations are described, e.g., in International Application Publication No. WO 2008/042973, which is hereby incorporated by reference.

Exemplary Nucleic Acid-Lipid Particle Formulations

Additional exemplary nucleic acid-lipid particle formulations are described in the following table. It is to be understood that the name of the nucleic acid-lipid particle in the table is not meant to be limiting. For example, as used herein, the term SNALP refers to formulations that include the cationic lipid DLinDMA.

| Name | cationic lipid/non-cationic lipid/cholesterol/PEG-lipid conjugate mol % ratio<br>Lipid:siRNA ratio |
|---|---|
| SNALP | DLinDMA/DPPC/Cholesterol/PEG-cDMA<br>(57.1/7.1/34.4/1.4)<br>lipid:siRNA ~7:1 |
| LNP-S-X | XTC/DPPC/Cholesterol/PEG-cDMA<br>57.1/7.1/34.4/1.4<br>lipid:siRNA ~7:1 |
| LNP05 | XTC/DSPC/Cholesterol/PEG-DMG<br>57.5/7.5/31.5/3.5<br>lipid:siRNA ~6:1 |
| LNP06 | XTC/DSPC/Cholesterol/PEG-DMG<br>57.5/7.5/31.5/3.5<br>lipid:siRNA ~11:1 |
| LNP07 | XTC/DSPC/Cholesterol/PEG-DMG<br>60/7.5/31/1.5,<br>lipid:siRNA ~6:1 |
| LNP08 | XTC/DSPC/Cholesterol/PEG-DMG<br>60/7.5/31/1.5,<br>lipid:siRNA ~11:1 |
| LNP09 | XTC/DSPC/Cholesterol/PEG-DMG<br>50/10/38.5/1.5<br>lipid:siRNA ~10:1 |
| LNP10 | ALNY-100/DSPC/Cholesterol/PEG-DMG<br>50/10/38.5/1.5<br>lipid:siRNA ~10:1 |
| LNP11 | MC3/DSPC/Cholesterol/PEG-DMG<br>50/10/38.5/1.5<br>lipid:siRNA ~10:1 |
| LNP12 | C12-200/DSPC/Cholesterol/PEG-DMG<br>50/10/38.5/1.5<br>lipid:siRNA ~10:1 |
| LNP13 | XTC/DSPC/Cholesterol/PEG-DMG<br>50/10/38.5/1.5<br>lipid:siRNA ~33:1 |
| LNP14 | MC3/DSPC/Cholesterol/PEG-DMG<br>40/15/40/5<br>lipid:siRNA ~11:1 |
| LNP15 | MC3/DSPC/Cholesterol/PEG-DSG/GalNAc-PEG-DSG<br>50/10/35/4.5/0.5<br>lipid:siRNA ~11:1 |
| LNP16 | MC3/DSPC/Cholesterol/PEG-DMG<br>50/10/38.5/1.5<br>lipid:siRNA ~7:1 |
| LNP17 | MC3/DSPC/Cholesterol/PEG-DSG<br>50/10/38.5/1.5<br>lipid:siRNA ~10:1 |
| LNP18 | MC3/DSPC/Cholesterol/PEG-DMG<br>50/10/38.5/1.5<br>lipid:siRNA ~12:1 |
| LNP19 | MC3/DSPC/Cholesterol/PEG-DMG<br>50/10/35/5<br>lipid:siRNA ~8:1 |
| LNP20 | MC3/DSPC/Cholesterol/PEG-DPG<br>50/10/38.5/1.5<br>lipid:siRNA ~10:1 |
| LNP21 | C12-200/DSPC/Cholesterol/PEG-DSG<br>50/10/38.5/1.5<br>lipid:siRNA ~7:1 |
| LNP22 | XTC/DSPC/Cholesterol/PEG-DSG<br>50/10/38.5/1.5<br>lipid:siRNA ~10:1 |

DLinDMA comprising formulations such as that used in ALN-VSP02 are described, e.g., in application number PCT/CA2009/00496, filed Apr. 15, 2009, which is hereby incorporated by reference.

XTC comprising formulations are described, e.g., in U.S. Provisional Ser. No. 61/239,686, filed Sep. 3, 2009, which is hereby incorporated by reference.

MC3 comprising formulations are described, e.g., in U.S. Provisional Ser. No. 61/244,834, filed Sep. 22, 2009, and U.S. Provisional Ser. No. 61/185,800, filed Jun. 10, 2009, which are hereby incorporated by reference.

ALNY-100 comprising formulations are described, e.g., International patent application number PCT/US09/63933, filed on Nov. 10, 2009, which is hereby incorporated by reference.

C12-200 comprising formulations are described in International patent application number PCT/US10/33777 filed May 5, 2010 and in Love et al (Love et al. (2010) PNAS 107(5); 1864-69) which are hereby incorporated by reference.

Additional Formulations

Emulsions

The compositions of the present invention may be prepared and formulated as emulsions. Emulsions are typically heterogeneous systems of one liquid dispersed in another in the form of droplets usually exceeding 0.1 μm in diameter (Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising two immiscible liquid phases intimately mixed and dispersed with each other. In general, emulsions may be of either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (o/w) emulsion. Emulsions may contain additional components in addition to the dispersed phases, and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, non-swelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in Pharmaceutical Dosage Forms, Lieberman, Rieger and Banker (Eds.), 1988, Marcel Dekker, Inc., New York, N.Y., volume 1, p. 199). Emulsion formulations for oral delivery have been very widely used because of ease of formulation, as well as efficacy from an absorption and bioavailability standpoint (Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of dsRNAs and nucleic acids are formulated as microemulsions. A microemulsion may be defined as a system of water, oil and amphiphile which is a single optically isotropic and thermodynamically stable liquid solution (Rosoff, in Pharmaceutical Dosage Forms, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in Remington's Pharmaceutical Sciences, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in Pharmaceutical Dosage Forms, Lieberman, Rieger and Banker (Eds.), 1988, Marcel Dekker, Inc., New York, N.Y., volume 1, p. 245; Block, in Pharmaceutical Dosage Forms, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (M0310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., Pharmaceutical Research, 1994, 11, 1385-1390; Ritschel, Meth. Find. Exp. Clin. Pharmacol., 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., Pharmaceutical Research, 1994, 11, 1385; Ho et al., J. Pharm. Sci., 1996, 85, 138-143). Often microemulsions may form spontaneously when their components are brought together at ambient temperature. This may be particularly advantageous when formulating thermolabile drugs, peptides or dsRNAs. Microemulsions have also been effective in the transdermal delivery of active components in both cosmetic and pharmaceutical applications. It is expected that the microemulsion compositions and formulations of the present invention will facilitate the increased systemic absorption of dsRNAs and nucleic acids from the gastrointestinal tract, as well as improve the local cellular uptake of dsRNAs and nucleic acids.

Microemulsions of the present invention may also contain additional components and additives such as sorbitan monostearate (Grill 3), Labrasol, and penetration enhancers to improve the properties of the formulation and to enhance the absorption of the dsRNAs and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., Critical Reviews in Therapeutic Drug Carrier Systems, 1991, p. 92). Each of these classes has been discussed above.

Penetration Enhancers

In one embodiment, the present invention employs various penetration enhancers to effect the efficient delivery of nucleic acids, particularly dsRNAs, to the skin of animals. Most drugs are present in solution in both ionized and non-ionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., Critical Reviews in Therapeutic Drug Carrier Systems, 1991, p. 92). Each of the above mentioned classes of penetration enhancers are described below in greater detail.

Surfactants: In connection with the present invention, surfactants (or "surface-active agents") are chemical entities which, when dissolved in an aqueous solution, reduce the surface tension of the solution or the interfacial tension between the aqueous solution and another liquid, with the result that absorption of dsRNAs through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., Critical Reviews in Therapeutic Drug Carrier Systems, 1991, p. 92); and perfluorochemical emulsions, such as FC-43. Takahashi et al., J. Pharm. Pharmacol., 1988, 40, 252).

Fatty acids: Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acycholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., Critical Reviews in Therapeutic Drug Carrier Systems, 1991, p. 92; Muranishi, Critical Reviews in Therapeutic Drug Carrier Systems, 1990, 7, 1-33; El Hariri et al., J. Pharm. Pharmacol., 1992, 44, 651-654).

Bile salts: The physiological role of bile includes the facilitation of dispersion and absorption of lipids and fat-soluble vitamins (Brunton, Chapter 38 in: Goodman & Gilman's The Pharmacological Basis of Therapeutics, 9th Ed., Hardman et al. Eds., McGraw-Hill, New York, 1996, pp. 934-935). Various natural bile salts, and their synthetic derivatives, act as penetration enhancers. Thus the term "bile salts" includes any of the naturally occurring components of bile as well as any of their synthetic derivatives. Suitable bile salts include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., Critical Reviews in Therapeutic Drug Carrier Systems, 1991, page 92; Swinyard, Chapter 39 In: Remington's Pharmaceutical Sciences, 18th Ed., Gennaro, ed., Mack Publishing Co., Easton, Pa., 1990, pages 782-783; Muranishi, Critical Reviews in Therapeutic Drug Carrier Systems, 1990, 7, 1-33; Yamamoto et al., J. Pharm. Exp. Ther., 1992, 263, 25; Yamashita et al., J. Pharm. Sci., 1990, 79, 579-583).

Chelating Agents: Chelating agents, as used in connection with the present invention, can be defined as compounds that remove metallic ions from solution by forming complexes therewith, with the result that absorption of dsRNAs through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, J. Chromatogr., 1993, 618, 315-339). Suitable chelating agents include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines) (Lee et al., Critical Reviews in Therapeutic Drug Carrier Systems, 1991, page 92; Muranishi, Critical Reviews in Therapeutic Drug Carrier Systems, 1990, 7, 1-33; Buur et al., J. Control Rel., 1990, 14, 43-51).

Non-chelating non-surfactants: As used herein, non-chelating non-surfactant penetration enhancing compounds can be defined as compounds that demonstrate insignificant activity as chelating agents or as surfactants but that nonetheless enhance absorption of dsRNAs through the alimentary mucosa (Muranishi, Critical Reviews in Therapeutic Drug Carrier Systems, 1990, 7, 1-33). This class of penetration enhancers include, for example, unsaturated cyclic ureas, 1-alkyl- and 1-alkenylazacyclo-alkanone derivatives (Lee et al., Critical Reviews in Therapeutic Drug Carrier Systems, 1991, page 92); and non-steroidal anti-inflammatory agents such as diclofenac sodium, indomethacin and phenylbutazone (Yamashita et al., J. Pharm. Pharmacol., 1987, 39, 621-626).

Agents that enhance uptake of dsRNAs at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of dsRNAs.

Other agents may be utilized to enhance the penetration of the administered nucleic acids, including glycols such as ethylene glycol and propylene glycol, pyrrols such as 2-pyrrol, azones, and terpenes such as limonene and menthone.

Carriers dsRNAs of the present invention can be formulated in a pharmaceutically acceptable carrier or diluent. A "pharmaceutically acceptable carrier" (also referred to herein as an "excipient") is a pharmaceutically acceptable solvent, suspending agent, or any other pharmacologically inert vehicle. Pharmaceutically acceptable carriers can be liquid or solid, and can be selected with the planned manner of administration in mind so as to provide for the desired bulk, consistency, and other pertinent transport and chemical properties. Typical pharmaceutically acceptable carriers include, by way of example and not limitation: water; saline solution; binding agents (e.g., polyvinylpyrrolidone or hydroxypropyl methylcellulose); fillers (e.g., lactose and other sugars, gelatin, or calcium sulfate); lubricants (e.g., starch, polyethylene glycol, or sodium acetate); disintegrates (e.g., starch or sodium starch glycolate); and wetting agents (e.g., sodium lauryl sulfate).

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The co-administration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate dsRNA in hepatic tissue can be reduced when it is co-administered with polyinosinic acid, dextran sulfate, polycytidic acid or 4-acetamido-4' isothiocyano-stilbene-2,2'-disulfonic acid (Miyao et al., DsRNA Res. Dev., 1995, 5, 115-121; Takakura et al., DsRNA & Nucl. Acid Drug Dev., 1996, 6, 177-183.

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc).

Pharmaceutically acceptable organic or inorganic excipients suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

Combination Therapy

In one aspect, a composition, e.g., ALN-VSP02, of the invention can be used in combination therapy. The term "combination therapy" includes the administration of the subject compounds in further combination with other biologically active ingredients (such as, but not limited to, a second and different antineoplastic agent) and non-drug therapies (such as, but not limited to, surgery or radiation treatment). For instance, the compounds of the invention can be used in combination with other pharmaceutically active compounds, preferably compounds that are able to enhance the effect of the compounds of the invention. The compounds of the invention can be administered simultaneously (as a single preparation or separate preparation) or sequentially to the other drug therapy. In general, a combination therapy envisions administration of two or more drugs during a single cycle or course of therapy.

In one aspect of the invention, the subject compounds may be administered in combination with one or more separate agents that modulate protein kinases involved in various disease states. Examples of such kinases may include, but are not limited to: serine/threonine specific kinases, receptor tyrosine specific kinases and non-receptor tyrosine specific kinases. Serine/threonine kinases include mitogen activated protein kinases (MAPK), meiosis specific kinase (MEK), RAF and aurora kinase. Examples of receptor kinase families include epidermal growth factor receptor (EGFR) (e.g., HER2/neu, HER3, HER4, ErbB, ErbB2, ErbB3, ErbB4, Xmrk, DER, Let23); fibroblast growth factor (FGF) receptor (e.g. FGF-R1, GFF-R2/BEK/CEK3, FGF-R3/CEK2, FGF-R4/TKF, KGF-R); hepatocyte growth/scatter factor receptor (HGFR) (e.g., MET, RON, SEA, SEX); insulin receptor (e.g. IGFI-R); Eph (e.g. CEK5, CEK8, EBK, ECK, EEK, EHK-I, EHK-2, ELK, EPH, ERK, HEK, MDK2, MDK5, SEK); AxI (e.g. Mer/Nyk, Rse); RET; and platelet-derived growth factor receptor (PDGFR) (e.g. PDGFα-R, PDGFβ-R, CSF1-R/FMS, SCF-R/C-KIT, VEGF-R/FLT, NEK/FLK1, FLT3/FLK2/STK-1). Non-receptor tyrosine kinase families include, but are not limited to, BCR-ABL (e.g. $p43^{abl}$, ARG); BTK (e.g. ITK/EMT, TEC); CSK, FAK, FPS, JAK, SRC, BMX, FER, CDK and SYK.

In another aspect of the invention, the subject compounds may be administered in combination with one or more agents that modulate non-kinase biological targets or processes. Such targets include histone deacetylases (HDAC), DNA methyltransferase (DNMT), heat shock proteins (e.g., HSP90), and proteosomes.

In one embodiment, subject compounds may be combined with antineoplastic agents (e.g. small molecules, monoclonal antibodies, antisense RNA, and fusion proteins) that inhibit one or more biological targets such as Zolinza, Tarceva, Iressa, Tykerb, Gleevec, Sutent, Sprycel, Nexavar, Sorafenib, CNF2024, RG108, BMS387032, Affmitak, Avastin, Herceptin, Erbitux, AG24322, PD325901, ZD6474, PD 184322, Obatodax, ABT737 and AEE788. Such combinations may enhance therapeutic efficacy over efficacy achieved by any of the agents alone and may prevent or delay the appearance of resistant mutational variants.

In certain preferred embodiments, the compounds of the invention are administered in combination with a chemotherapeutic agent. Chemotherapeutic agents encompass a wide range of therapeutic treatments in the field of oncology. These agents are administered at various stages of the disease for the purposes of shrinking tumors, destroying remaining cancer cells left over after surgery, inducing remission, maintaining remission and/or alleviating symptoms relating to the cancer or its treatment. Examples of such agents include, but are not limited to, alkylating agents such as mustard gas derivatives (Mechlorethamine, cylophosphamide, chlorambucil, melphalan, ifosfamide), ethylenimines (thiotepa, hexamethylmelanine), Alkylsulfonates (Busulfan), Hydrazines and Triazines (Altretamine, Procarbazine, Dacarbazine and Temozolomide), Nitrosoureas (Carmustine, Lomustine and Streptozocin), Ifosfamide and metal salts (Carboplatin, Cisplatin, and Oxaliplatin); plant alkaloids such as Podophyllotoxins (Etoposide and Tenisopide), Taxanes (Paclitaxel and Docetaxel), Vinca alkaloids (Vincristine, Vinblastine, Vindesine and Vinorelbine), and Camptothecan analogs (Irinotecan and Topotecan); anti-tumor antibiotics such as Chromomycins (Dactinomycin and Plicamycin), Anthracyclines (Doxorubicin, Daunorubicin, Epirubicin, Mitoxantrone, Valrubicin and Idarubicin), and miscellaneous antibiotics such as Mitomycin, Actinomycin and Bleomycin; anti-metabolites such as folic acid antagonists (Methotrexate, Pemetrexed, Raltitrexed, Aminopterin), pyrimidine antagonists (5-Fluorouracil, Floxuridine, Cytarabine, Capecitabine, and Gemcitabine), purine antagonists (6-Mercaptopurine and 6-Thioguanine) and adenosine deaminase inhibitors (Cladribine, Fludarabine, Mercaptopurine, Clofarabine, Thioguanine, Nelarabine and Pentostatin); topoisomerase inhibitors such as topoisomerase I inhibitors (Ironotecan, topotecan) and topoisomerase II inhibitors (Amsacrine, etoposide, etoposide phosphate, teniposide); monoclonal antibodies (Alemtuzumab, Gemtuzumab ozogamicin, Rituximab, Trastuzumab, Ibritumomab Tioxetan, Cetuximab, Panitumumab, Tositumomab, Bevacizumab); and miscellaneous anti-neoplasties such as ribonucleotide reductase inhibitors (Hydroxyurea); adrenocortical steroid inhibitor (Mitotane); enzymes (Asparaginase and Pegaspargase); anti-microtubule agents (Estramustine); and retinoids (Bexarotene, Isotretinoin, Tretinoin (ATRA). In certain preferred embodiments, the compounds of the invention are administered in combination with a chemoprotective agent. Chemoprotective agents act to protect the body or minimize the side effects of chemotherapy. Examples of such agents include, but are not limited to, amfostine, mesna, and dexrazoxane.

In one aspect of the invention, the subject compounds are administered in combination with radiation therapy. Radiation is commonly delivered internally (implantation of radioactive material near cancer site) or externally from a machine that employs photon (x-ray or gamma-ray) or particle radiation. Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

It will be appreciated that compounds of the invention can be used in combination with an immunotherapeutic agent. One form of immunotherapy is the generation of an active systemic tumor-specific immune response of host origin by administering a vaccine composition at a site distant from the tumor. Various types of vaccines have been proposed, including isolated tumor-antigen vaccines and anti-idiotype vaccines. Another approach is to use tumor cells from the subject to be treated, or a derivative of such cells (reviewed by Schirrmacher et al. (1995) J. Cancer Res. Clin. Oncol. 121:487). In U.S. Pat. No. 5,484,596, Hanna Jr. et al. claim a method for treating a resectable carcinoma to prevent recurrence or metastases, comprising surgically removing the tumor, dispersing the cells with collagenase, irradiating the cells, and vaccinating the patient with at least three consecutive doses of about $10^7$ cells.

It will be appreciated that the compounds of the invention may advantageously be used in conjunction with one or more adjunctive therapeutic agents. Examples of suitable agents for adjunctive therapy include steroids, such as corticosteroids (amcinonide, betamethasone, betamethasone dipropionate, betamethasone valerate, budesonide, clobetasol, clobetasol acetate, clobetasol butyrate, clobetasol 17-propionate, cortisone, deflazacort, desoximetasone, diflucortolone valerate, dexamethasone, dexamethasone sodium phosphate, desonide, furoate, fluocinonide, fluocinolone acetonide, halcinonide, hydrocortisone, hydrocortisone butyrate, hydrocortisone sodium succinate, hydrocortisone valerate, methyl prednisolone, mometasone, prednicarbate, prednisolone, triamcinolone, triamcinolone acetonide, and halobetasol proprionate); a 5HTi agonist, such as a triptan (e.g. sumatriptan or naratriptan); an adenosine Al agonist; an EP ligand; an NMDA modulator, such as a glycine antagonist; a sodium channel blocker (e.g. lamotrigine); a substance P antagonist (e.g. an NKi antagonist); a cannabinoid; acetaminophen or phenacetin; a 5-lipoxygenase inhibitor; a leukotriene receptor antagonist; a DMARD (e.g. methotrexate); gabapentin and related compounds; a tricyclic antidepressant (e.g. amitryptilline); a neurone stabilizing antiepileptic drug; a mono-aminergic uptake inhibitor (e.g. venlafaxine); a matrix metalloproteinase inhibitor; a nitric oxide synthase (NOS) inhibitor, such as an iNOS or an nNOS inhibitor; an inhibitor of the release, or action, of tumour necrosis factor α; an antibody therapy, such as a monoclonal antibody therapy; an antiviral agent, such as a nucleoside inhibitor (e.g. lamivudine) or an immune system modulator (e.g. interferon); an opioid analgesic; a local anaesthetic; a stimulant, including caffeine; an H2-antagonist (e.g. ranitidine); a proton pump inhibitor (e.g. omeprazole); an antacid (e.g. aluminium or magnesium hydroxide; an antiflatulent (e.g. simethicone); a decongestant (e.g. phenylephrine, phenylpropanolamine, pseudoephedrine, oxymetazoline, epinephrine, naphazoline, xylometazoline, propylhexedrine, or levo-desoxyephedrine); an antitussive (e.g. codeine, hydrocodone, carmiphen, carbetapentane, or dextramethorphan); a diuretic; or a sedating or non-sedating antihistamine.

The compounds of the invention can be co-administered with siRNA that target other genes. For example, a compound of the invention can be co-administered with an siRNA targeted to a c-Myc gene. In one example, AD-12115 can be co-administered with a c-Myc siRNA. Examples of c-Myc targeted siRNAs are disclosed in U.S. patent application Ser. No. 12/373,039 which is herein incorporated by reference.

Pharmacokinetics

The invention relates in particular to a method of treating a subject in need of treatment, where a composition of ALN-VSP02 is administered to the subject, resulting in a measurable $C_{max}$ and AUC in the plasma of the subject. The invention also relates to a composition of ALN-VSP02 used to treat a subject in need of treatment, where administration of the composition of ALN-VSP02 to the subject results in a measurable $C_{max}$ and AUC in the plasma of the subject. The $C_{max}$ and AUC are measurable for both VEGF and KSP siRNA components of the ALN-VSP02 composition.

$C_{max}$ is defined as the peak plasma concentration of a drug after administration of a dosage. It is an indication of the bioavailability and rate of absorption of a composition or drug into the plasma of the bloodstream of a subject following administration of the composition to a subject. As one of skill in the art will realize, $C_{max}$ is determined by taking multiple samples of the patient's blood at different time points after administration of a composition to a subject, and measuring the plasma concentration of the composition in each sample. In one embodiment of the present invention, $C_{max}$ is linearly correlated with dosage concentration. In one aspect, the mean $C_{max}$ for VEGF or KSP siRNA in the subject's plasma is between 0.4 to 13 µg/mL, the $C_{max}$ range linearly correlating with an intravenously administered dosage in the range of 0.1 to 0.7 mg/kg. In certain instances, mean $C_{max}$ for VEGF or KSP siRNA is in the range of about 0.4 to 1 µg/mL, 1.8 to 3 µg/mL, 2 to 5 µg/mL, or 5 to 14 µg/mL. In other instances mean $C_{max}$ values for VEGF or KSP siRNA are greater than 13 µg/mL. The Tables and Examples below provide values for mean $C_{max}$ values and ranges at various doses of the ALN-VSP02 composition.

AUC refers to the area under the curve of the concentration of a drug or composition in the plasma of the bloodstream over time after a dose is administered to a patient. It is affected by the rate of absorption into and the rate of removal of the drug or composition from the patient's blood plasma. As one of skill in the art knows, AUC can be determined by calculating the integral of the plasma composition concentration after the composition is administered. In another aspect, AUC can be predicted using the following formula:

Predicted AUC=$(D \times F)/CL$ where D is the dosage concentration, F is a measure of bioavailability, and CL is the predicted rate of clearance. In one embodiment of the invention, F is approximately 1 for intravenous dosage and predicted mean CL is about 1.21 ml/(min*kg) in an average human. One of skill in the art appreciates that the values for the predicted AUC have an error in the range of ±3- to 4-fold.

In some embodiments, the data for determining AUC is obtained by taking blood samples from the patient at various time intervals after administration of the composition. In one aspect, the mean AUC in the patient's plasma after administration of the ALN-VSP02 composition is in the range of about 10 to 800 μg*min/mL. In certain instances, the mean AUC of the ALN-VSP02 composition is in the range of about 10 to 50 μg*min/mL, 85 to 200 μg*min/mL, 160 to 250 μg*min/mL, or 300 to 800 μg*min/mL. In other instances, the mean AUC of the ALN-VSP02 composition are greater than 800 μg*min/mL. The Tables and Examples below provide values for mean AUC values and ranges at various doses of the ALN-VSP02 composition.

It is understood that the plasma concentration of a composition, such as ALN-VSP02, may vary significantly between subjects, due to variability with respect to metabolism and/or possible interactions with other therapeutic agents. In accordance with one aspect of the present invention, the blood plasma concentration of a compound, such as ALN-VSP02, may vary from subject to subject. Likewise, values such as maximum plasma concentration ($C_{max}$) or time to reach maximum plasma concentration ($T_{max}$) or area under the curve from time zero to time of last measurable concentration ($AUC_{last}$) or total area under the plasma concentration time curve (AUC) may vary from subject to subject. Due to this variability, the amount necessary to constitute "a therapeutically effective amount" of a compound, such as ALN-VSP02, may vary from subject to subject.

Methods for Treating Diseases Caused by Expression of the Eg5 and VEGF Genes

The invention relates in particular to the use of a composition, e.g., ALN-VSP02 and the like, containing at least two dsRNAs, one targeting an Eg5/KSP gene, and one targeting a VEGF gene, for the treatment of a cancer, such as liver cancer, e.g., for inhibiting tumor growth and tumor metastasis. For example, a composition, such as pharmaceutical composition, may be used for the treatment of solid tumors, like intrahepatic tumors such as may occur in cancers of the liver.

A composition containing a dsRNA targeting Eg5/KSP and a dsRNA targeting VEGF may also be used to treat other tumors and cancers, such as breast cancer, lung cancer, head and neck cancer, brain cancer, abdominal cancer, colon cancer, colorectal cancer, esophagus cancer, gastrointestinal cancer, glioma, tongue cancer, neuroblastoma, osteosarcoma, ovarian cancer, pancreatic cancer, prostate cancer, retinoblastoma, Wilm's tumor, multiple myeloma and for the treatment of skin cancer, like melanoma, for the treatment of lymphomas and blood cancer. The invention further relates to the use of a composition containing an Eg5 dsRNA and a VEGF dsRNA for inhibiting accumulation of ascites fluid and pleural effusion in different types of cancer, e.g., liver cancer, breast cancer, lung cancer, head cancer, neck cancer, brain cancer, abdominal cancer, colon cancer, colorectal cancer, esophagus cancer, gastrointestinal cancer, glioma, tongue cancer, neuroblastoma, osteosarcoma, ovarian cancer, pancreatic cancer, prostate cancer, retinoblastoma, Wilm's tumor, multiple myeloma, skin cancer, melanoma, lymphomas and blood cancer. Owing to the inhibitory effects on Eg5 and VEGF expression, a composition according to the invention or a pharmaceutical composition prepared therefrom can enhance the quality of life.

In one embodiment, a patient having a tumor associated with AFP expression, or a tumor secreting AFP, e.g., a hepatoma or teratoma, is treated. In certain embodiments, the patient has a malignant teratoma, an endodermal sinus tumor (yolk sac carcinoma), a neuroblastoma, a hepatoblastoma, a heptocellular carcinoma, testicular cancer or ovarian cancer.

In yet another aspect, the invention provides a method for inhibiting the expression of the Eg5 gene and the VEGF gene in a mammal. The method includes administering a composition featured in the invention to the mammal such that expression of the target Eg5 gene and the target VEGF gene is reduced.

The invention furthermore relates to the use of a dsRNA or a pharmaceutical composition thereof, e.g., ALN-VSP02, for treating cancer or for preventing tumor metastasis, in combination with other pharmaceuticals and/or other therapeutic methods, e.g., with known pharmaceuticals and/or known therapeutic methods, such as, for example, those which are currently employed for treating cancer and/or for preventing tumor metastasis. Preference is given to a combination with radiation therapy and chemotherapeutic agents, such as cisplatin, cyclophosphamide, 5-fluorouracil, adriamycin, daunorubicin or tamoxifen.

The invention can also be practiced by including with a specific RNAi agent, in combination with another anti-cancer chemotherapeutic agent, such as any conventional chemotherapeutic agent. The combination of a specific binding agent with such other agents can potentiate the chemotherapeutic protocol. Numerous chemotherapeutic protocols will present themselves in the mind of the skilled practitioner as being capable of incorporation into the method of the invention. Any chemotherapeutic agent can be used, including alkylating agents, antimetabolites, hormones and antagonists, radioisotopes, as well as natural products. For example, the compound of the invention can be administered with antibiotics such as doxorubicin and other anthracycline analogs, nitrogen mustards such as cyclophosphamide, pyrimidine analogs such as 5-fluorouracil, cisplatin, hydroxyurea, taxol and its natural and synthetic derivatives, and the like. As another example, in the case of mixed tumors, such as adenocarcinoma of the breast, where the tumors include gonadotropin-dependent and gonadotropin-independent cells, the compound can be administered in conjunction with leuprolide or goserelin (synthetic peptide analogs of LH-RH). Other antineoplastic protocols include the use of a tetracycline compound with another treatment modality, e.g., surgery, radiation, etc., also referred to herein as "adjunct antineoplastic modalities." Thus, the method of the invention can be employed with such conventional regimens with the benefit of reducing side effects and enhancing efficacy.

When the organism to be treated is a mammal such as a human, the composition may be administered by any means known in the art including, but not limited to oral or parenteral routes, including intravenous, intramuscular, subcutaneous, transdermal, airway (aerosol), nasal, rectal, and topical (including buccal and sublingual) administration. In preferred embodiments, the compositions are administered by intravenous infusion or injection.

The compositions and methods of the invention can be used to achieve a number of functional endpoints in addition to inhibiting expression of VEGF and/or Eg5 (KSP). These functional endpoints include but are not limited to extending survival, preventing tumor formation, reducing tumor formation, reducing tumor growth rate, increasing tumor cell monoaster formation, increasing tumor cell aberrant mitotic figure formation, reducing intratumoral hemorrhage, and reducing tumor microvessel density, e.g., when compared to a control.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Example 1 dsRNA Synthesis

Source of Reagents

Where the source of a reagent is not specifically given herein, such reagent may be obtained from any supplier of reagents for molecular biology at a quality/purity standard for application in molecular biology.

siRNA Synthesis

For screening of dsRNA, single-stranded RNAs were produced by solid phase synthesis on a scale of 1 µmole using an Expedite 8909 synthesizer (Applied Biosystems, Applera Deutschland GmbH, Darmstadt, Germany) and controlled pore glass (CPG, 500 Å, Proligo Biochemie GmbH, Hamburg, Germany) as solid support. RNA and RNA containing 2'-O-methyl nucleotides were generated by solid phase synthesis employing the corresponding phosphoramidites and 2'-O-methyl phosphoramidites, respectively (Proligo Biochemie GmbH, Hamburg, Germany). These building blocks were incorporated at selected sites within the sequence of the oligoribonucleotide chain using standard nucleoside phosphoramidite chemistry such as described in Current protocols in nucleic acid chemistry, Beaucage, S. L. et al. (Edrs.), John Wiley & Sons, Inc., New York, N.Y., USA. Phosphorothioate linkages were introduced by replacement of the iodine oxidizer solution with a solution of the Beaucage reagent (Chruachem Ltd, Glasgow, UK) in acetonitrile (1%). Further ancillary reagents were obtained from Mallinckrodt Baker (Griesheim, Germany).

Deprotection and purification of the crude oligoribonucleotides by anion exchange HPLC were carried out according to established procedures. Yields and concentrations were determined by UV absorption of a solution of the respective RNA at a wavelength of 260 nm using a spectral photometer (DU 640B, Beckman Coulter GmbH, Unterschleißheim, Germany). Double stranded RNA was generated by mixing an equimolar solution of complementary strands in annealing buffer (20 mM sodium phosphate, pH 6.8; 100 mM sodium chloride), heated in a water bath at 85-90° C. for 3 minutes and cooled to room temperature over a period of 3-4 hours. The annealed RNA solution was stored at −20° C. until use.

The synthesis of siRNAs bearing a 5'-12-dodecanoic acid bisdecylamide group (herein referred to as "5'-C32-") or a 5'-cholesteryl derivative group (herein referred to as "5'-Chol-") was performed as described in WO 2004/065601, except that, for the cholesteryl derivative, the oxidation step was performed using the Beaucage reagent in order to introduce a phosphorothioate linkage at the 5'-end of the nucleic acid oligomer.

dsRNA Targeting the Eg5 Gene

Initial Screening Set siRNA design was carried out to identify siRNAs targeting Eg5 (also known as KSP, KIF11, HSKP, KNSL1 and TRIPS). The mRNA sequence to for human Eg5 was used, NCBI ACCESSION NM_004523.

```
Eg5/KSP human mRNA, ref NM_004523
                                                              (SEQ ID NO: 11)
   1 agcgcagcca ttggtccggc tactctgtct cttttcaaa ttgaggcgcc gagtcgttgc 61 ttagtttctg gggattcggg cggagacgag attagtgatt tggcggctcc gactggcgcg 121 ggacaaacgc cacggccaga gtaccgggta gagagcgggg acgccgacct gcgtgcgtcg 181 gtcctccagg ccacgccagc gcccgagagg gaccagggag actccggccc ctgtcggccg 241 ccaagcccct ccgcccctca cagcgcccag gtccgcggcc gggccttgat tttttggcgg 301 ggaccgtcat ggcgtcgcag ccaaattcgt ctgcgaagaa gaagaggag aaggggaaga 361 acatccaggt ggtggtgaga tgcagaccat ttaatttggc agagcggaaa gctagcgccc 421 attcaatagt agaatgtgat cctgtacgaa aagaagttag tgtacgaact ggaggattgg 481 ctgacaagag ctcaaggaaa acatacactt ttgatatggt gtttggagca tctactaaac 541 agattgatgt ttaccgaagt gttgtttgtc caattctgga tgaagttatt atgggctata 601 attgcactat ctttgcgtat ggccaaactg gcactggaaa aactttttaca atggaaggtg 661 aaaggtcacc taatgaagag tatacctggg aagaggatcc cttggctggt ataattccac 721 gtacccttca tcaaattttt gagaaactta ctgataatgg tactgaattt tcagtcaaag 781 tgtctctgtt ggagatctat aatgaagagc ttttgatct tcttaatcca tcatctgatg
```

-continued

```
 841 tttctgagag actacagatg tttgatgatc cccgtaacaa gagaggagtg ataattaaag 901 gtttagaaga aattacagta cacaacaagg atgaagtcta tcaaattta gaaaagggg 961 cagcaaaaag gacaactgca gctactctga tgaatgcata ctctagtcgt tcccactcag 1021 ttttctctgt tacaatacat atgaaagaaa ctacgattga tggagaagag cttgttaaaa 1081 tcggaaagtt gaacttggtt gatcttgcag gaagtgaaaa cattggccgt tctggagctg 1141 ttgataagag agctcgggaa gctggaaata taaatcaatc cctgttgact tgggaaggg 1201 tcattactgc ccttgtagaa agaacacctc atgttcctta tcgagaatct aaactaacta 1261 gaatcctcca ggattctctt ggagggcgta caagaacatc tataattgca acaatttctc 1321 ctgcatctct caatcttgag gaaactctga gtacattgga atatgctcat agagcaaaga 1381 acatattgaa taagcctgaa gtgaatcaga aactccaccaa aaaagctctt attaaggagt 1441 atacggagga gatagaacgt ttaaaacgag atcttgctgc agcccgtgag aaaaatggag 1501 tgtatatttc tgaagaaaat tttagagtca tgagtggaaa attaactgtt caagaagagc 1561 agattgtaga attgattgaa aaaattggtg ctgttgagga ggagctgaat agggttacag 1621 agttgtttat ggataataaa aatgaacttg accagtgtaa atctgacctg caaaataaaa 1681 cacaagaact tgaaaccact caaaaacatt tgcaagaaac taaattacaa cttgttaaag 1741 aagaatatat cacatcagct ttggaaagta ctgaggagaa acttcatgat gctgccagca 1801 agctgcttaa cacagttgaa gaaactacaa agatgtatc tggtctccat tccaaactgg 1861 atcgtaagaa ggcagttgac caacacaatg cagaagctca ggatattttt ggcaaaaacc 1921 tgaatagtct gttaataat atggaagaat taattaagga tggcagctca aagcaaaagg 1981 ccatgctaga agtacataag accttatttg gtaatctgct gtcttccagt gtctctgcat 2041 tagataccat tactacagta gcacttggat ctctcacatc tattccagaa aatgtgtcta 2101 ctcatgtttc tcagattttt aatatgatac taaaagaaca atcattagca gcagaaagta 2161 aaactgtact acaggaattg attaatgtac tcaagactga tcttctaagt tcactggaaa 2221 tgattttatc cccaactgtg gtgtctatac tgaaaatcaa tagtcaacta aagcatattt 2281 tcaagacttc attgacagtg gccgataaga tagaagatca aaaaaaggaa ctagatggct 2341 ttctcagtat actgtgtaac aatctacatg aactacaaga aaataccatt tgttccttgg 2401 ttgagtcaca aaagcaatgt ggaaacctaa ctgaagacct gaagcaata aagcagaccc 2461 attcccagga acttcgcaag ttaatgaatc tttggacaga gagattctgt gctttggagg 2521 aaaagtgtga aaatatacag aaaccactta gtagtgtcca ggaaaatata cagcagaaat 2581 ctaaggatat agtcaacaaa atgactttc acagtcaaaa attttgtgct gattctgatg 2641 gcttctcaca ggaactcaga atttttaacc aagaaggtac aaaattggtt gaagaatctg 2701 tgaaacactc tgataaactc aatggcaacc tggaaaaaat atctcaagag actgaacaga 2761 gatgtgaatc tctgaacaca agaacagttt atttttctga acagtgggta tcttccttaa 2821 atgaaaggga acaggaactt cacaacttat tggaggttgt aagccaatgt tgtgaggctt 2881 caagttcaga catcactgag aaatcagatg gacgtaaggc agctcatgag aaacagcata 2941 acatttttct tgatcagatg actattgatg aagataaatt gatagcacaa aatctagaac 3001 ttaatgaaac cataaaaatt ggtttgacta gcttaattg ctttctggaa caggatctga 3061 aactggatat cccaacaggt acgacaccac agaggaaaag ttatttatac ccatcaacac 3121 tggtaagaac tgaaccacgt gaacatctcc ttgatcagct gaaaaggaaa cagcctgagc 3181 tgttaatgat gctaaactgt tcagaaaaca caaagaaga gacaattccg gatgtggatg 3241 tagaagaggc agttctgggg cagtatactg aagaacctct aagtcaagag ccatctgtag
```

```
3301 atgctggtgt ggattgttca tcaattggcg gggttccatt tttccagcat aaaaaatcac 3361 atggaaaaga caaagaaaac agaggcatta acacactgga gaggtctaaa gtggaagaaa 3421 ctacagagca cttggttaca aagagcagat tacctctgcg agcccagatc aacctttaat 3481 tcacttgggg gttggcaatt ttatttttaa agaaaactta aaaataaaac ctgaaacccc 3541 agaacttgag ccttgtgtat agattttaaa agaatatata tatcagccgg gcgcggtggc 3601 tcatgcctgt aatcccagca ctttgggagg ctgaggcggg tggattgctt gagcccagga 3661 gtttgagacc agcctggcca acgtggcaaa acctcgtctc tgttaaaaat tagccgggcg 3721 tggtggcaca ctcctgtaat cccagctact ggggaggctg aggcacgaga atcacttgaa 3781 cccaggaagc ggggttgcag tgagccaaag gtacaccact acactccagc ctgggcaaca 3841 gagcaagact cggtctcaaa aacaaaattt aaaaaagata taaggcagta ctgtaaattc 3901 agttgaattt tgatatctac ccattttct gtcatccta tagttcactt tgtattaaat 3961 tgggtttcat ttgggatttg caatgtaaat acgtatttct agttttcata taaagtagtt 4021 cttttataac aaatgaaaag tattttttctt gtatattatt aagtaatgaa tatataagaa 4081 ctgtactctt ctcagcttga gcttacatag gtaaatatca ccaacatctg tccttagaaa 4141 ggaccatctc atgttttttt tcttgctatg acttgtgtat tttcttgcat cctccctaga 4201 cttccctatt tcgctttctc ctcggctcac tttctccctt tttatttttc accaaaccat 4261 ttgtagagct acaaaaggta tcctttctta ttttcagtag tcagaatttt atctagaaat 4321 cttttaacac ctttttagtg gttatttcta aaatcactgt caacaataaa tctaaccta 4381 gttgtatccc tcctttcagt attttcact tgttgcccca aatgtgaaag catttcattc 4441 ctttaagagg cctaactcat tcaccctgac agagttcaca aaaagcccac ttaagagtat 4501 acattgctat tatgggagac cacccagaca tctgactaat ggctctgtgc ccacactcca 4561 agacctgtgc cttttagaga agctcacaat gatttaagga ctgtttgaaa cttccaatta 4621 tgtctataat ttatattctt ttgtttacat gatgaaactt tttgttgttg cttgtttgta 4681 tataatacaa tgtgtacatg tatctttttc tcgattcaaa tcttaaccct taggactctg 4741 gtatttttga tctggcaacc atatttctgg aagttgagat gtttcagctt gaagaaccaa 4801 aacagaagga atatgtacaa agaataaatt ttctgctcac gatgagttta gtgtgtaaag 4861 tttagagaca tctgactttg atagctaaat taaaccaaac cctattgaag aattgaatat 4921 atgctacttc aagaaactaa attgatctcg tagaattatc ttaataaaat aatggctata 4981 atttctctgc aaaatcagat gtcagcataa gcgatggata atacctaata aactgccctc 5041 agtaaatcca tggttaataa atgtggtttc tacattaaaa aaaaaaaaaa aaaaaaaaaa 5101 a
```

Sequences of siRNA targeting Eg5/KSP including AD-12115 are described in U.S. patent application Ser. No. 11/694,215 filed Mar. 30, 2007 (now U.S. Pat. No. 7,718,629) and U.S. divisional patent application Ser. No. 12/754,110, filed Apr. 5, 2010 (US patent application publication no. 20110015250). The contents of these applications are incorporated by reference for all purposes. In particular, the sequences of the siRNA disclosed in these applications, e.g., Tables 1 and 2, are incorporated by reference for all purposes. The siRNA were synthesized and assayed for activity as described.

dsRNA Targeting the VEGF Gene

Four hundred target sequences were identified within exons 1-5 of the VEGF-A121 mRNA sequence. The mRNA reference sequence was NM_003376.

```
human VEGF-A121 mRNA sequence. reference transcript is: NM_003376.
                                                         (SEQ ID NO: 12)
   1 augaacuuuc ugcugucuug ggugcauugg agccuugccu ugcugcucua ccuccaccau 61 gccaaguggu cccaggcugc acccauggca gaaggaggag ggcagaauca ucacgaagug
```

```
 12 gugaaguuca uggaugucua ucagcgcagc uacugccauc caaucgagac ccugguggac 181 aucuuccagg aguacccuga ugagaucgag uacaucuuca agccauccug ugugccccug 241 augcgaugcg ggggcugcug caaugacgag ggccuggagu gugugcccac ugaggagucc 301 aacaucacca ugcagauuau gcggaucaaa ccucaccaag gccagcacau aggagagaug 361 agcuuccuac agcacaacaa augugaaugc agaccaaaga aagauagagc aagacaagaa 421 aaaugugaca agccgaggcg guga
```

Sequences of siRNA targeting VEGF, including AD-3133, are described in U.S. patent application Ser. No. 11/078,073 filed Mar. 11, 2005 (US Patent publication no 2006-0094032) and US continuation-in-part patent application Ser. No. 12/754,110, filed Jan. 25, 2006 (US patent application publication no. 2006-0223770). The contents of these applications are incorporated by reference for all purposes. In particular, the sequences of the siRNA disclosed in these applications, e.g., Tables 1 and 2, are incorporated by reference for all purposes. The siRNA were synthesized and assayed for activity as described.

Example 2

Eg5 siRNA In Vitro Screening Via Cell Proliferation

As silencing of Eg5 has been shown to cause mitotic arrest (Weil, D, et al [2002] Biotechniques 33: 1244-8), a cell viability assay was used for siRNA activity screening. siRNA duplexes targeting Eg5 were tested for their effect on inhibition of growth of HeLa cells. Results are provided in Ser. No. 11/694,215 filed Mar. 30, 2007 (now U.S. Pat. No. 7,718,629). Duplex AL-DP-6249 showed the lowest IC50 for inhibition of cell proliferation.

Example 3

Eg5 siRNA In Vitro Screening Via mRNA Inhibition siRNA duplexes targeting Eg5 were tested for their effect on KSP mRNA levels in HeLA S3 cells. Results are provided in Ser. No. 11/694,215 filed Mar. 30, 2007 (now U.S. Pat. No. 7,718,629). Duplex AD-12115 showed a strong reduction of KSP mRNA response, having an IC20 of 0.60 and 0.41 pM, an IC50 of 3.79 and 3.39 µM, and an IC80 of 23.45 and 23.45 pM.

Example 4

Silencing of Liver Eg5/KSP in Juvenile Rats Following Single-Bolus Administration of LNP01 Formulated siRNA From birth until approximately 23 days of age, Eg5/KSP expression can be detected in the growing rat liver. Target silencing with a formulated Eg5/KSP siRNA was evaluated in juvenile rats using duplex AD-6248. The sequence of AD-6248 and results are provided in Ser. No. 11/694,215 filed Mar. 30, 2007 (now U.S. Pat. No. 7,718,629).

A statistically significant reduction in liver Eg5/KSP mRNA was obtained following treatment with formulated AD6248 at a dose of 10 mg/kg.

Example 5

Silencing of Rat Liver VEGF Following Intravenous Infusion of LNP01 Formulated VSP A "lipidoid" formulation comprising an equimolar mixture of two siRNAs was administered to rats. As used herein, VSP refers to a composition having two siRNAs, one directed to Eg5/KSP and one directed to VEGF. For this experiment the duplex AD3133 directed towards VEGF and AD12115 directed towards Eg5/KSP were used. Since Eg5/KSP expression is nearly undetectable in the adult rat liver, only VEGF levels were measured following siRNA treatment.

| | | siRNA duplexes administered (VSP) | |
|---|---|---|---|
| Duplex ID | Target | Sense (5' to 3') | Antisense (5' to 3') |
| AD12115 | Eg5/KSP | ucGAGAAucuAAAcuAAcuTsT (SEQ ID NO: 1) | AGUuAGUUuAGAUUCUCGATsT (SEQ ID NO: 2) |
| AD3133 | VEGF | GcAcAuAGGAGAGAuGAGCUsU (SEQ ID NO: 3) | AAGCUcAUCUCUCCuAuGuGCusG (SEQ ID NO: 4) |

Key A, G, C, U-ribonucleotides; c, u-2'-O-Me ribonucleotides; s-phosphorothioate.

Unmodified versions of each strand and the targets for each siRNA are as follows

| Eg5/KSP | unmod sense | 5' UCGAGAAUCUAAACUAACUTT 3' | SEQ ID NO: 5 |
|---|---|---|---|
| | unmod antisense | 3' TTAGUCCUUAGAUUUGAUUGA 5' | SEQ ID NO: 6 |
| | target | 5' UCGAGAAUCUAAACUAACU 3' | SEQ ID NO: 7 |

-continued

| VEGF | unmod sense | 5' GCACAUAGGAGAGAUGAGCUU 3' | SEQ ID NO: 8 |
| --- | --- | --- | --- |
| | unmod antisense | 3' GUCGUGUAUCCUCUCUACUCGAA 5' | SEQ ID NO: 9 |
| | target | 5' GCACAUAGGAGAGAUGAGCUU 3' | SEQ ID NO: 10 |

Methods

Dosing of Animals.

Adult, female Sprague-Dawley rats were administered lipidoid ("LNP01") formulated siRNA by a two-hour infusion into the femoral vein. Groups of four animals received doses of 5, 10 and 15 milligrams per kilogram (mg/kg) body-weight of formulated siRNA. Dose level refers to the total amount of siRNA duplex administered in the formulation. A fourth group received phosphate-buffered saline. Animals were sacrificed 72 hours after the end of the siRNA infusion. Livers were dissected, flash frozen in liquid Nitrogen and pulverized into powders.

Formulation Procedure

The lipidoid ND98.4HCl (MW 1487) (Formula I, above), Cholesterol (Sigma-Aldrich), and PEG-Ceramide C16 (Avanti Polar Lipids) were used to prepare lipid-siRNA nanoparticles. Stock solutions of each in ethanol were prepared: ND98, 133 mg/mL; Cholesterol, 25 mg/mL, PEG-Ceramide C16, 100 mg/mL. ND98, Cholesterol, and PEG-Ceramide C16 stock solutions were then combined in a 42:48:10 molar ratio. Combined lipid solution was mixed rapidly with aqueous siRNA (in sodium acetate pH 5) such that the final ethanol concentration was 35-45% and the final sodium acetate concentration was 100-300 mM. Lipid-siRNA nanoparticles formed spontaneously upon mixing. Depending on the desired particle size distribution, the resultant nanoparticle mixture was in some cases extruded through a polycarbonate membrane (100 nm cut-off) using a thermobarrel extruder (Lipex Extruder, Northern Lipids, Inc). In other cases, the extrusion step was omitted. Ethanol removal and simultaneous buffer exchange was accomplished by either dialysis or tangential flow filtration. Buffer was exchanged to phosphate buffered saline (PBS) pH 7.2.

Characterization of Formulations

Formulations prepared by either the standard or extrusion-free method are characterized in a similar manner. Formulations are first characterized by visual inspection. They should be whitish translucent solutions free from aggregates or sediment. Particle size and particle size distribution of lipid-nanoparticles are measured by dynamic light scattering using a Malvern Zetasizer Nano ZS (Malvern, USA). Particles should be 20-300 nm, and ideally, 40-100 nm in size. The particle size distribution should be unimodal. The total siRNA concentration in the formulation, as well as the entrapped fraction, is estimated using a dye exclusion assay. A sample of the formulated siRNA is incubated with the RNA-binding dye Ribogreen (Molecular Probes) in the presence or absence of a formulation disrupting surfactant, 0.5% Triton-X100. The total siRNA in the formulation is determined by the signal from the sample containing the surfactant, relative to a standard curve. The entrapped fraction is determined by subtracting the "free" siRNA content (as measured by the signal in the absence of surfactant) from the total siRNA content. Percent entrapped siRNA is typically >85%. For SNALP formulation, the particle size is at least 30 nm, at least 40 nm, at least 50 nm, at least 60 nm, at least 70 nm, at least 80 nm, at least 90 nm, at least 100 nm, at least 110 nm, and at least 120 nm. The preferred range is about at least 50 nm to about at least 110 nm, preferably about at least 60 nm to about at least 100 nm, most preferably about at least 80 nm to about at least 90 nm. In one example, each of the particle size comprises at least about 1:1 ratio of Eg5 dsRNA to VEGF dsRNA.

mRNA Measurements.

Samples of each liver powder (approximately ten milligrams) were homogenized in tissue lysis buffer containing proteinase K. Levels of VEGF and GAPDH mRNA were measured in triplicate for each sample using the Quantigene branched DNA assay (GenoSpectra). Mean values for VEGF were normalized to mean GAPDH values for each sample. Group means were determined and normalized to the PBS group for each experiment.

Protein Measurements.

Samples of each liver powder (approximately 60 milligrams) were homogenized in 1 ml RIPA buffer. Total protein concentrations were determined using the Micro BCA protein assay kit (Pierce). Samples of total protein from each animal was used to determine VEGF protein levels using a VEGF ELISA assay (R&D systems). Group means were determined and normalized to the PBS group for each experiment.

Statistical Analysis.

Significance was determined by ANOVA followed by the Tukey post-hoc test

Results

Data Summary

Mean values (±standard deviation) for mRNA (VEGF/GAPDH) and protein (rel. VEGF) are shown for each treatment group. Statistical significance (p value) versus the PBS group for each experiment is shown.

TABLE 1

| | VEGF/GAPDH | p value | rel VEGF | p value |
| --- | --- | --- | --- | --- |
| PBS | 1.0 ± 0.17 | | 1.0 ± 0.17 | |
| 5 mg/kg | 0.74 ± 0.12 | <0.05 | 0.23 ± 0.03 | <0.001 |
| 10 mg/kg | 0.65 ± 0.12 | <0.005 | 0.22 ± 0.03 | <0.001 |
| 15 mg/kg | 0.49 ± 0.17 | <0.001 | 0.20 ± 0.04 | <0.001 |

Statistically significant reductions in liver VEGF mRNA and protein were measured at all three siRNA dose levels.

Example 6

Assessment of VSP SNALP in Mouse Models of Human Hepatic Tumors

These studies utilized a VSP siRNA cocktail containing dsRNAs targeting KSP/Eg5 and dsRNAs targeting VEGF. As used herein, VSP refers to a composition having two siRNAs, one directed to Eg5/KSP and one directed to VEGF. For this experiment the duplexes AD3133 (directed towards VEGF) and AD12115 (directed towards Eg5/KSP) were used. The siRNA cocktail was formulated in SNALPs.

The maximum study size utilized 20-25 mice. To test the efficacy of the siRNA SNALP cocktail to treat liver cancer, 1×10^6 tumor cells were injected directly into the left lateral lobe of test mice. The incisions were closed by sutures, and the mice allowed to recover for 2-5 hours. The mice were fully recovered within 48-72 hours. The SNALP siRNA treatment was initiated 8-11 days after tumor seeding.

The SNALP formulations utilized were (i) VSP (KSP+VEGF siRNA cocktail (1:1 molar ratio)); (ii) KSP (KSP+Luc siRNA cocktail); and (iii) VEGF (VEGF+Luc siRNA cocktail). All formulations contained equal amounts (mg) of each active siRNA. All mice received a total siRNA/lipid dose, and each cocktail was formulated into 1:57 cDMA SNALP (1.4% PEG-cDMA; 57.1% DLinDMA; 7.1% DPPC; and 34.3% cholesterol), 6:1 lipid:drug using original citrate buffer conditions.

Human Hep3B Study A: Anti-Tumor Activity of VSP-SNALP

Human Hepatoma Hep3B tumors were established in scid/beige mice by intrahepatic seeding. Group A (n=6) animals were administered PBS; Group B (n=6) animals were administered VSP SNALP; Group C (n=5) animals were administered KSP/Luc SNALP; and Group D (n=5) animals were administered VEGF/Luc SNALP.

SNALP treatment was initiated eight days after tumor seeding. The SNALP was dosed at 3 mg/kg total siRNA, twice weekly (Monday and Thursday), for a total of six doses (cumulative 18 mg/kg siRNA). The final dose was administered at day 25, and the terminal endpoint was at day 27.

Tumor burden was assayed by (a) body weight; (b) liver weight; (c) visual inspection+photography at day 27; (d) human-specific mRNA analysis; and (e) blood alpha-fetoprotein levels measured at day 27.

Table 2 below illustrates the results of visual scoring of tumor burden measured in the seeded (left lateral) liver lobe. Score: "−"=no visible tumor; "+"=evidence of tumor tissue at injection site; "++"=Discrete tumor nodule protruding from liver lobe; "+++"=large tumor protruding on both sides of liver lobe; "++++"=large tumor, multiple nodules throughout liver lobe.

TABLE 2

| | Mouse | Tumor Burden |
|---|---|---|
| Group A: PBS, day 27 | 1 | ++++ |
| | 2 | ++++ |
| | 3 | ++ |
| | 4 | +++ |
| | 5 | ++++ |
| | 6 | ++++ |
| Group B: VSP | 1 | + |
| (VEGF + KSP/Eg5, d. 27 | 2 | − |
| | 3 | − |
| | 4 | − |
| | 5 | ++ |
| | 6 | − |
| Group C: KSP | 1 | + |
| (Luc + KSP), d. 27 | 2 | ++ |
| | 3 | − |
| | 4 | + |
| | 5 | ++ |
| Group D: VEGF | 1 | ++++ |
| (Luc + VEGF), d. 27 | 2 | − |
| | 3 | ++++ |
| | 4 | +++ |
| | 5 | ++++ |

Liver weights, as percentage of body weight, are shown in FIG. 1.

Body weights are shown in FIGS. 2A-2D.

From this study, the following conclusions were made. (1) VSP SNALP demonstrated potent anti-tumor effects in Hep3B 1H model; (2) the anti-tumor activity of the VSP cocktail appeared largely associated with the KSP component; (3) anti-KSP activity was confirmed by single dose histological analysis; and (4) VEGF siRNA showed no measurable effect on inhibition of tumor growth in this model.

Human Hep3B Study B: Prolonged Survival with VSP Treatment

In a second Hep3B study, human hepatoma Hep3B tumors were established by intrahepatic seeding into scid/beige mice. These mice were deficient for lymphocytes and natural killer (NK) cells, which is the minimal scope for immune-mediated anti-tumor effects. Group A (n=6) mice were untreated; Group B (n=6) mice were administered luciferase (luc) 1955 SNALP (Lot No. AP10-02); and Group C (n=7) mice were administered VSP SNALP (Lot No. AP10-01). SNALP was 1:57 cDMA SNALP, and 6:1 lipid:drug.

SNALP treatment was initiated eight days after tumor seeding. SNALP was dosed at 3 mg/kg siRNA, twice weekly (Mondays and Thursdays), for a total of six doses (cumulative 18 mg/kg siRNA). The final dose was delivered at day 25, and the terminal endpoint of the study was at day 27.

Tumor burden was assayed by (1) body weight; (2) visual inspection+photography at day 27; (3) human-specific mRNA analysis; and (4) blood alpha-fetoprotein measured at day 27.

Figure 3:
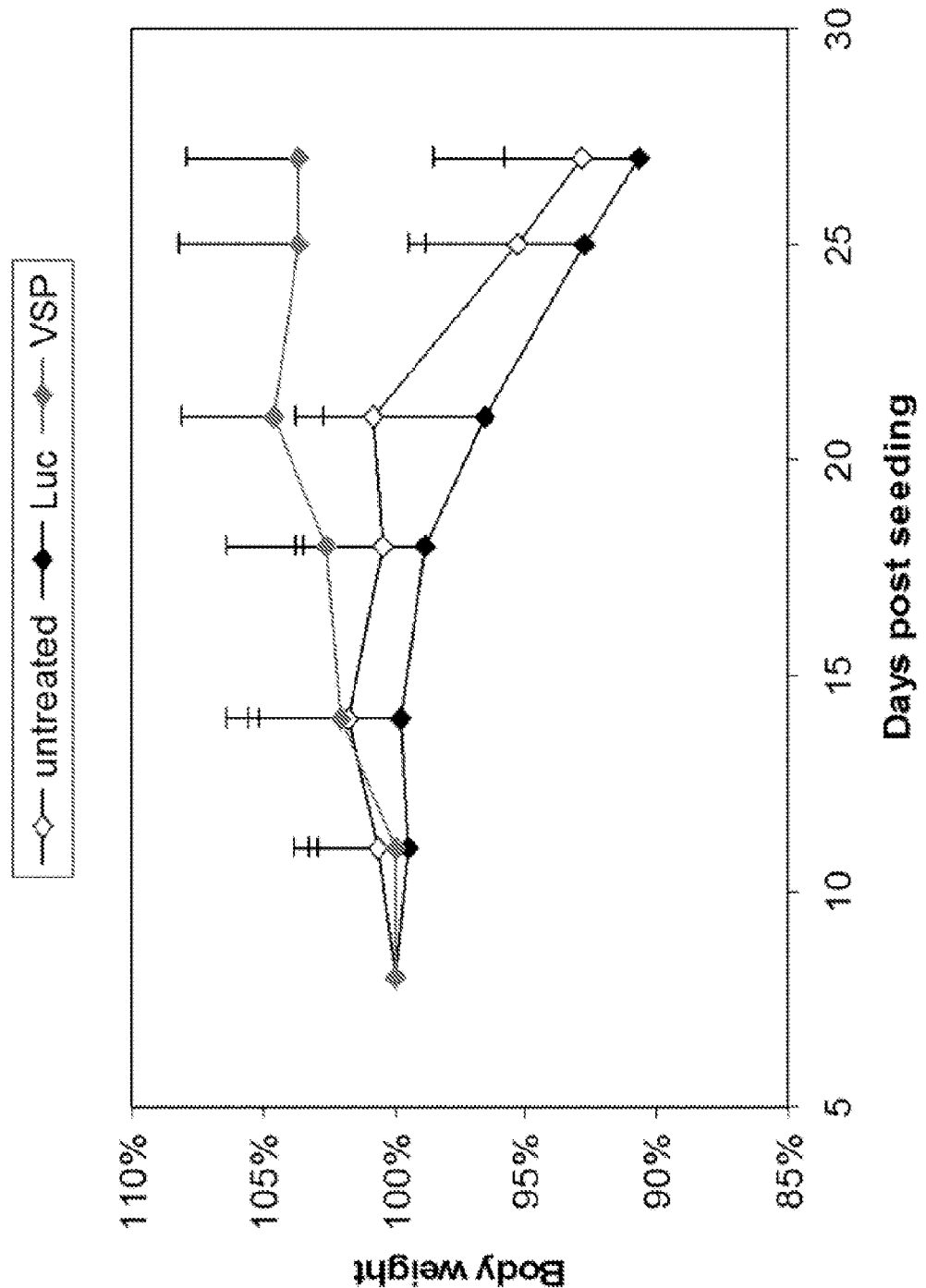
FIG. 3 is a graph showing the effects of SNALP-siRNAs on body weight in a Hep3B mouse model.

Body weights were measured at each day of dosing (days 8, 11, 14, 18, 21, and 25) and on the day of sacrifice (FIG. 3).

TABLE 3

| | Mouse | Tumor Burden by macroscopic observation |
|---|---|---|
| Group A: | A1R | ++ |
| untreated, | A1G | ++++ |
| day 27 | A1W | − |
| | A2R | ++++ |
| | A2G | +++ |
| | A2W | ++++ |
| Group B: | B1R | ++++ |
| 1955 Luc SNALP | B1G | ++++ |
| day 27 | B1W | +++ |
| | B2R | ++ |
| | B2G | +++ |
| | B2W | ++++ |
| Group C: | C1R | − |
| VSP SNALP | C1G | − |
| day 27 | C1B | − |
| | C1W | + |
| | C2R | + |
| | C2G | + |
| | C2W | − |

Score:
"−" = no visible tumor;
"+" = evidence of tumor tissue at injection site;
"++" = Discrete tumor nodule protruding from liver lobe;
"+++" = large tumor protruding on both sides of liver lobe;
"++++" = large tumor, multiple nodules throughout liver lobe.

Figure 4:
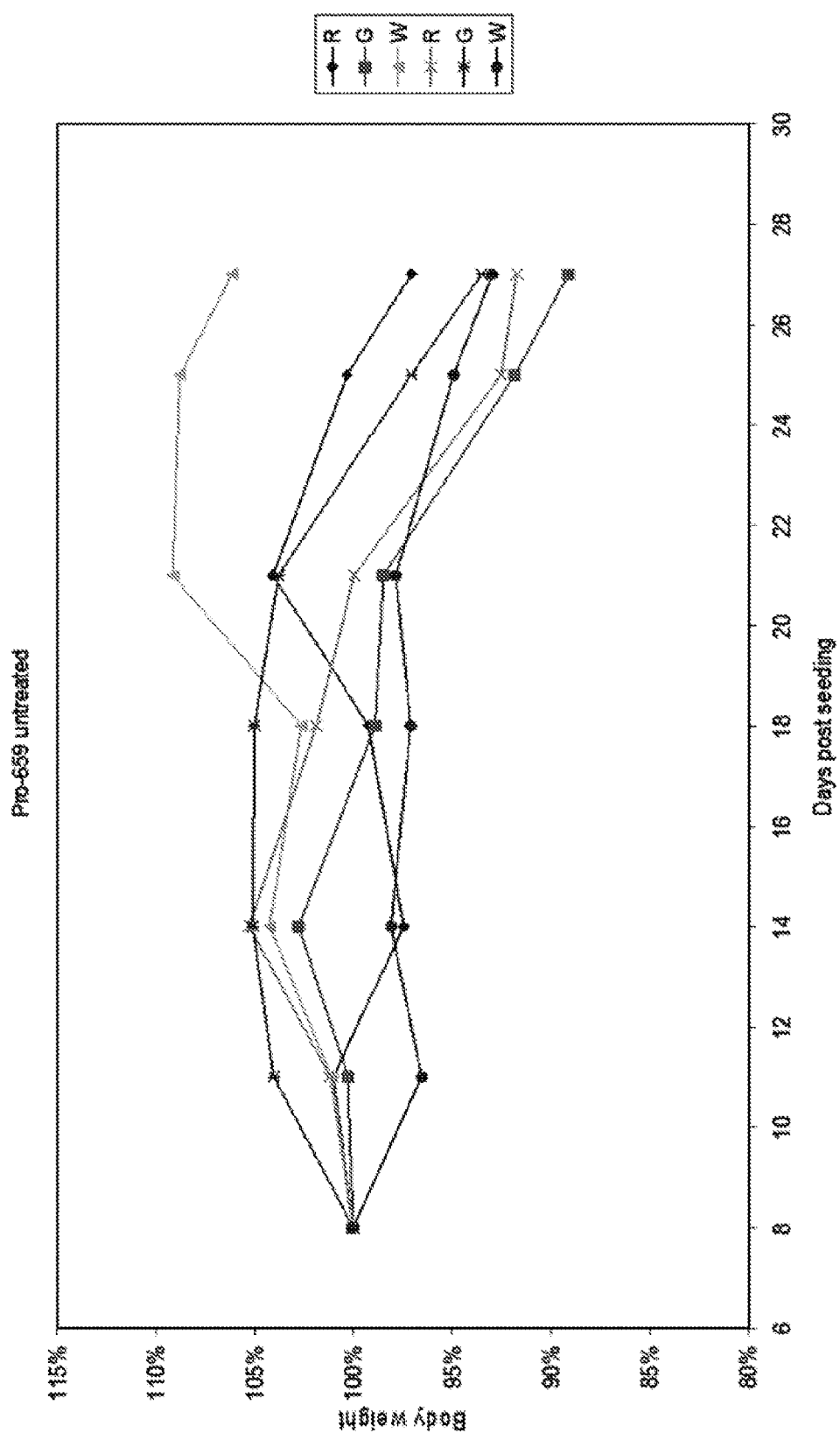
FIG. 4 is a graph showing the body weight in untreated control animals.
Figure 5:
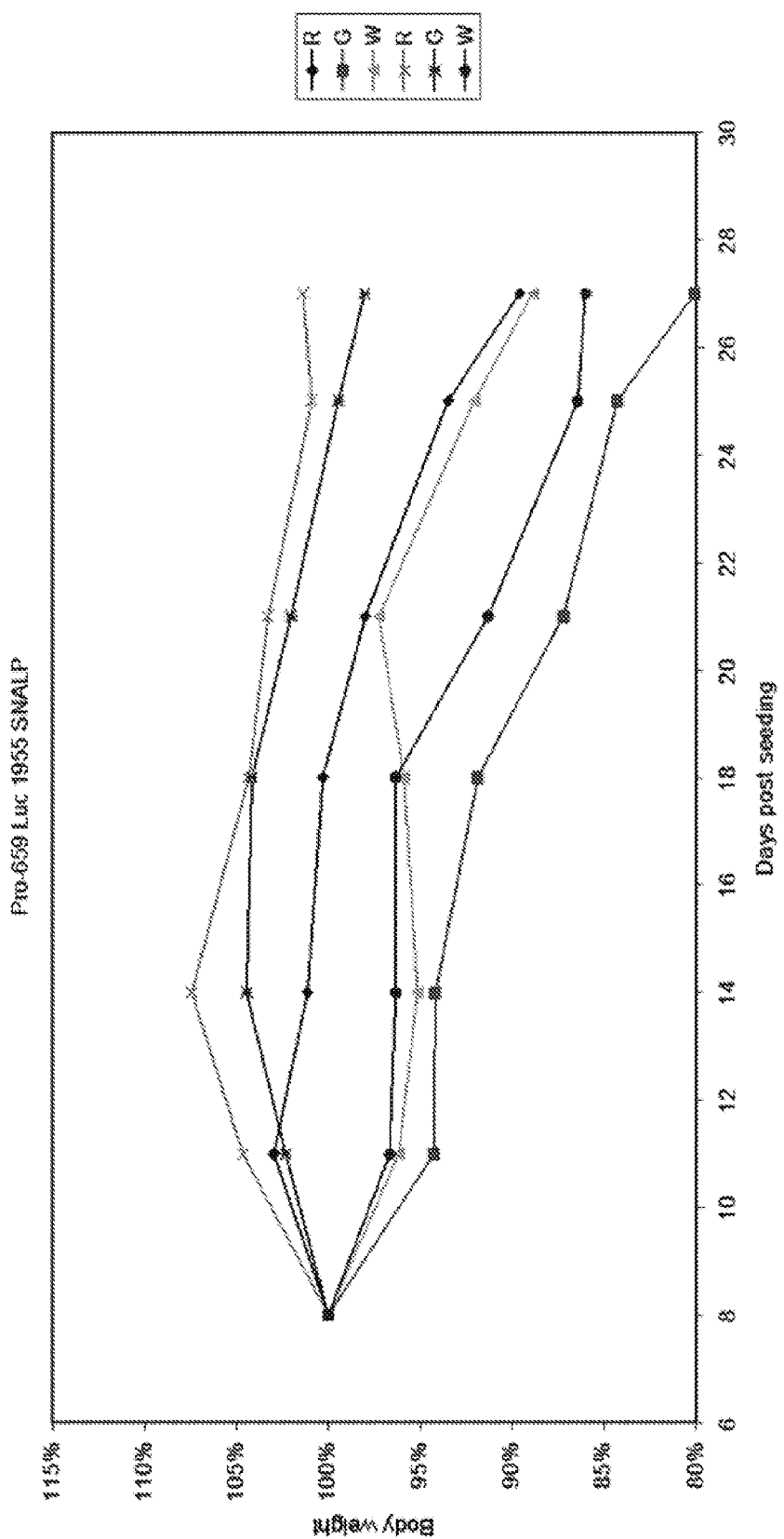
FIG. 5 is a graph showing the effects of control luciferase-SNALP siRNAs on body weight in a Hep3B mouse model.
Figure 6:
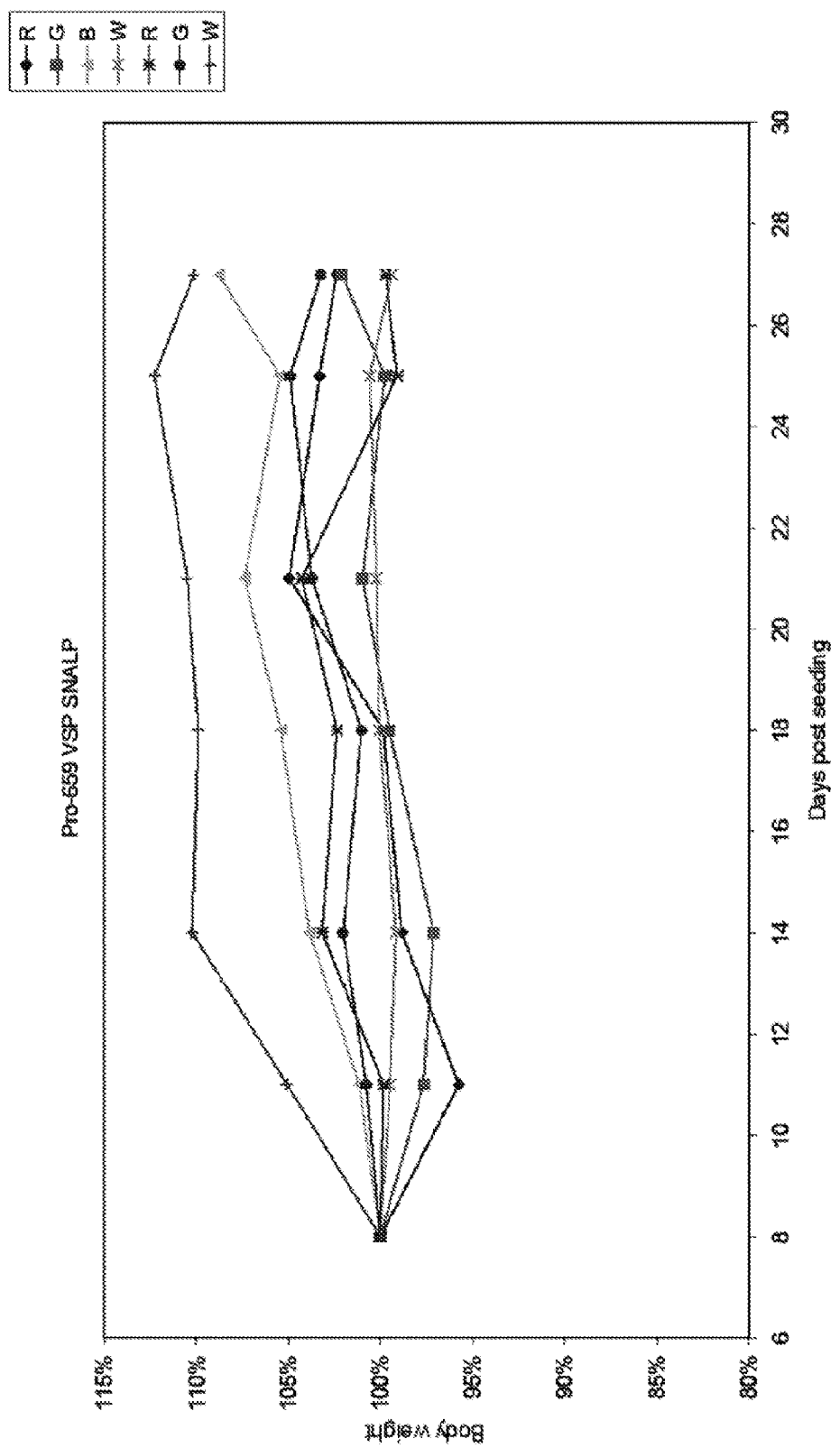
FIG. 6 is a graph showing the effects of VSP-SNALP siRNAs on body weight in a Hep3B mouse model.

The correlation between body weights and tumor burden are shown in FIGS. 4, 5 and 6.

A single dose of VSP SNALP (2 mg/kg) to Hep3B mice also resulted in the formation of mitotic spindles in liver tissue samples examined by histological staining.

Figure 7A:
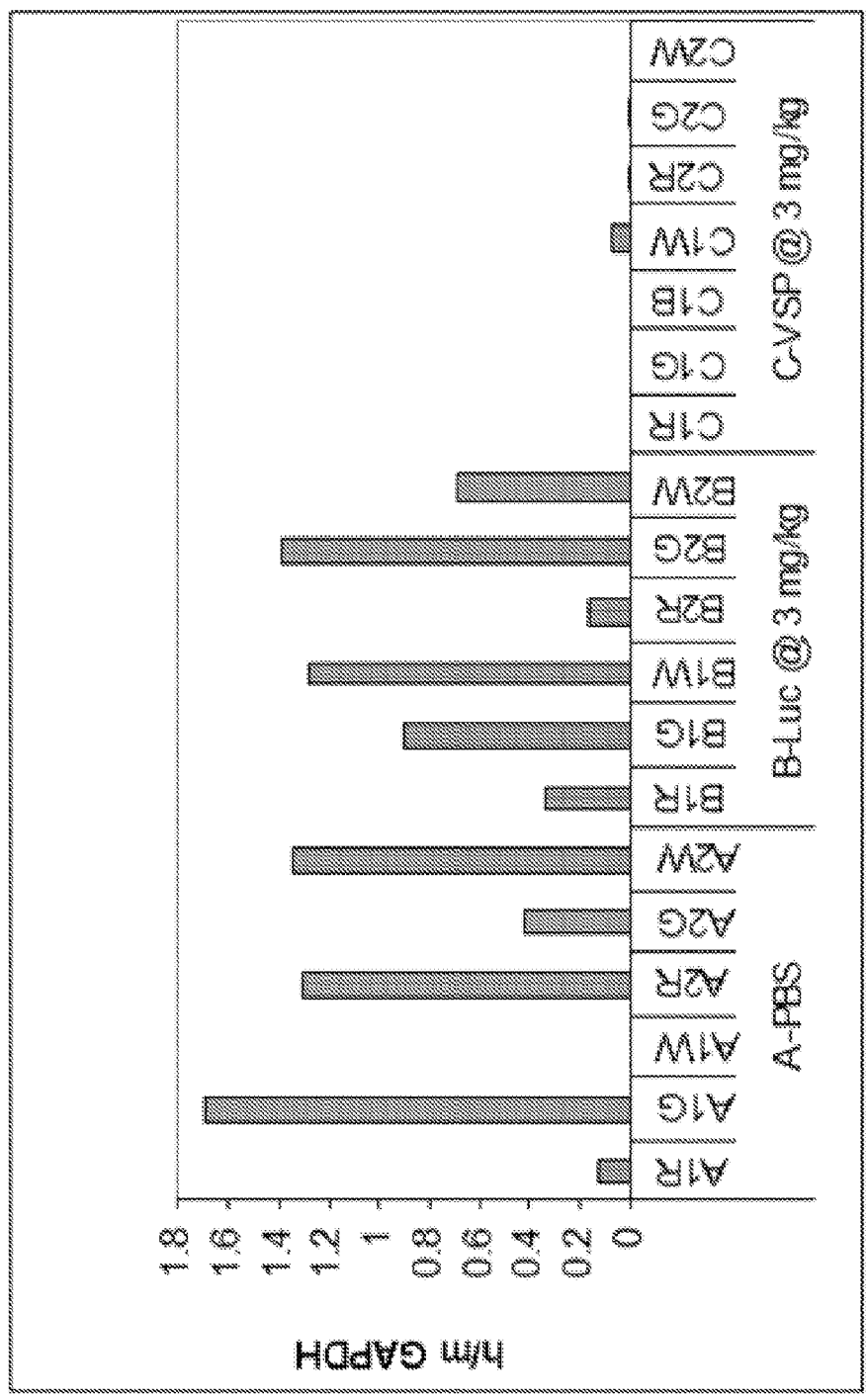
FIG. 7A is a graph showing the effects of SNALP-siRNAs on human GAPDH levels normalized to mouse GAPDH levels in a Hep3B mouse model.

Tumor burden was quantified by quantitative RT-PCR (pRT-PCR) (Taqman). Human GAPDH was normalized to mouse GAPDH via species-specific Taqman assays. Tumor score as shown by macroscopic observation in the table above correlated with GADPH levels (FIG. 7A).

Serum ELISA was performed to measure alpha-fetoprotein (AFP) secreted by the tumor. As described below, if levels of AFP go down after treatment, the tumor is not growing.

Figure 7B:
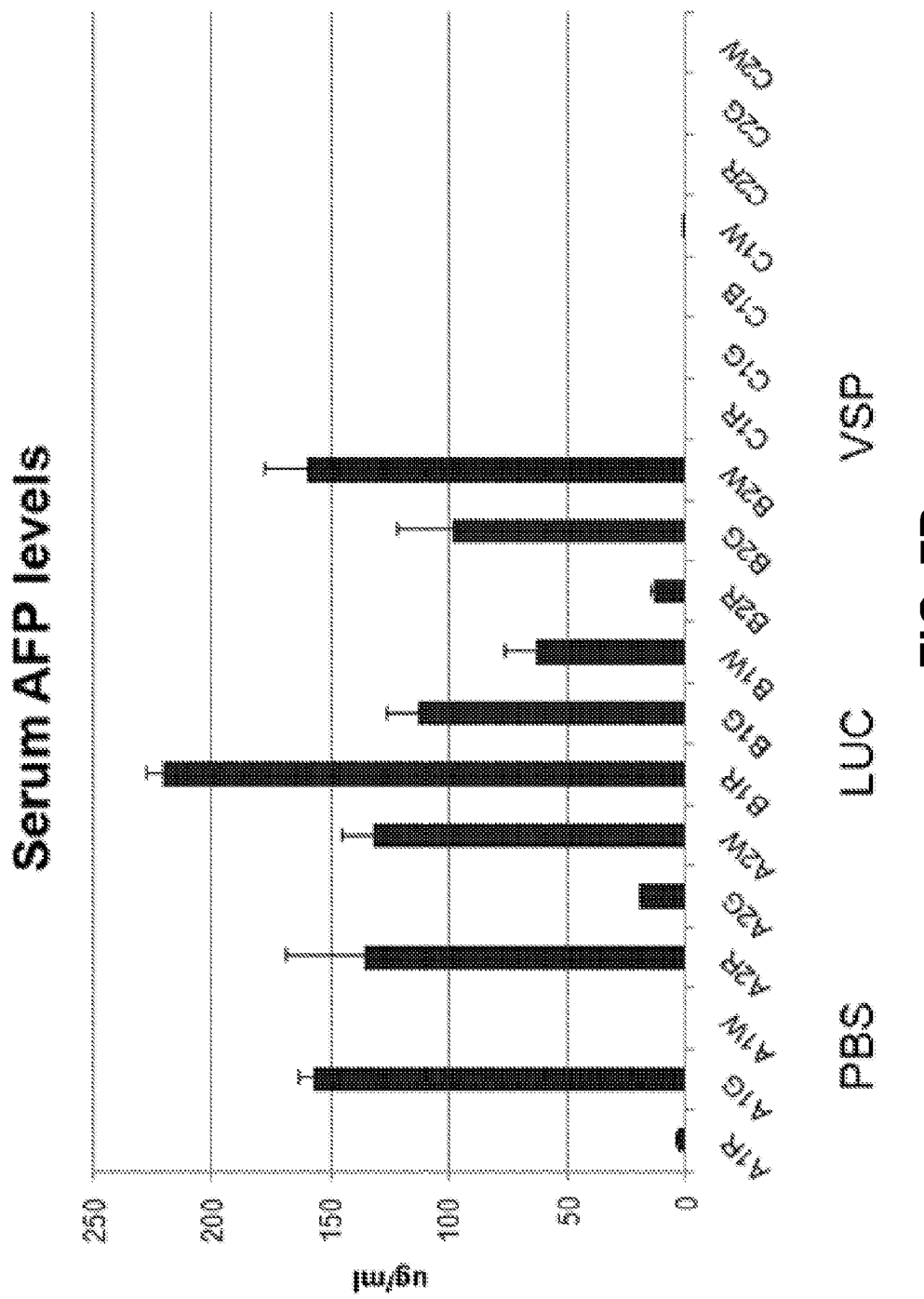
FIG. 7B is a graph showing the effects of SNALP-siRNAs on serum AFP levels as measured by serum ELISA in a Hep3B mouse model.

Treatment with VSP lowered AFP levels in some animals compared to treatment with controls (FIG. 7B).

Human HepB3 Study C:

In a third study, human HCC cells (HepB3) were injected directly into the liver of SCID/beige mice, and treatment was initiated 20 days later. Group A animals were administered PBS; Group B animals were administered 4 mg/kg Luc-1955 SNALP; Group C animals were administered 4 mg/kg SNALP-VSP; Group D animals were administered 2 mg/kg SNALP-VSP; and Group E animals were administered 1 mg/kg SNALP-VSP. Treatment was with a single intravenous (iv) dose, and mice were sacrificed 24 hr. later.

Figure 8:
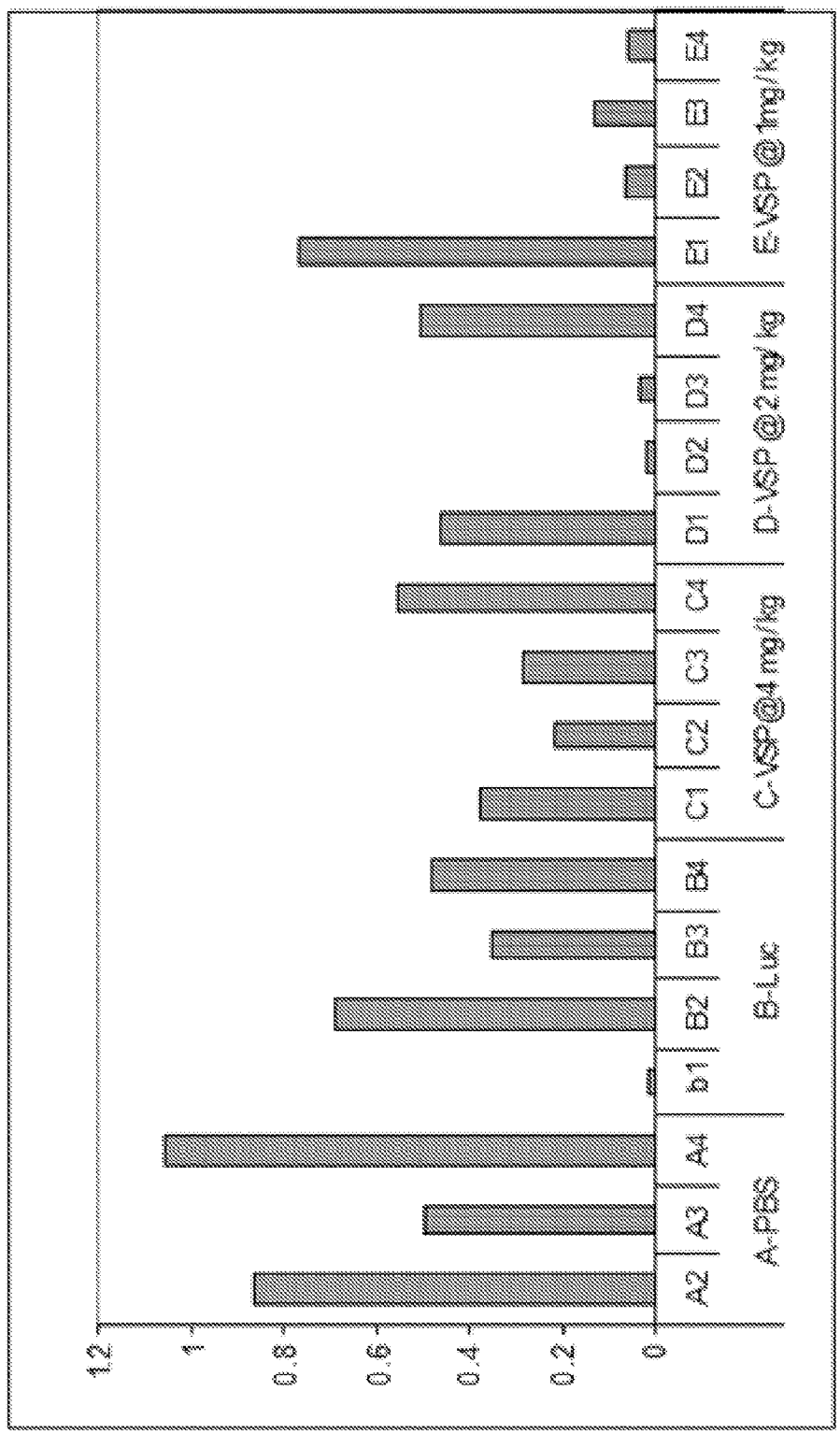
FIG. 8 is a graph showing the effects of SNALP-siRNAs on human GAPDH levels normalized to mouse GAPDH levels in a Hep3B mouse model.

Tumor burden and target silencing was assayed by qRT-PCR (Taqman). Tumor score was also measured visually as described above, and the results are shown in the following table. hGAPDH levels, as shown in FIG. 8, correlates with macroscopic tumor score as shown in the table below.

TABLE 4

|  | Mouse | Tumor Burden by macroscopic observation |
|---|---|---|
| Group A: PBS | A2 | +++ |
|  | A3 | +++ |
|  | A4 | +++ |
| Group B: 4 mg/kg Luc-1955 SNALP | B1 | + |
|  | B2 | +++ |
|  | B3 | +++ |
|  | B4 | +++ |
| Group C: 4 mg/kg SNALP-VSP | C1 | ++ |
|  | C2 | ++ |
|  | C3 | ++ |
|  | C4 | +++ |
| Group D: 2 mg/kg SNALP-VSP | D1 | ++ |
|  | D2 | + |
|  | D3 | + |
|  | D4 | ++ |
| Group E: 1 mg/kg SNALP-VSP | E1 | +++ |
|  | E2 | + |
|  | E3 | ++ |
|  | E4 | + |

Figure 9:
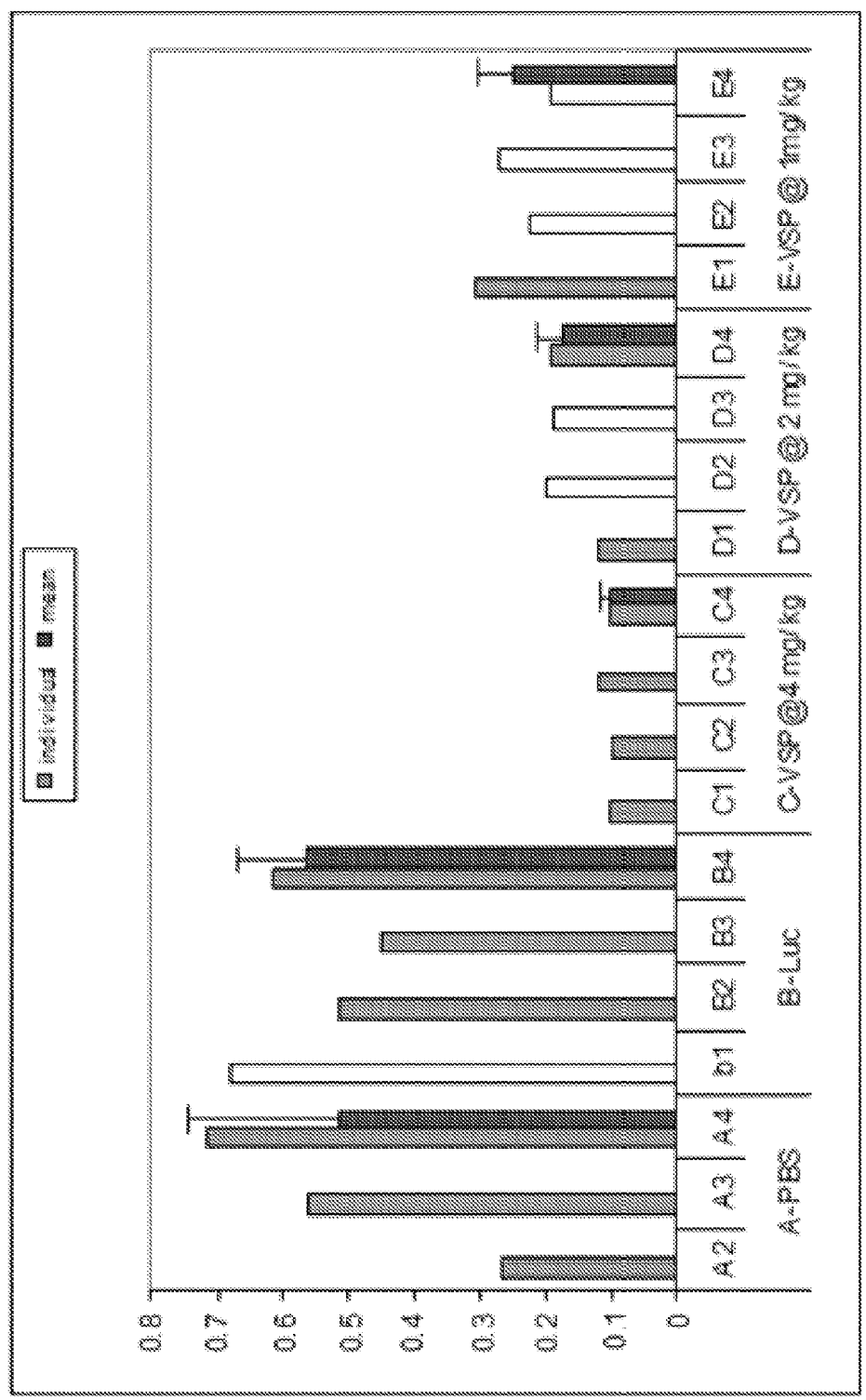
FIG. 9 is a graph showing the effects of SNALP-siRNAs on human KSP levels normalized to human GAPDH levels in a Hep3B mouse model.
Figure 10:
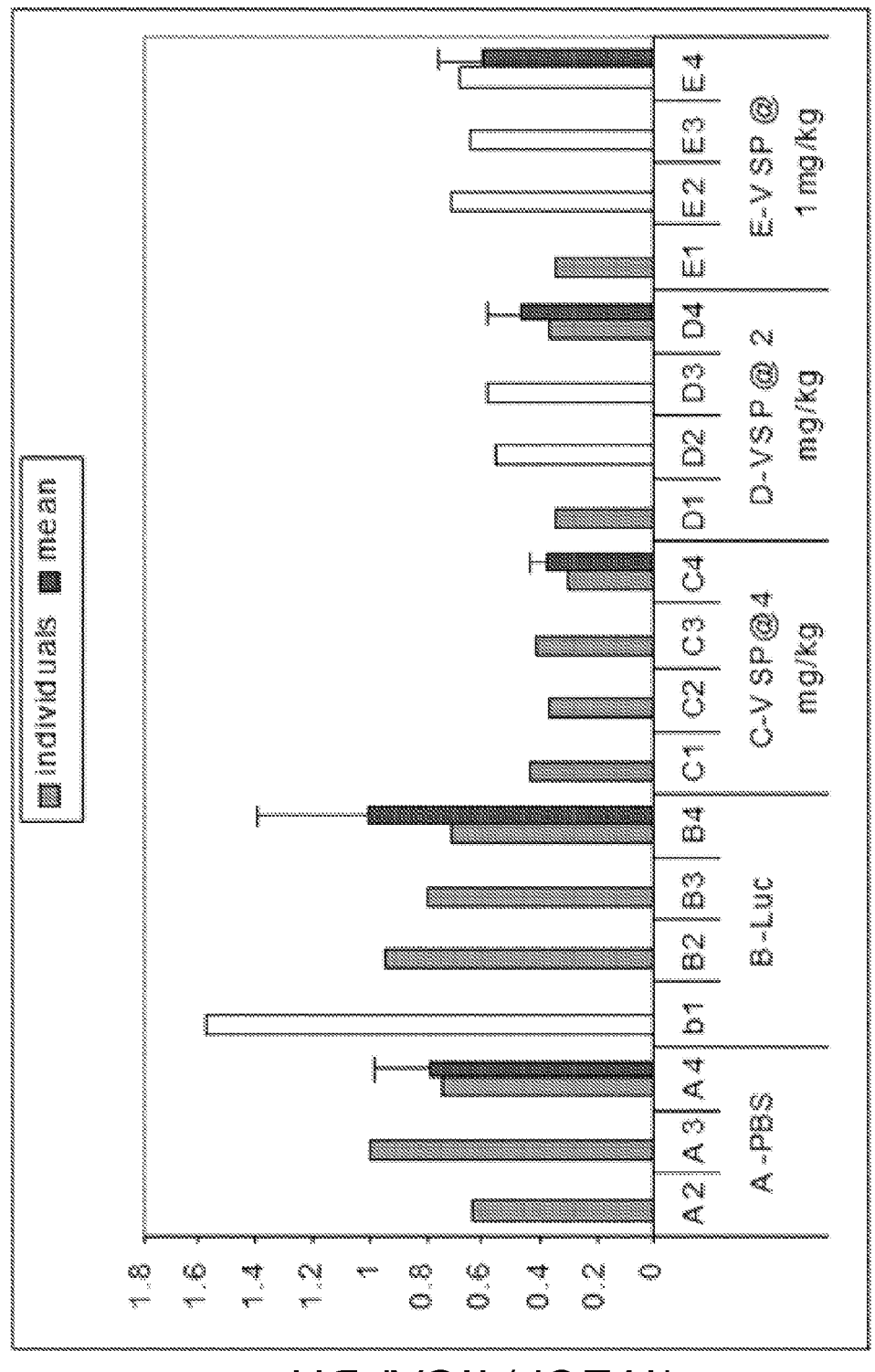
FIG. 10 is a graph showing the effects of SNALP-siRNAs on human VEGF levels normalized to human GAPDH levels in a Hep3B mouse model.

Score:
"+" = variable tumor take/some small tumors;
"++" = Discrete tumor nodule protruding from liver lobe;
"+++" = large tumor protruding on both sides of liver lobe Human (tumor-derived) KSP silencing was assayed by Taqman analysis and the results are shown in FIG. 10. hKSP expression was normalized to hGAPDH. About 80% tumor KSP silencing was observed at 4 mg/kg SNALP-VSP, and efficacy was evident at 1 mg/kg. The clear bars in FIG. 9 represent the results from small (low GAPDH) tumors.

Human (tumor-derived) VEGF silencing was assayed by Taqman analysis and the results are shown in FIG. 10. hVEGF expression was normalized to hGAPDH. About 60% tumor VEGF silencing was observed at 4 mg/kg SNALP-VSP, and efficacy was evident at 1 mg/kg. The clear bars in FIG. 10 represent the results from small (low GAPDH) tumors.

Figure 11A:
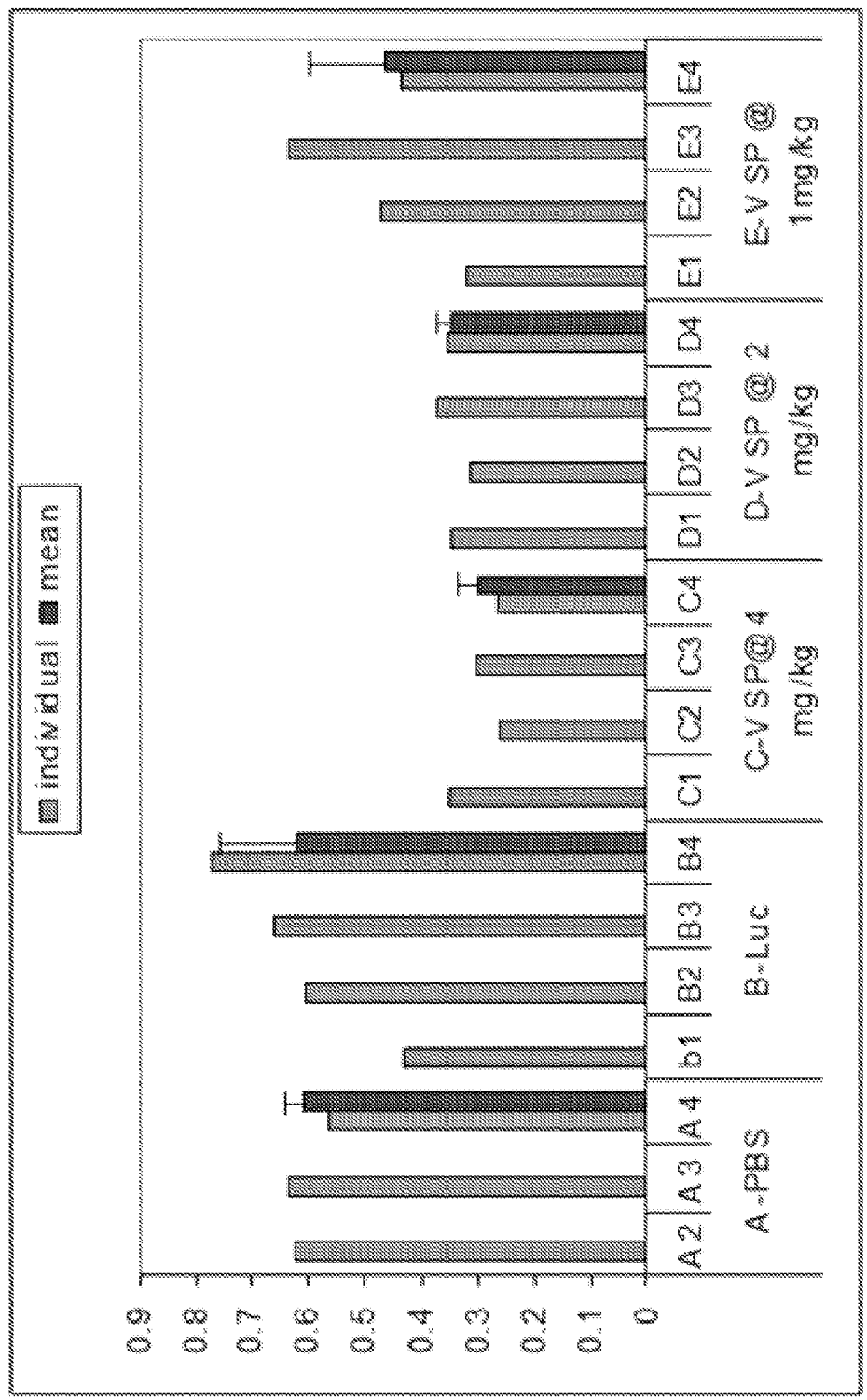
FIG. 11A is a graph showing the effects of SNALP-siRNAs on mouse VEGF levels normalized to human GAPDH levels in a Hep3B mouse model.

Mouse (liver-derived) VEGF silencing was assayed by Taqman analysis and the results are shown in FIG. 11A. mVEGF expression was normalized to hGAPDH. About 50% liver VEGF silencing was observed at 4 mg/kg SNALP-VSP, and efficacy was evident at 1 mg/kg.

Human HepB3 Study D: Contribution of Each dsRNA to Tumor Growth

In a fourth study, human HCC cells (HepB3) were injected directly into the liver of SCID/beige mice, and treatment was initiated 8 days later. Treatment was with intravenous (iv) bolus injections, twice weekly, for a total of six does. The final dose was administered at day 25, and the terminal endpoint was at day 27.

Tumor burden was assayed by gross histology, human-specific mRNA analysis (hGAPDH qPCR), and blood alpha-fetoprotein levels (serum AFP via ELISA).

In Study 1, Group A was treated with PBS, Group B was treated with SNALP-KSP+Luc (3 mg/kg), Group C was treated with SNALP-VEGF+Luc (3 mg/kg), and Group D was treated with ALN-VSP02 (3 mg/kg).

In Study 2, Group A was treated with PBS; Group B was treated with SNALP-KSP+Luc (1 mg/kg), Group C was treated with ALN-VSP02 (1 mg/kg).

Figure 11B:
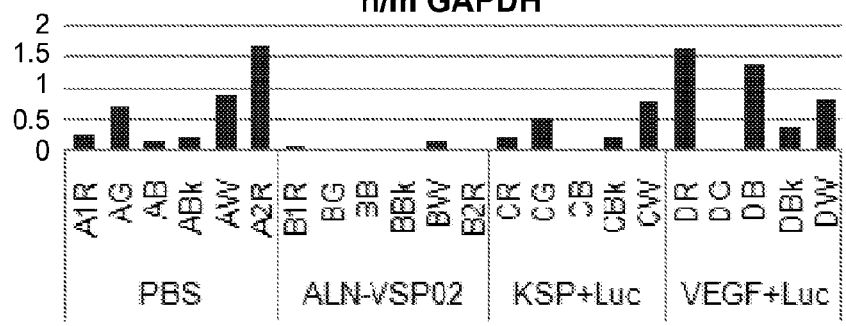
FIG. 11B is a set of graphs showing the effects of SNALP-siRNAs on human GAPDH levels and serum AFP levels in a Hep3B mouse model.
Figure 11B:
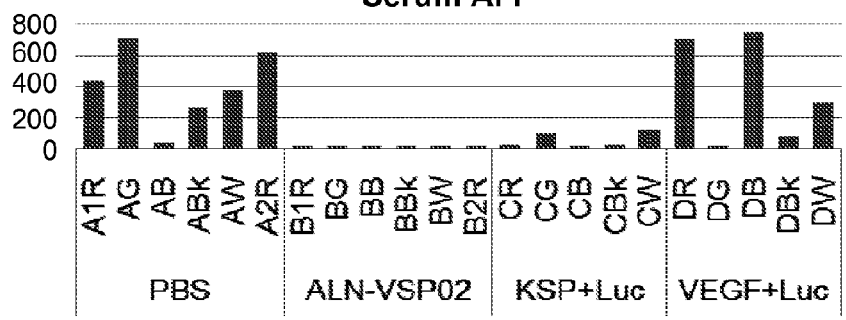
Figure 11B:
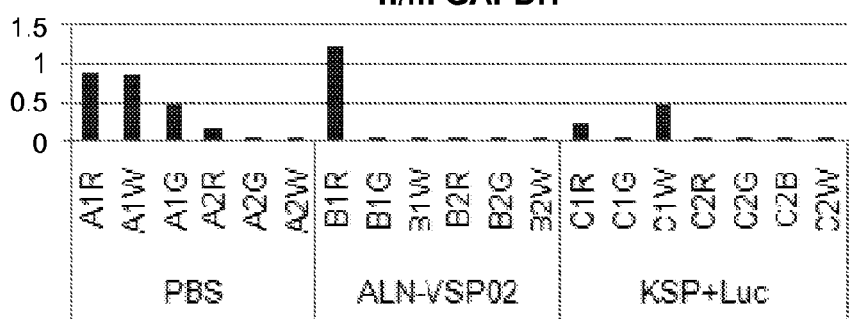
Figure 11B:
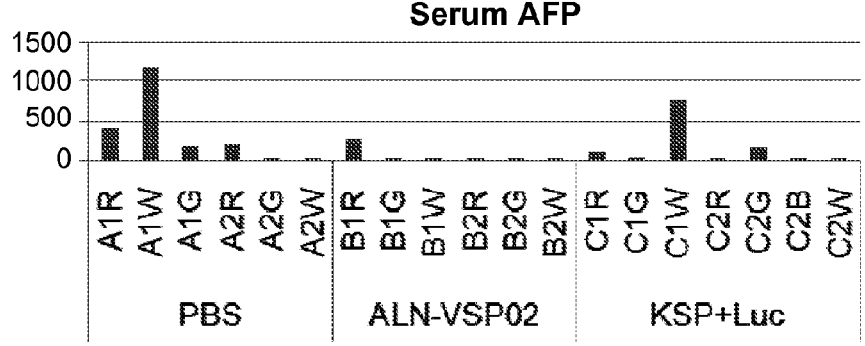

Both GAPDH mRNA levels and serum AFP levels were shown to decrease after treatment with ALN-VSP02 (FIG. 11B).

Histology Studies:

Human hepatoma Hep3B tumors were established by intrahepatic seeding in mice. SNALP treatment was initiated 20 days after tumor seeding. Tumor-bearing mice (three per group) were treated with a single intravenous (IV) dose of (i) VSP SNALP or (ii) control (Luc) SNALP at 2 mg/kg total siRNA.

Liver/tumor samples were collected for conventional H&E histology 24 hours after single SNALP administration.

Large macroscopic tumor nodules (5-10 mm) were evident at necroscopy.

Figures 12A, 12B:
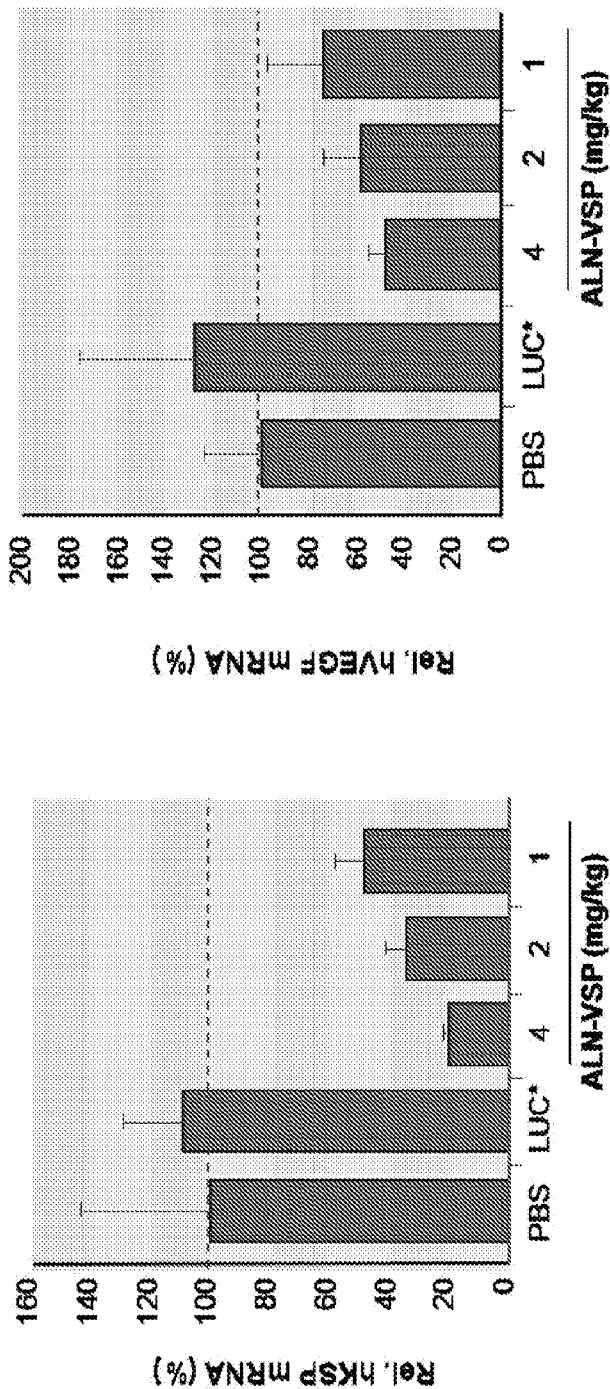
FIGS. 12A-12C are graphs showing the effects of SNALP-siRNAs on tumor KSP, VEGF and GAPDH levels in a Hep3B mouse model.
Figure 12C:
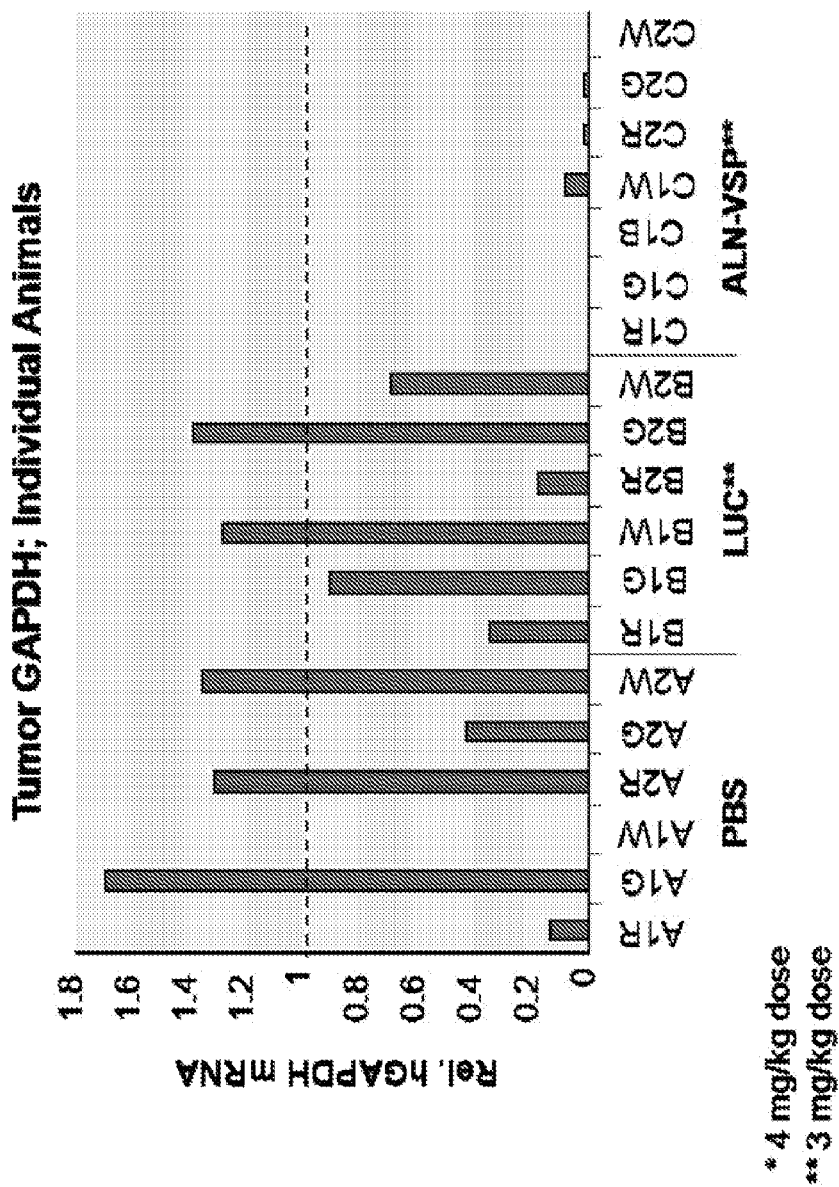

Effect of ALN-VSP in Hep3B Mice:

ALN-VSP (a cocktail of KSP dsRNA and VEGF dsRNA) treatment reduced tumor burden and expression of tumor-derived KSP and VEGF. GAPDH mRNA levels, a measure of tumor burden, were also observed to decline following administration of ALN-VSP dsRNA (see FIGS. 12A-12C). A decrease in tumor burden by visual macroscopic observation was also evident following administration of ALN-VSP.

A single IV bolus injection of ALN-VSP also resulted in mitotic spindle formation that was clearly detected in liver tissue samples from Hep3B mice. This observation indicated cell cycle arrest.

Example 7a

Survival of SNALP-VSP Animals Versus SNALP-Luc Treated Animals

To test the effect of siRNA SNALP on survival rates of cancer subjects, tumors were established by intrahepatic seeding in mice and the mice were treated with SNALP-siRNA. These studies utilized a VSP siRNA cocktail containing dsRNAs targeting KSP/Eg5 and VEGF. Control was dsRNA targeting Luc. The siRNA cocktail was formulated in SNALPs.

Tumor cells (Human Hepatoma Hep3B, 1×10^6) were injected directly into the left lateral lobe of scid/beige mice. These mice were deficient for lymphocytes and natural killer (NK) cells, which is the minimal scope for immune-mediated anti-tumor effects. The incisions were closed by sutures, and the mice allowed to recover for 2-5 hours. The mice were fully recovered within 48-72 hours.

All mice received a total siRNA/lipid intravenous (iv) dose, and each cocktail was formulated into 1:57 cDMA SNALP (1.4% PEG-cDMA; 57.1% DLinDMA; 7.1% DPPC; and 34.3% cholesterol), 6:1 lipid:drug using original citrate buffer conditions.

siRNA-SNALP treatment was initiated on the day indicated below (18 or 26 days) after tumor seeding. siRNA-SNALP were administered twice a week for three weeks after 18 or 26 days at a dose of 4 mg/kg. Survival was monitored and animals were euthanized based on humane surrogate endpoints (e.g., animal body weight, abdominal distension/discoloration, and overall health).

Figure 13A:
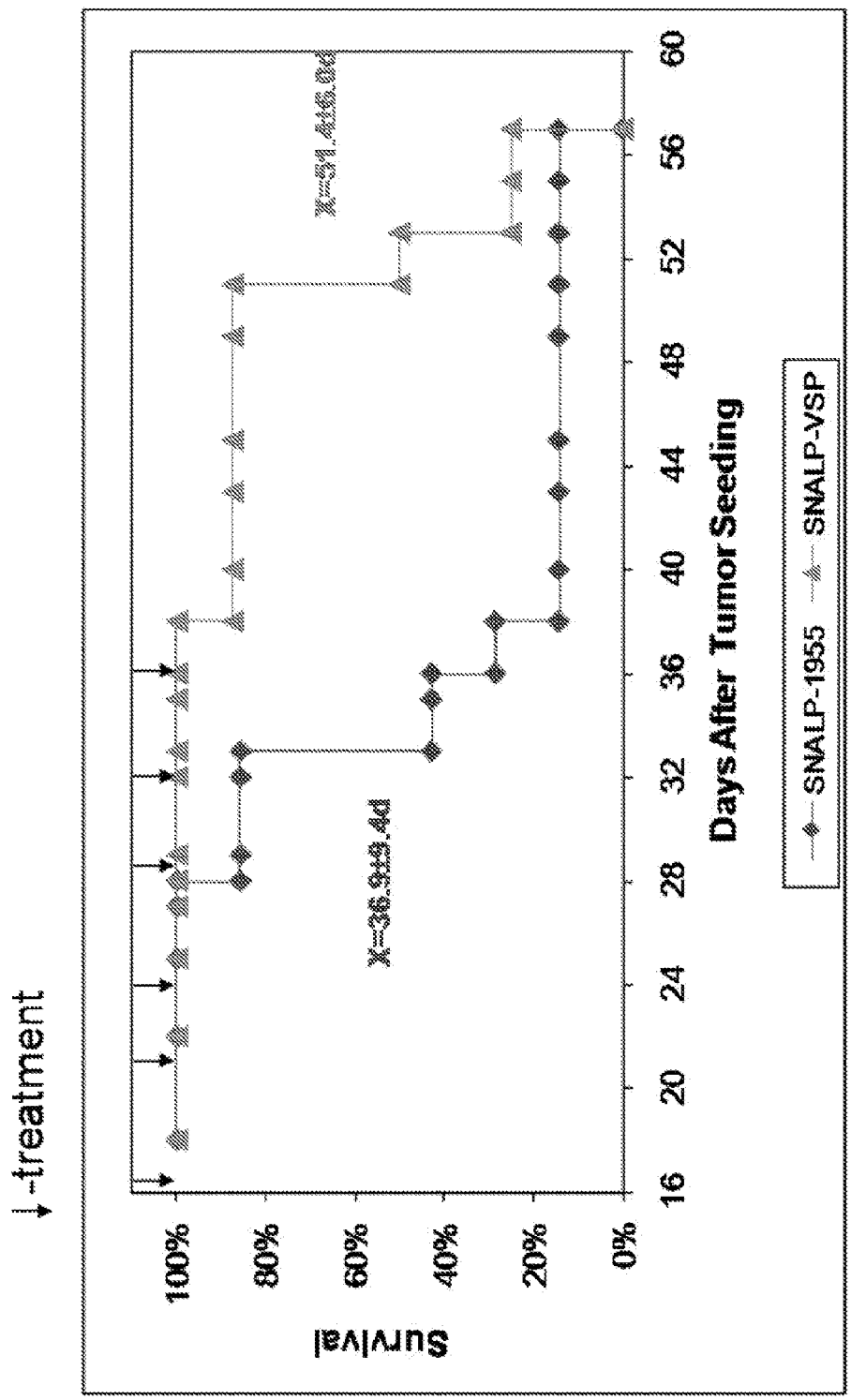
FIG. 13A and FIG. 13B are graphs showing the effects of SNALP-siRNAs on survival in mice with hepatic tumors. Treatment was started at 18 days (FIG. 13A) and 26 days (FIG. 13B) after tumor cell seeding.

The survival data for treatment initiated 18 days after tumor seeing is summarized in Table 5, Table 6, and FIG. 13A.

TABLE 5

Kaplan-Meier (survival) data (% Surviving)

| Day | SNALP-Luc | SNALP-VSP |
| --- | --- | --- |
| 18 | 100% | 100% |
| 22 | 100% | 100% |
| 25 | 100% | 100% |
| 27 | 100% | 100% |
| 28 | 100% | 100% |
| 28 | 86% | 100% |
| 29 | 86% | 100% |
| 32 | 86% | 100% |
| 33 | 86% | 100% |
| 33 | 43% | 100% |
| 35 | 43% | 100% |
| 36 | 43% | 100% |
| 36 | 29% | 100% |
| 38 | 29% | 100% |
| 38 | 14% | 100% |
| 38 | 14% | 88% |
| 40 | 14% | 88% |
| 43 | 14% | 88% |
| 45 | 14% | 88% |
| 49 | 14% | 88% |
| 51 | 14% | 88% |
| 51 | 14% | 50% |
| 53 | 14% | 50% |
| 53 | 14% | 25% |
| 55 | 14% | 25% |
| 57 | 14% | 25% |
| 57 | 0% | 0% |

TABLE 6

Survival in days, for each animal.

| Animal | Treatment group | Survival | |
| --- | --- | --- | --- |
| 1 | SNALP-Luc | 28 | days |
| 2 | SNALP-Luc | 33 | days |
| 3 | SNALP-Luc | 33 | days |
| 4 | SNALP-Luc | 33 | days |
| 5 | SNALP-Luc | 36 | days |
| 6 | SNALP-Luc | 38 | days |
| 7 | SNALP-Luc | 57 | days |
| 8 | SNALP-VSP | 38 | days |
| 9 | SNALP-VSP | 51 | days |
| 10 | SNALP-VSP | 51 | days |
| 11 | SNALP-VSP | 51 | days |
| 12 | SNALP-VSP | 53 | days |
| 13 | SNALP-VSP | 53 | days |
| 14 | SNALP-VSP | 57 | days |
| 15 | SNALP-VSP | 57 | days |

FIG. 13A shows the mean survival of SNALP-VSP animals and SNALP-Luc treated animals versus days after tumor seeding. The mean survival of SNALP-VSP animals was extended by approximately 15 days versus SNALP-Luc treated animals.

TABLE 7

Serum alpha fetoprotein (AFP) concentration, for each animal, at a time pre-treatment and at end of treatment (concentration in µg/ml)

| | | pre-Rx | End of Rx |
| --- | --- | --- | --- |
| 1 | SNALP-Luc | 30.858 | 454.454 |
| 2 | SNALP-Luc | 10.088 | 202.082 |
| 3 | SNALP-Luc | 23.736 | 648.952 |
| 4 | SNALP-Luc | 1.696 | 13.308 |
| 5 | SNALP-Luc | 4.778 | 338.688 |
| 6 | SNALP-Luc | 15.004 | 826.972 |
| 7 | SNALP-Luc | 11.036 | 245.01 |
| 8 | SNALP-VSP | 37.514 | 182.35 |
| 9 | SNALP-VSP | 91.516 | 248.06 |
| 10 | SNALP-VSP | 25.448 | 243.13 |
| 11 | SNALP-VSP | 24.862 | 45.514 |
| 12 | SNALP-VSP | 57.774 | 149.352 |
| 13 | SNALP-VSP | 12.446 | 78.724 |
| 14 | SNALP-VSP | 2.912 | 9.61 |
| 15 | SNALP-VSP | 4.516 | 11.524 |

Figure 14:
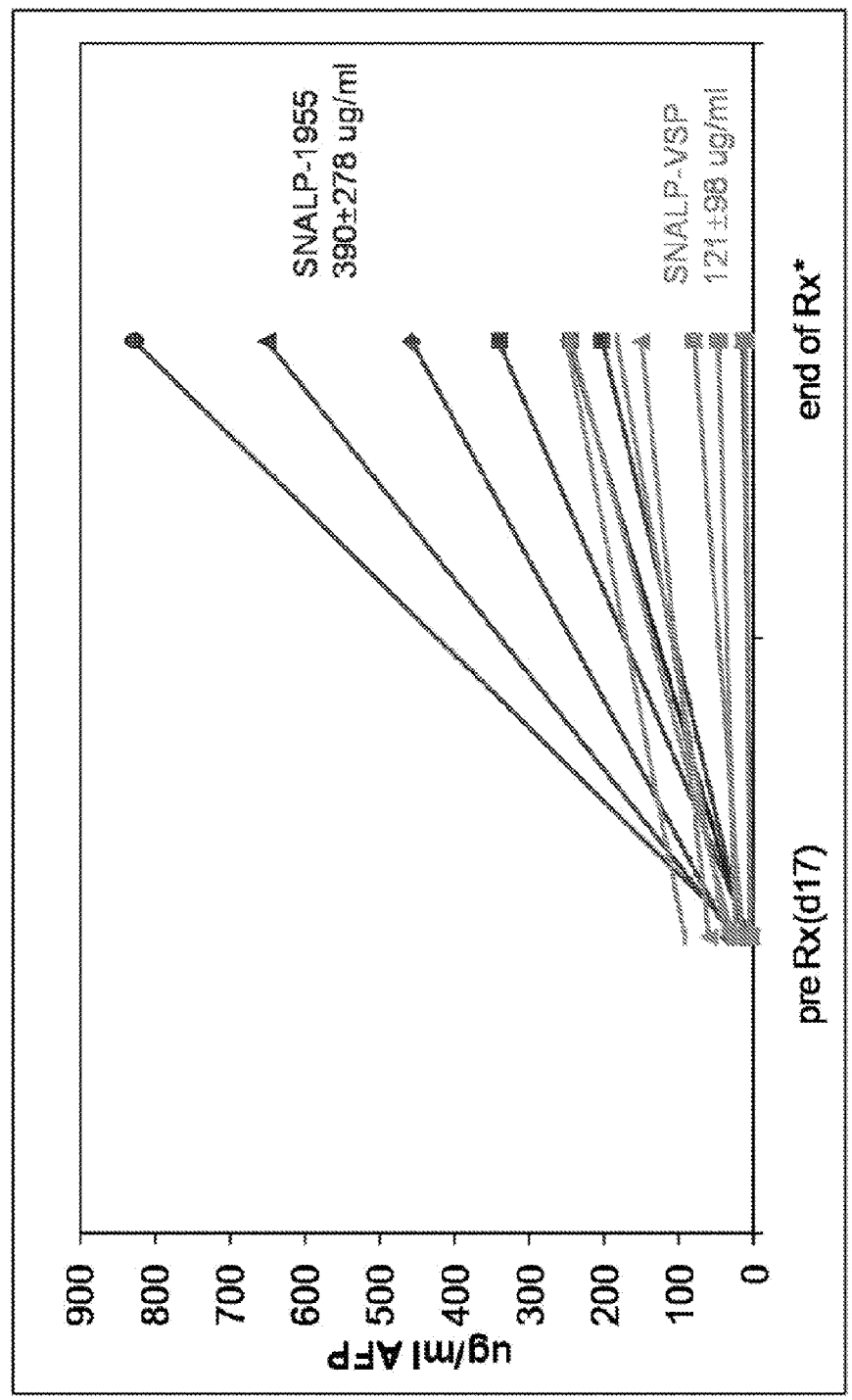
FIG. 14 is a graph showing the effects of SNALP-siRNAs on serum alpha fetoprotein (AFP) levels.

Tumor burden was monitored using serum AFP levels during the course of the experiment. Alpha-fetoprotein (AFP) is a major plasma protein produced by the yolk sac and the liver during fetal life. The protein is thought to be the fetal counterpart of serum albumin, and human AFP and albumin gene are present in tandem in the same transcriptional orientation on chromosome 4. AFP is found in monomeric as well as dimeric and trimeric forms, and binds copper, nickel, fatty acids and bilirubin. AFP levels decrease gradually after birth, reaching adult levels by 8-12 months. Normal adult AFP levels are low, but detectable. AFP has no known function in normal adults and AFP expression in adults is often associated with a subset of tumors such as hepatoma and teratoma. AFP is a tumor marker used to monitor testicular cancer, ovarian cancer, and malignant teratoma. Principle tumors that secrete AFP include endodermal sinus tumor (yolk sac carcinoma), neuroblastoma, hepatoblastoma, and heptocellular carcinoma. In patients with AFP-secreting tumors, serum levels of AFP often correlate with tumor size. Serum levels are useful in assessing response to treatment. Typically, if levels of AFP go down after treatment, the tumor is not growing. A temporary increase in AFP immediately following chemotherapy may indicate not that the tumor is growing but rather that it is shrinking (and releasing AFP as the tumor cells die). Resection is usually associated with a fall in serum levels. As shown in FIG. 14, tumor burden in SNALP-VSP treated animals was significantly reduced.

Example 7b

ALN-VSP Extends Survival

As used herein, ALN-VSP refers to lipid formulated siRNAs targeting VEGF and KSP (Eg5). The siRNAs are ALN-12115 targeting KSP and ALN-3133 targeting VEGF. The lipid formulation is a SNALP formulation (described herein) and including DLinDMA, DSPC, mPEG2000-C-DMA, and cholesterol.

Figure 13B:
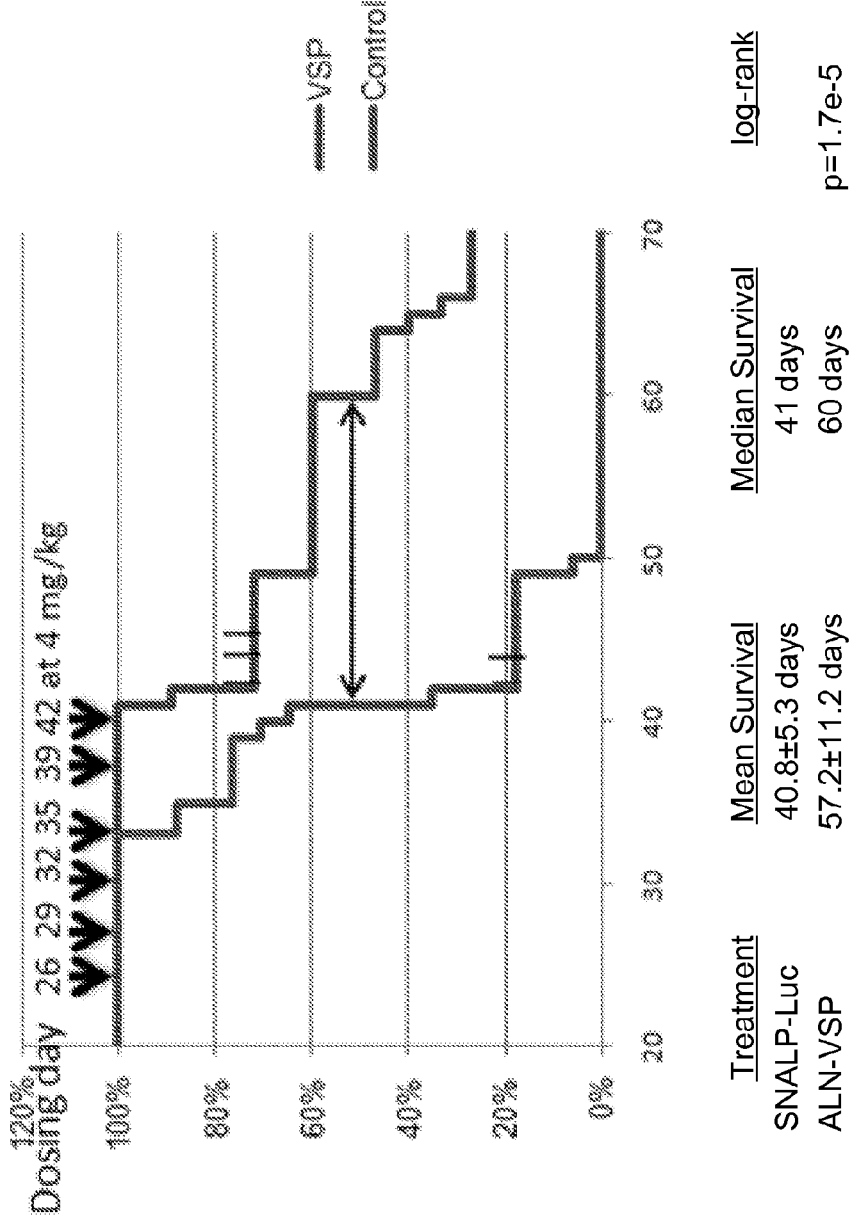

Tumors were established by intrahepatic implantation of Hep3B cells as described herein. 4 mg/kg of ALN-VSP or SNALP-Luc was administered twice per week for three weeks beginning 26 days after tumor implantation. Animals were euthanized based on humane surrogate endpoints. As shown in FIG. 13B, mean survival of ALN-VSP animals was extended by approximately 50% versus SNALP-Luc treated animals.

Example 8a

Induction of Mono-Asters in Orthotopic HCC Model

Inhibition of KSP in dividing cells leads to the formation of mono asters that are readily observable in histological sections. Orthotopic mouse liver tumor models were used as described herein. Briefly, human hepatoma cells (Hep3B) or human colorectal carcinoma cells (HCT116) were injected intrahepatically into the left lateral lobe of scid/beige mice.

Figure 15:
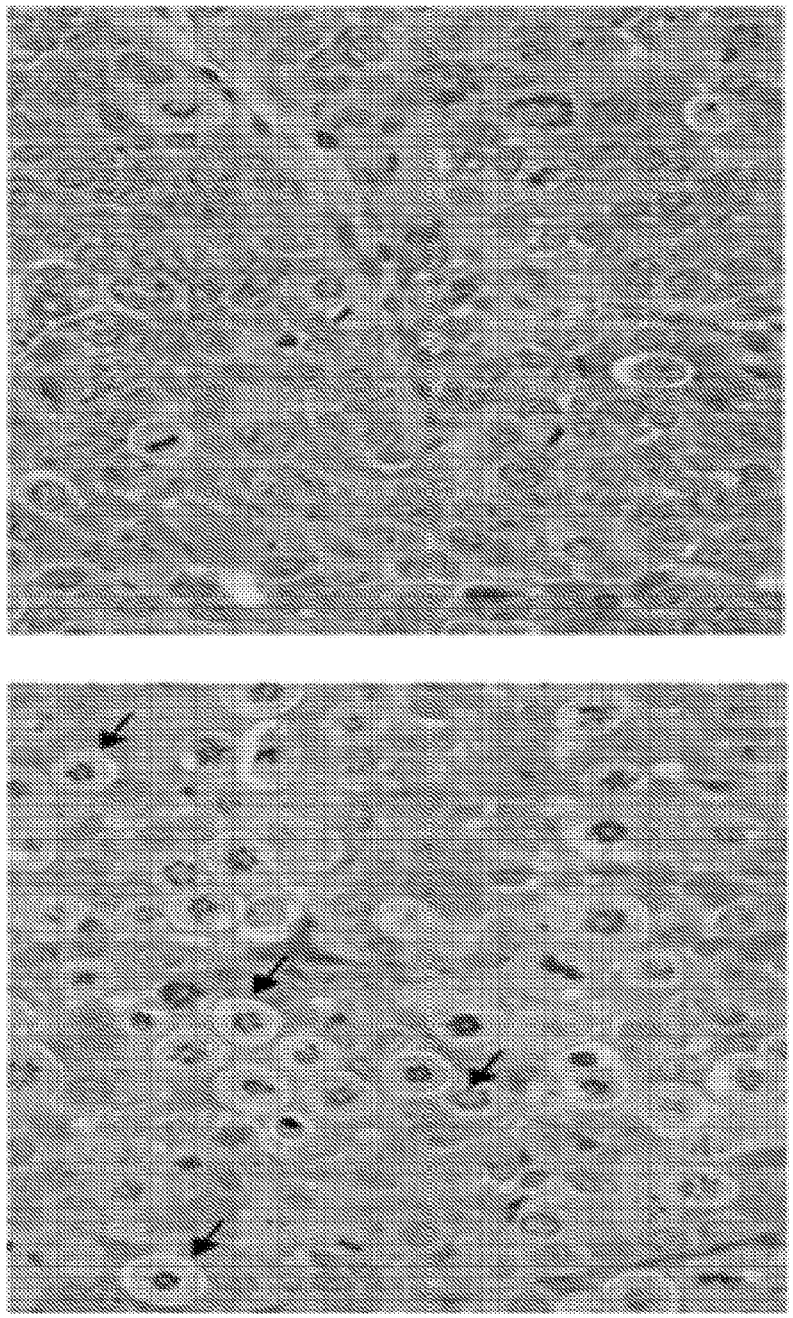
FIG. 15A and FIG. 15B are images of H&E stained sections in tumor bearing animals (three weeks after Hep3B cell implantation) were administered 2 mg/kg SNALP-VSP (A) or 2 mg/kg SNALP-Luc (B). Twenty four hours later, tumor bearing liver lobes were processed for histological analysis. Arrows indicate mono asters.

To determine whether mono aster formation occurred in SNALP-VSP treated tumors, tumor bearing animals (three weeks after Hep3B cell implantation) were administered 2 mg/kg SNALP-VSP via tail vein injection. Control animals received 2 mg/kg SNALP-Luc. Twenty four hours later, animals were sacrificed, and tumor bearing liver lobes were processed for histological analysis. Representative images of H&E stained tissue sections are shown in FIG. 15. Extensive mono aster formation was evident in ALN VSP02 treated (FIG. 15A, but not SNALP-Luc treated FIG. 15B, tumors. In the latter, normal mitotic figures were evident. The generation of mono asters is a characteristic feature of KSP inhibition and provides further evidence that SNALP-VSP has significant activity in established liver tumors.

Example 8b

Induction of Monoasters in Intraperitoneal HCC Model

A mouse HEP3B metastatic model was developed and used to assay the effect of ALN-VSP treatment on monoaster formation in intraperitoneal HEP3B tumors. HEP3B cells were obtained from ATCC and engineered to stably express Firefly Luciferase. Fox scid beige mice (8-9 weeks old) were obtained from Charles River Laboratories. 1 ml cells suspended in 100 cc of sterile PBS were injected in to the peritoneal cavity. Tumor growth was monitored using non invasive luminescence imaging.

Figure 20:
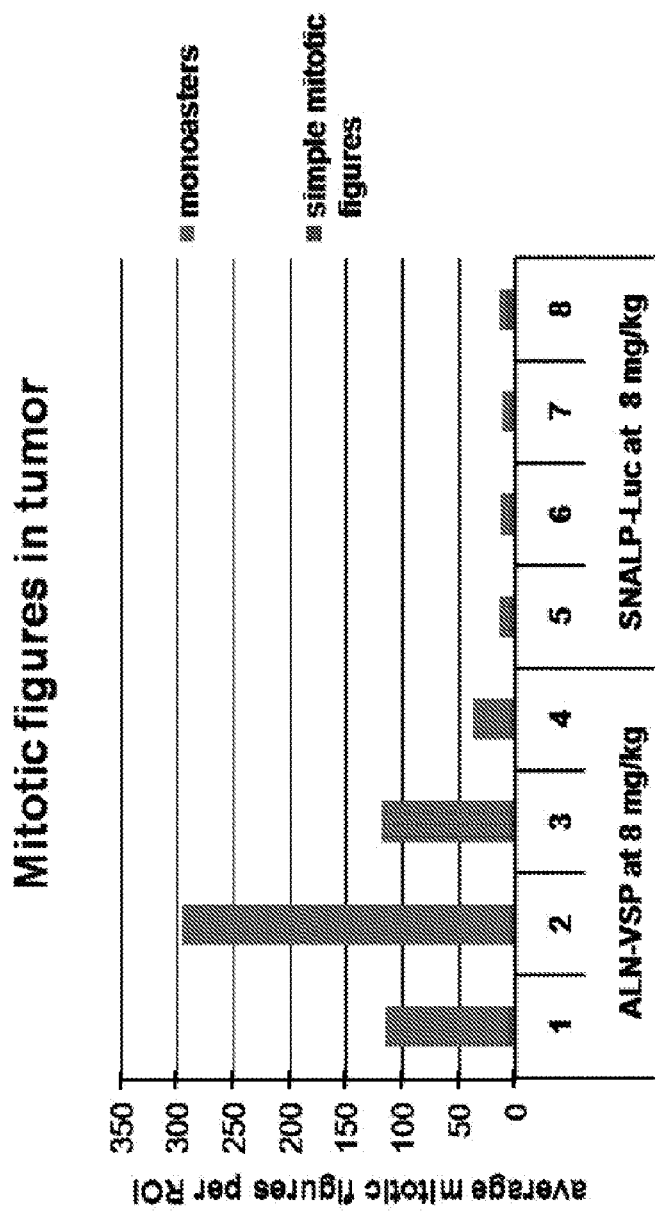
FIG. 20 is a graph illustrating the effect of ALN-VSP treatment of an intraperitoneal HCC mouse model on mitotic figure (monoaster) formation in tumors.

Animals received a single dose of ALN-VSP or SNALP-Luc at 8 mg/kg. Tumors were analyzed 48 h after dosing. Paraffin embedded sections of tumors were stained with H&E. Whole tumor sections were imaged using floating ROI (region of interest) analysis, and the number of simple mitoses or aberrant mitotic figures (monoasters) were counted. Total counts were divided by the number of ROI per tumor. As show in FIG. 20 ALN-VSP treatment leads to the accumulation of aberrant mitotic figures (monoasters) in tumor tissue from intraperitoneal HCC model.

Example 8c

Reduction of mRNA Levels and Induction of Monoasters in Colorectal Carcinoma Tumors in Liver and Extrahepatic Sites The efficacy of treatment with ALN-VSP in colorectal carcinoma tumors was assayed. Tumors were established by intrahepatic implantation of HCT116 cells directly into the livers of immunocompromised mice (i.e., into the left lateral lobe of scid/beige mice). In some animals, disseminated tumors developed at extra-hepatic sites, including lymph nodes, lungs, and subcutaneously (s.c.). Tumor bearing animals received either a single dose or multiple doses.

Figure 21:
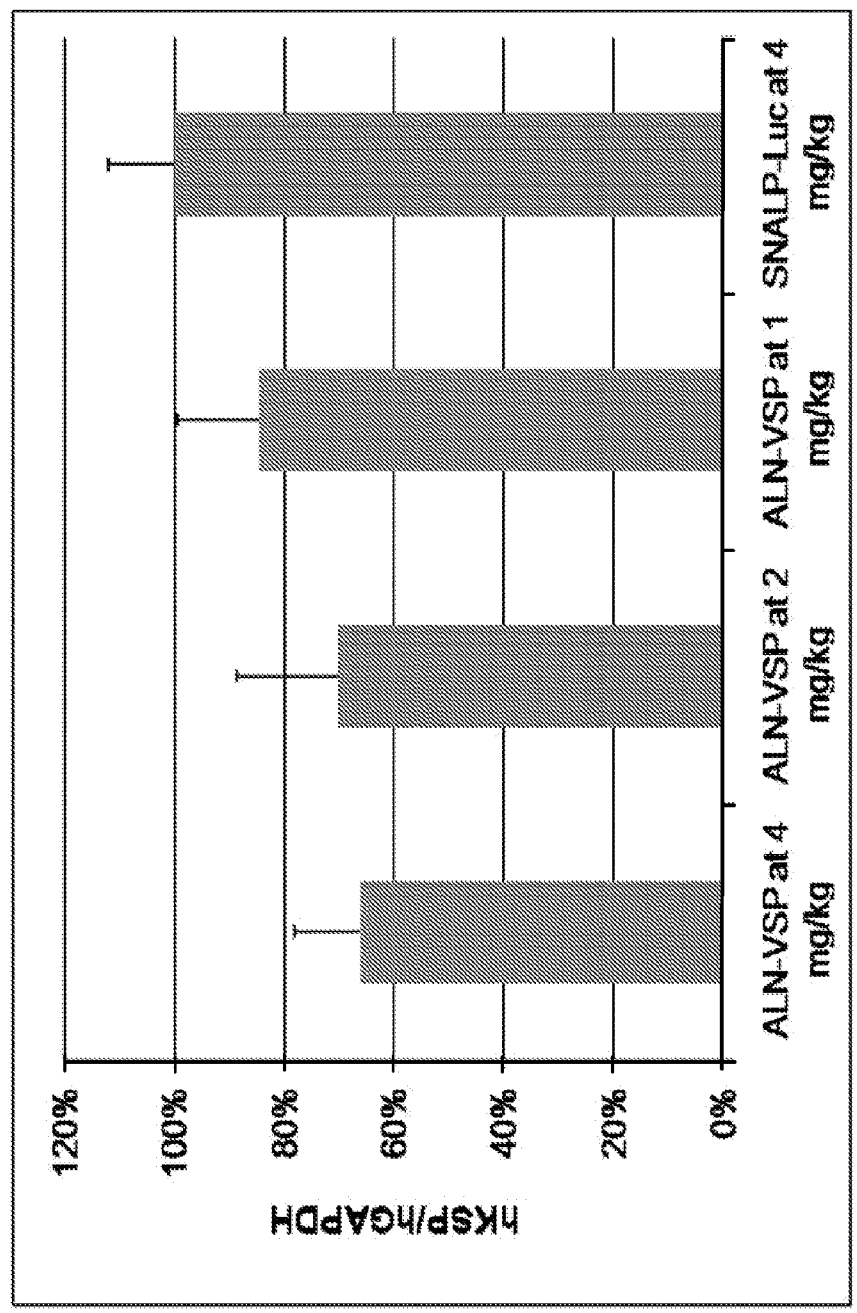
FIG. 21 is a graph illustrating the effect of ALN-VSP treatment of mice implanted intrahepatically with HCT116 (colorectal carcinoma cells) on hKSP mRNA levels in tumors.

Tumor bearing animals received a single dose of ALN-VSP (4, 2 or 1 mg/kg) or SNALP-Luc (4 mg/kg) 14 days after tumor implantation. mRNA levels of tumor-derived (human) KSP, normalized to GAPDH, were measured 24 h after drug administration using species specific TaqMan probes. As shown in FIG. 21, ALN-VSP demonstrated 35% reduction of hKSP relative to the SNALP-Luc control at 4 mg/kg.

Tumor bearing animals received multiple doses of ALN-VSP and SNALP-Luc 14 days after tumor implantation. ALN-VSP was administered at 4.0 and 1.0 mg/kg, control SNALP-Luc at 4 mg/kg twice a week for 3 weeks. Tumor bearing livers, lymph nodes, lungs and subcutaneous metastases were analyzed 48 h after dosing. Paraffin embedded sections of tumors were stained with H&E. Whole tumor sections were imaged using floating ROI (region of interest) analysis, and the number of simple mitoses or aberrant mitotic figures (monoasters) were counted. Total counts were divided by the number of ROI per tumor.

Figure 22A:
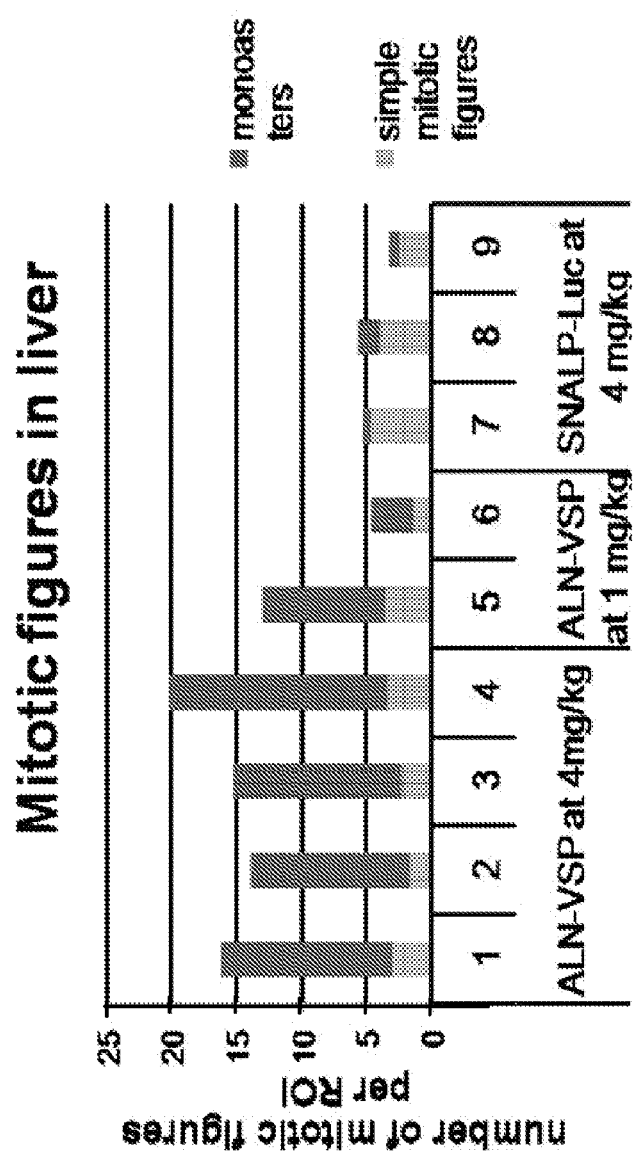
FIG. 22 are graphs illustrating the effect of ALN-VSP treatment of mice implanted intrahepatically with HCT 116 (colorectal carcinoma cells) on formation of mitotic figures (e.g., monasters) in liver (FIG. 22A) and lymph nodes (FIG. 22B).
Figure 22B:
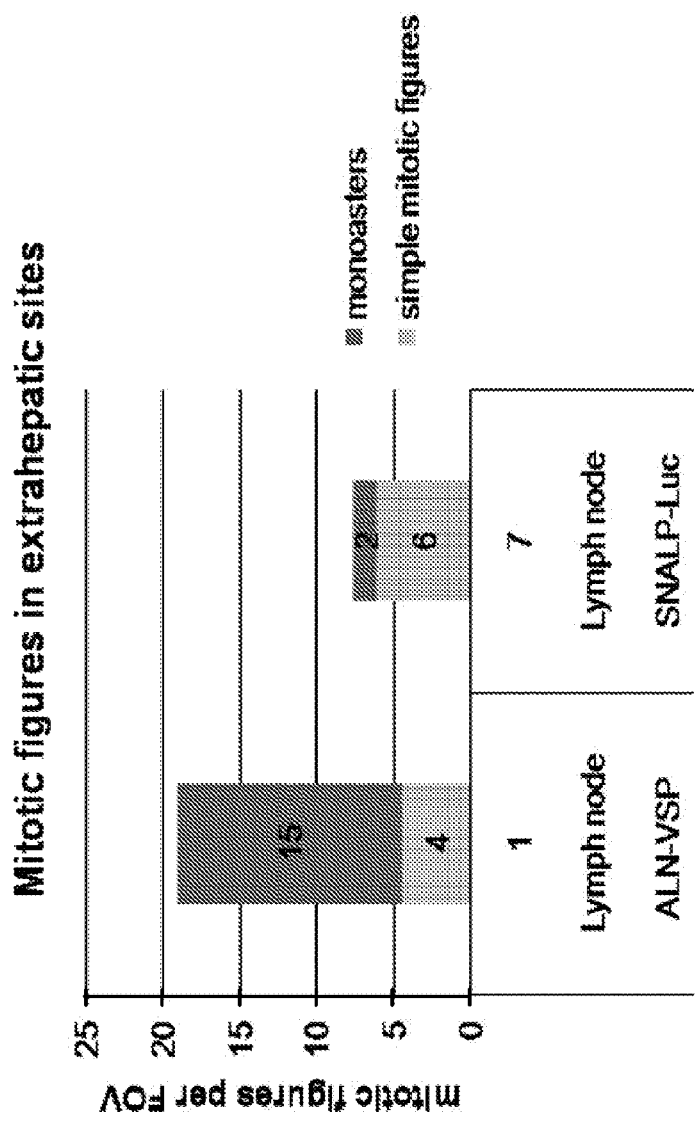
Figure 25A:
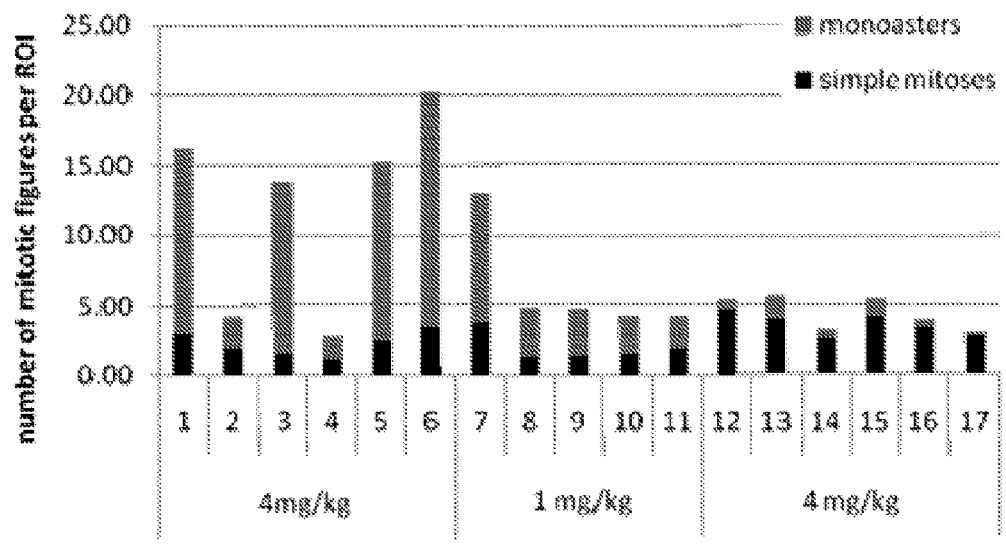
FIG. 25 are graphs illustrating the effect of ALN-VSP treatment monoaster formation mouse models of intrahepatic colorectal carcinoma tumors. Results are shown for liver (FIG. 25A), lung (FIG. 25B), lymph nodes and subcutaneous metasteses (FIG. 25C).
Figure 25A:
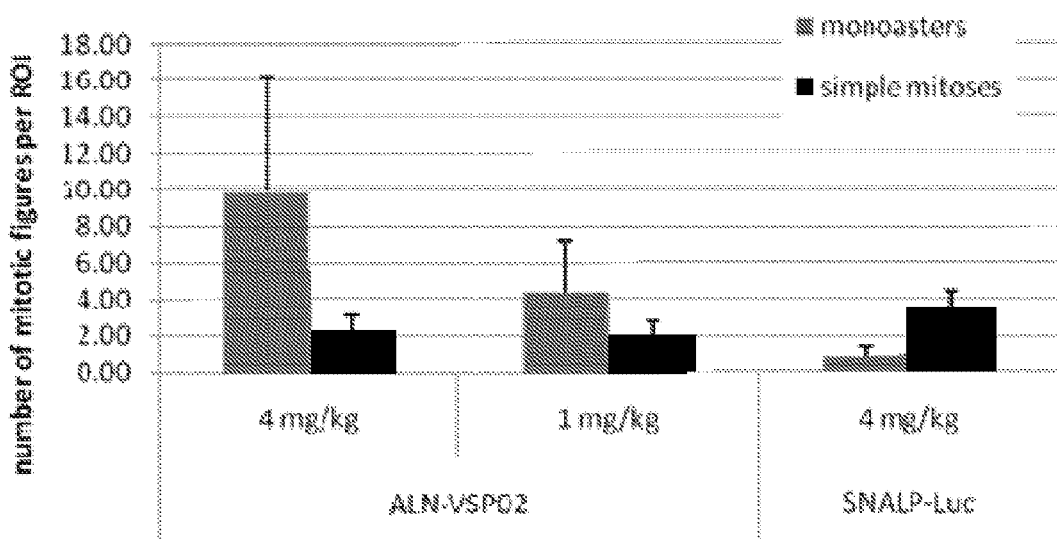
Figure 25B:
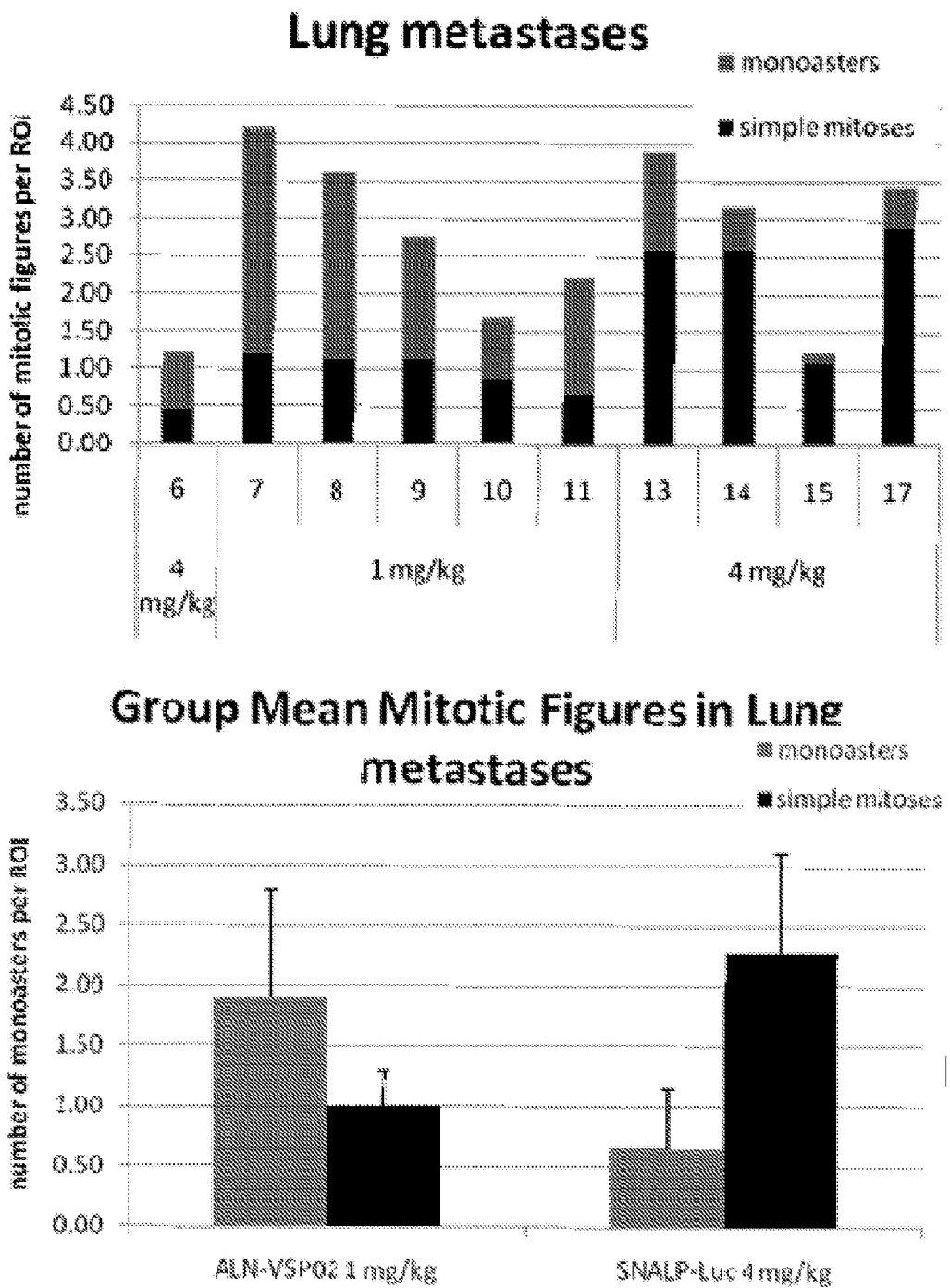
Figure 25C:
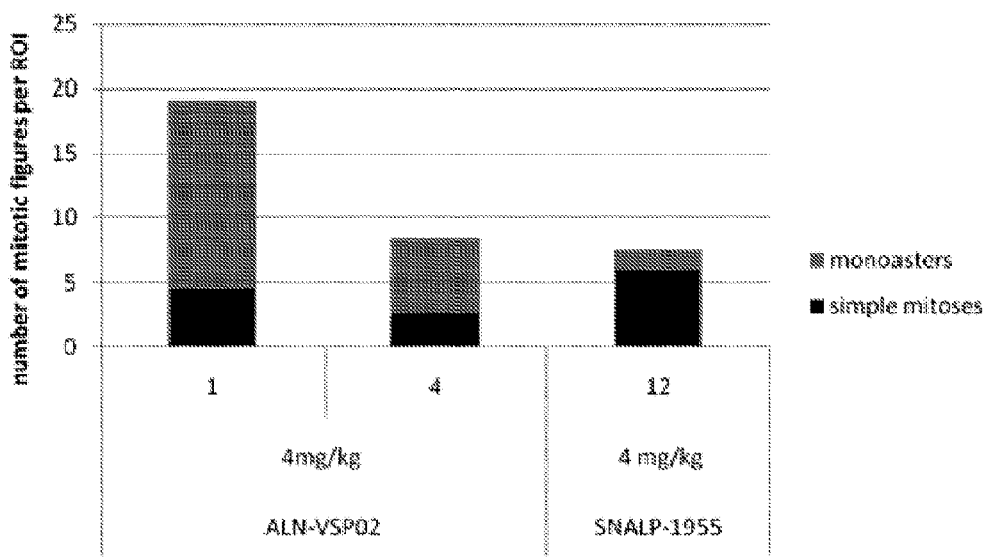
Figure 25C:
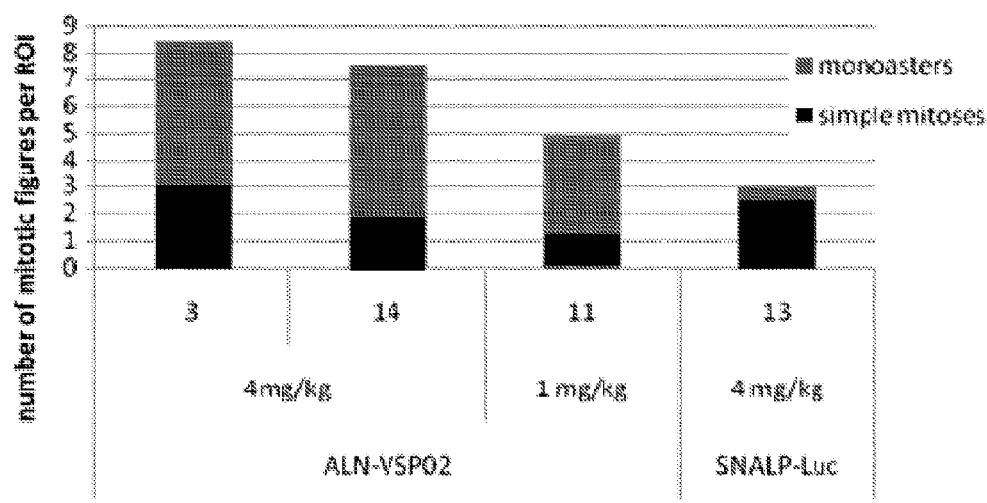

As shown in FIG. 25A, FIG. 25B, and FIG. 25C, ALN-VSP treatment leads to accumulation of aberrant mitotic figures (monoasters) in liver tumors, lung, lymph node, and subcutaneous metastases. FIGS. 22A & 25A (liver), $P<0.05$ (One-way ANOVA with Tukey's multiple comparison test); FIG. 25B (lung) $p=0.0182$ by unpaired t test as compared to monoasters in SNALP-1955 treated animals; FIGS. 22B & 25C (lymph node); FIG. 25C (subcutaneous).

The results demonstrated that each siRNA makes a distinct contribution to efficacy. ALN-VSP treatment led to accumulation of aberrant mitotic figures (monoasters), a hallmark of KSP inhibition, in both types of orthotopic liver tumors, as well as in extra-hepatic tumors of different origin. Evidence of therapeutic VEGF inhibition was shown by marked reductions in tumor microvessel density and intratumoral hemorrhage in orthotopic tumors.

Example 8d

ALN-VSP Reduced Intratumoral Hemorrhage and Microvessel Density

The effect of treatment with ALN-VSP compared to SNALP-Luc on intratumoral hemorrhage and microvessel density was analyzed in using the Hep3B orthotopic HCC mouse model described herein.

Two studies were performed. Study 1 compared 4 mg/kg ALN-VSP vs. SNALP-Luc administered twice per week for three weeks beginning 26 days after Hep3B orthotopic tumor implantation. Animals were euthanized based on humane surrogate end points. Study 2 compared 6 mg/kg SNALP-VEGF only vs. SNALP-Luc administered twice per week for three weeks beginning 14 days after tumor implantation. Bevacizumab at 5 mg/kg administered IP was used as a positive control. Animals were euthanized 72 h after the last dose.

Paraffin embedded sections of tumors were stained with H&E to reveal regions of tumor hemorrhage, or with a CD34 antibody to detect tumor vasculature. Two whole tumor sections from distant tumor slabs were imaged using floating ROI (region of interest) analysis. Regions of intratumoral hemorrhage were outlined in H&E stained sections and total areas of hemorrhage were quantified in each tumor. To quantify microvessel density, CD34 stained areas were quantified as a percentage of total tumor area.

Figure 23A:
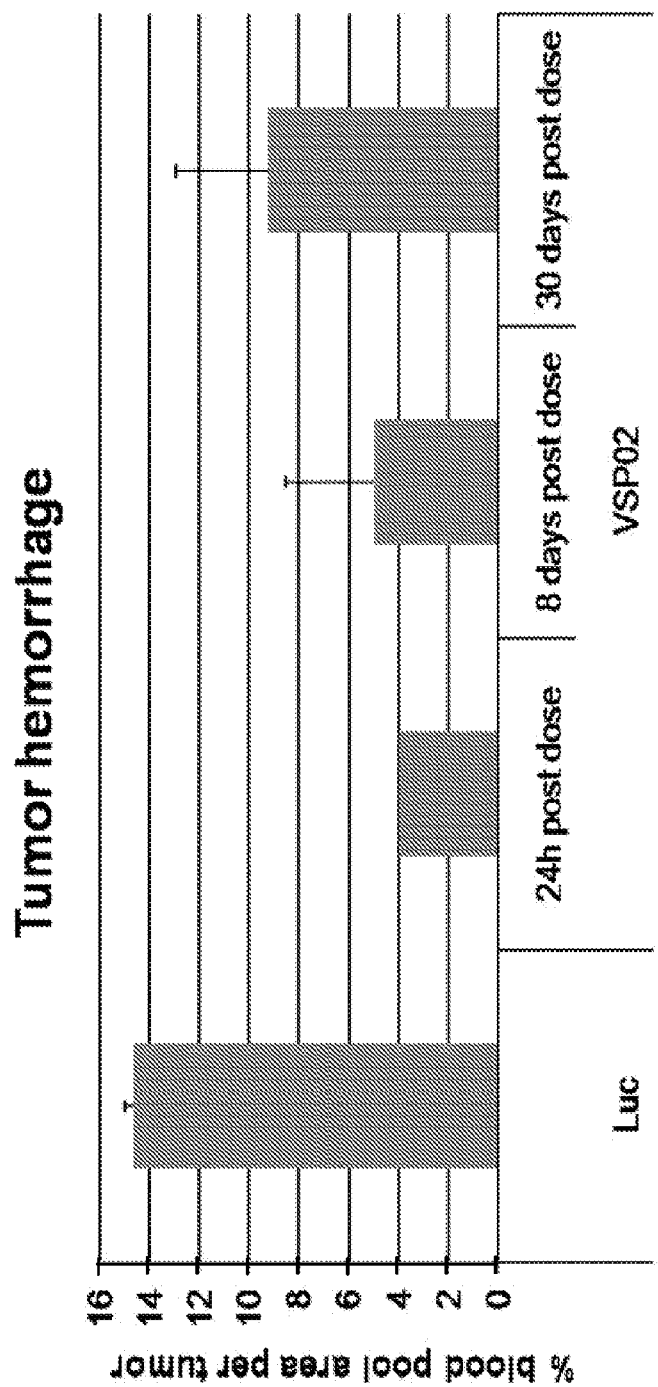
FIG. 23 are graphs illustrating the effect of ALN-VSP treatment of mice bearing orthotopic Hep3B tumors on tumor hemorrhage (FIG. 23A) and tumor microvessel density (FIG. 23B).
Figure 23B:
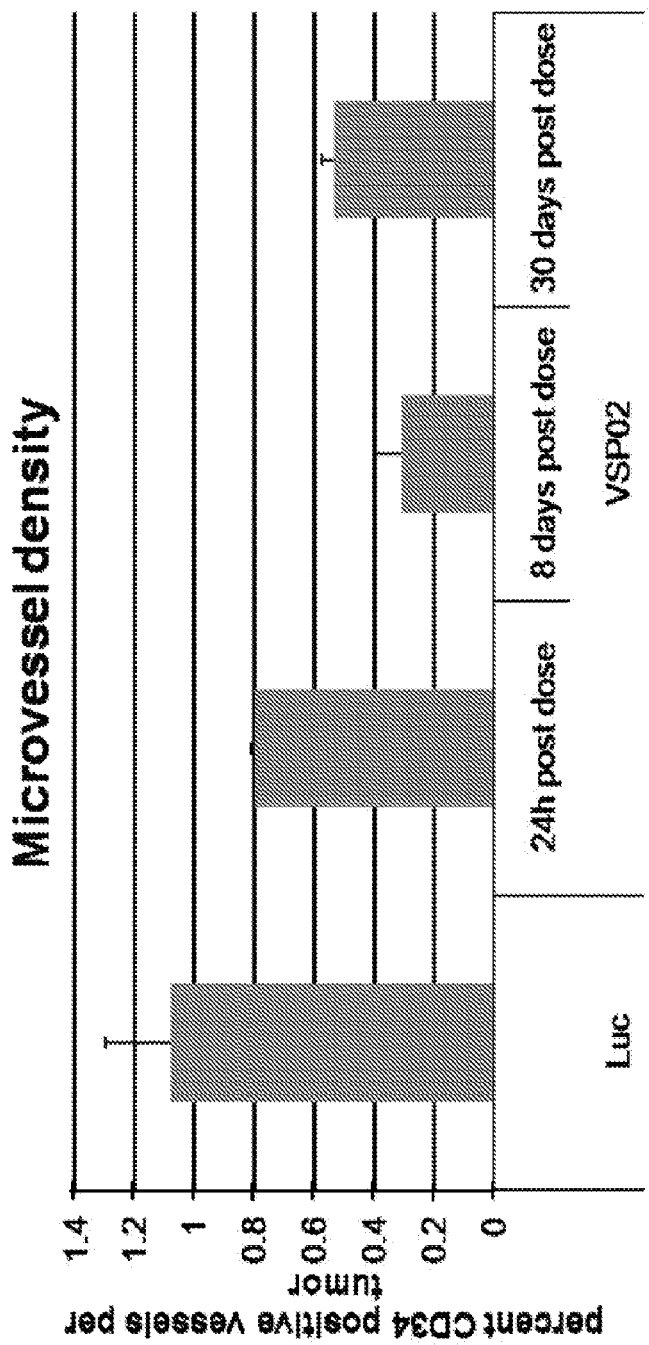
Figure 24:
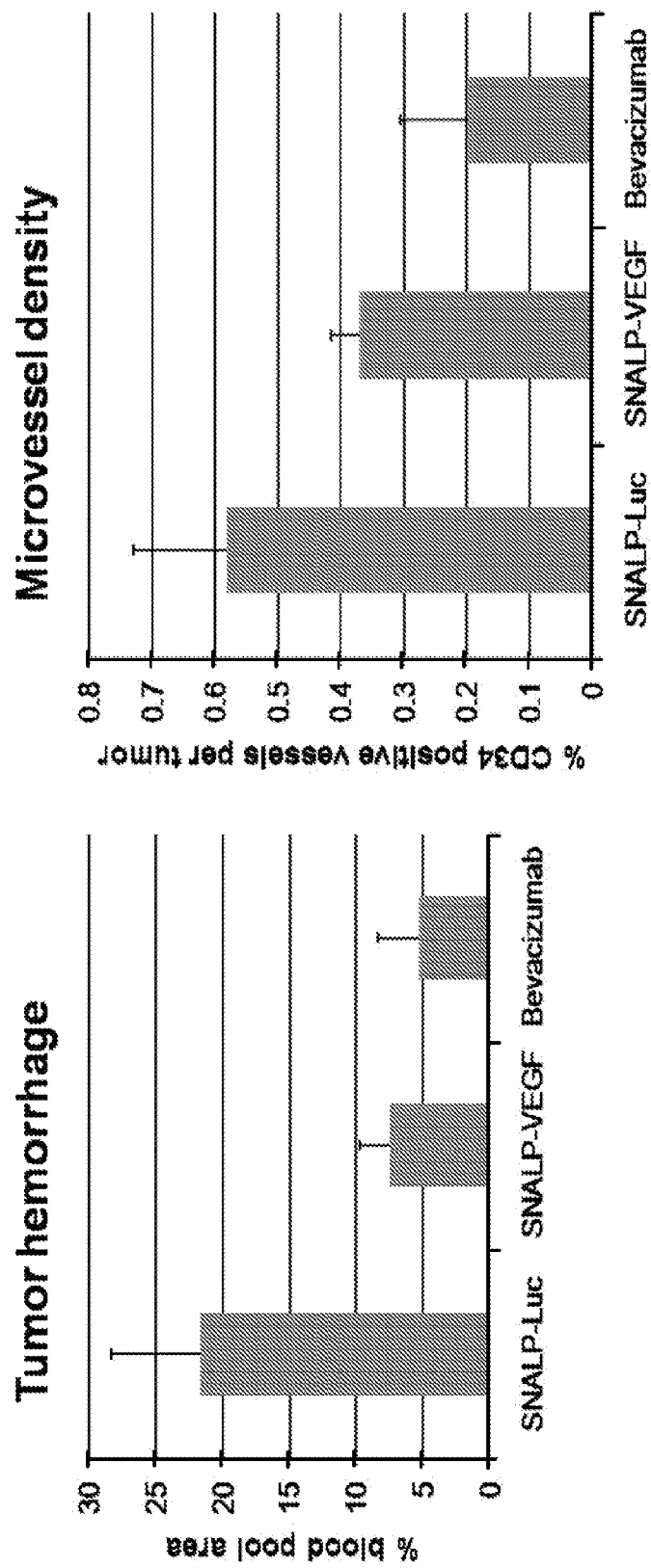
FIG. 24 are graphs illustrating the effect of SNALP-VEGF only treatment of mice bearing orthotopic Hep3B tumors on tumor hemorrhage (FIG. 24A) and tumor microvessel density (FIG. 24B).

As shown in FIG. 23, ALN-VSP treatment reduced tumor hemorrhage and microvessel density. As shown in FIG. 24, the vascular effects of ALN-VSP were attributable to the VEGF siRNA as SNALP-VEGF reduces tumor hemorrhage and microvessel density to the same extent as ALN-VSP.

Example 9

Manufacturing Process and Product Specification of ALN-VSP02 (SNALP-VSP)

ALN-VSP02 product contains 2 mg/mL of drug substance ALN-VSPDS01 formulated in a sterile lipid particle formulation (referred to as SNALP) for IV administration via infusion. Drug substance ALN-VSPDS01 consists of two siRNAs (ALN-12115 targeting KSP and ALN-3133 targeting VEGF) in an equimolar ratio. The drug product is packaged in 10 mL glass vials with a fill volume of 5 mL.

The following terminology is used herein:

| Drug Substance | siRNA Duplexes | Single Strand Intermediates |
|---|---|---|
| ALN-VSPDS01 | ALN-12115* | Sense: A-19562 |
| | | Antisense: A-19563 |
| | ALN-3133** | Sense: A-3981 |
| | | Antisense: A-3982 |

*Alternate names = AD-12115, AD12115;
**Alternate names = AD-3133, AD3133

9.1 Preparation of Drug Substance ALN-VSPDS01

The two siRNA components of drug substance ALN-VSPDS01, ALN-12115 and ALN-3133, are chemically synthesized using commercially available synthesizers and raw materials. The manufacturing process consists of synthesizing the two single strand oligonucleotides of each duplex (A 19562 sense and A 19563 antisense of ALN 12115 and A 3981 sense and A 3982 antisense of ALN 3133) by conventional solid phase oligonucleotide synthesis using phosphoramidite chemistry and 5' O dimethoxytriphenylmethyl (DMT) protecting group with the 2' hydroxyl protected with tert butyldimethylsilyl (TBDMS) or the 2' hydroxyl replaced with a 2' methoxy group (2' OMe). Assembly of an oligonucleotide chain by the phosphoramidite method on a solid support such as controlled pore glass or polystyrene. The cycle consists of 5' deprotection, coupling, oxidation, and capping. Each coupling reaction is carried out by activation of the appropriately protected ribo, 2' OMe, or deoxyribonucleoside amidite using 5 (ethylthio) 1H tetrazole reagent followed by the coupling of the free 5' hydroxyl group of a support immobilized protected nucleoside or oligonucleotide. After the appropriate number of cycles, the final 5' protecting group is removed by acid treatment. The crude oligonucleotide is cleaved from the solid support by aqueous methylamine treatment with concomitant removal of the cyanoethyl protecting group as well as nucleobase protecting groups. The 2' O TBDMS group is then cleaved using a hydrogen fluoride containing reagent to yield the crude oligoribonucleotide, which is purified using strong anion exchange high performance liquid chromatography (HPLC) followed by desalting using ultrafiltration. The purified single strands are analyzed to confirm the correct molecular weight, the molecular sequence, impurity profile and oligonucleotide content, prior to annealing into the duplexes. The annealed duplex intermediates ALN 12115 and ALN 3133 are either lyophilized and stored at 20° C. or mixed in 1:1 molar ratio and the solution is lyophilized to yield drug substance ALN VSPDS01. If the duplex intermediates were stored as dry powder, they are redissolved in water before mixing. The equimolar ratio is achieved by monitoring the mixing process by an HPLC method.

Figure 16:
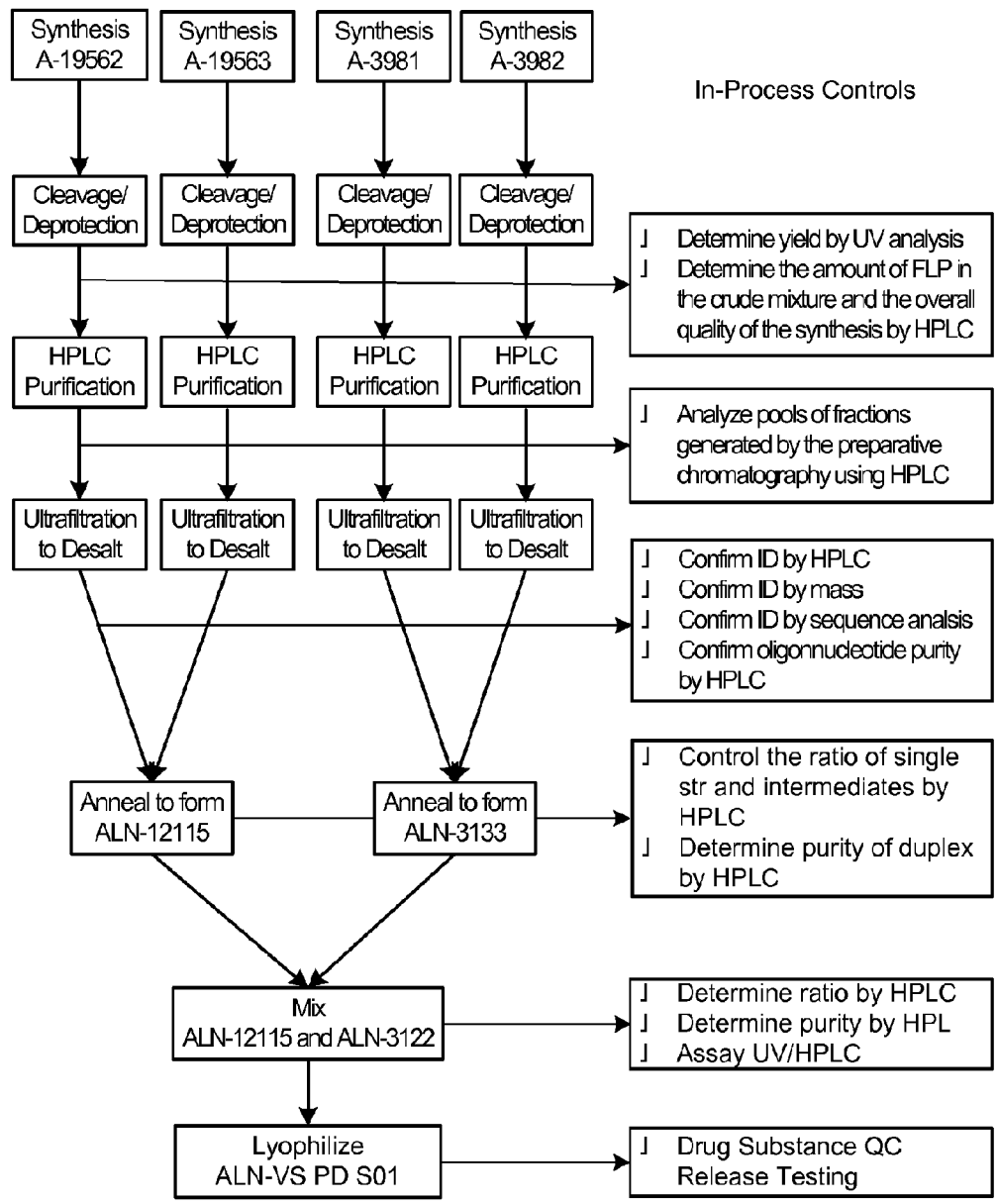
FIG. 16 is a flow diagram illustrating the manufacturing process of ALN-VSPDS01.

The manufacturing process flow diagram is shown in FIG. 16.

The drug substance was assayed for storage stability (data not shown) The assay methods were chosen to assess physical property (appearance, pH, moisture), purity (by SEC and denaturing anion exchange chromatography) and potency (by denaturing anion exchange chromatography [AX-HPLC]). ALN-VSPDS01 showed stability for up to 12 months storage at 20 degrees C.

9.2 Preparation of Drug Product ALN-VSP02 (SNALP-VSP)

Figure 17:
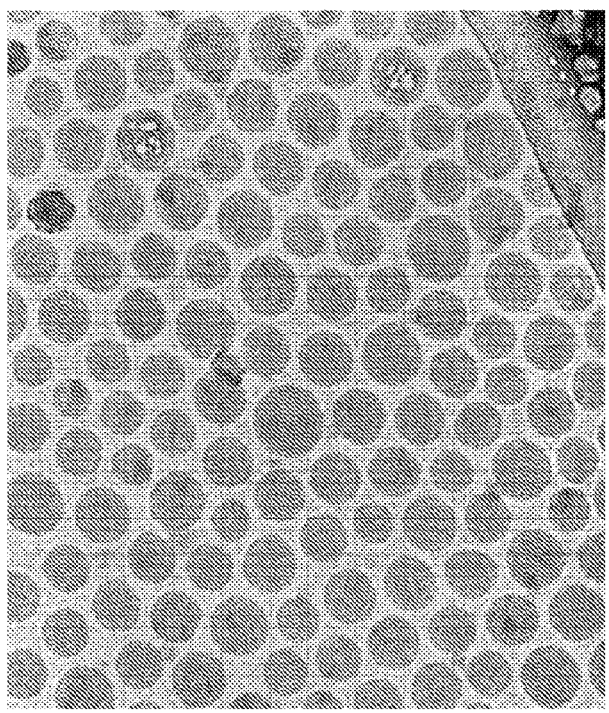
FIG. 17 is a cryo-transmission electron microscope (cryo-TEM) image of ALN-VSP02.

ALN VSP02, is a sterile formulation of the two siRNAs (in a 1:1 molar ratio) with lipid excipients in isotonic buffer. The lipid excipients associate with the two siRNAs, protect them from degradation in the circulatory system, and aid in their delivery to the target tissue. The specific lipid excipients and the quantitative proportion of each (shown in Table 9) have been selected through an iterative series of experiments comparing the physicochemical properties, stability, pharmacodynamics, pharmacokinetics, toxicity and product manufacturability of numerous different formulations. The excipient DLinDMA is a titratable aminolipid that is positively charged at low pH, such as that found in the endosome of mammalian cells, but relatively uncharged at the more neutral pH of whole blood. This feature facilitates the efficient encapsulation of the negatively charged siRNAs at low pH, preventing formation of empty particles, yet allows for adjustment (reduction) of the particle charge by replacing the formulation buffer with a more neutral storage buffer prior to use. Cholesterol and the neutral lipid DPPC are incorporated in order to provide physicochemical stability to the particles. The polyethyleneglycol lipid conjugate PEG2000 C DMA aids drug product stability, and provides optimum circulation time for the proposed use. ALN VSP02 lipid particles have a mean diameter of approximately 80-90 nm with low polydispersity values. A representative cryo transmission electron microscope (cryo TEM) image is shown in FIG. 17. At neutral pH, the particles are essentially uncharged, with Zeta Potential values of less than 6 mV. There is no evidence of empty (non loaded) particles based on the manufacturing process.

TABLE 9

Quantitative Composition of ALN-VSP02

| Component, grade | Proportion (mg/mL) |
|---|---|
| ALN-VSPDS01, cGMP | 2.0* |
| DLinDMA (1,2-Dilinoleyloxy-N,N-dimethyl-3-aminopropane), cGMP | 7.3 |
| DPPC (R-1,2-Dipalmitoyl-sn-glycero-3-phosphocholine), cGMP | 1.1 |
| Cholesterol, Synthetic, cGMP | 2.8 |
| PEG2000-C-DMA (3-N-[(ω-Methoxy poly(ethylene glycol) 2000) carbamoyl]-1,2-dimyristyloxy-propylamine), cGMP | 0.8 |
| Phosphate Buffered Saline, cGMP | q.s. |

*The 1:1 molar ratio of the two siRNAs in the drug product is maintained throughout the size distribution of the drug product particles.

Figure 18:
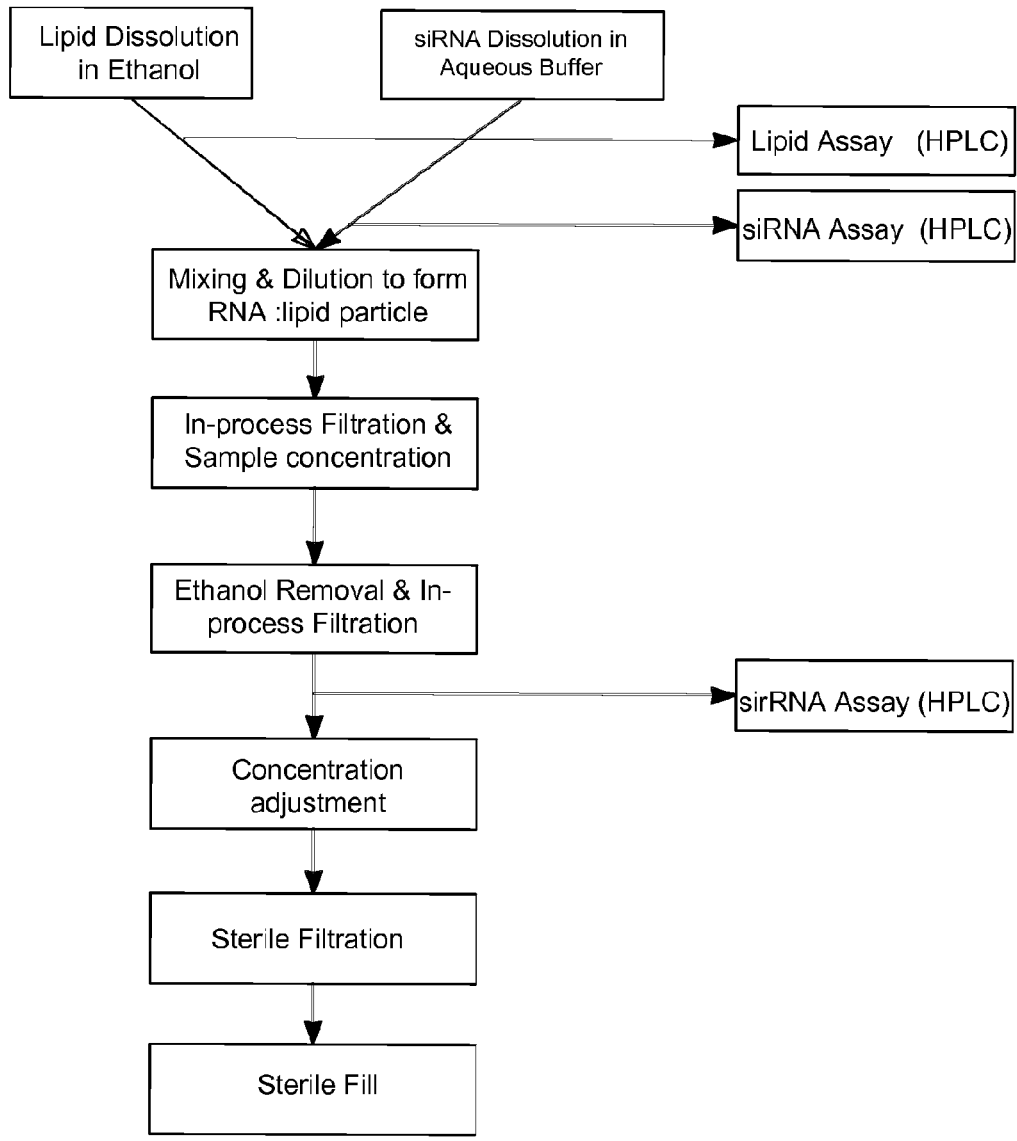
FIG. 18 is a flow diagram illustrating the manufacturing process of ALN-VSP02.
Figure 19:
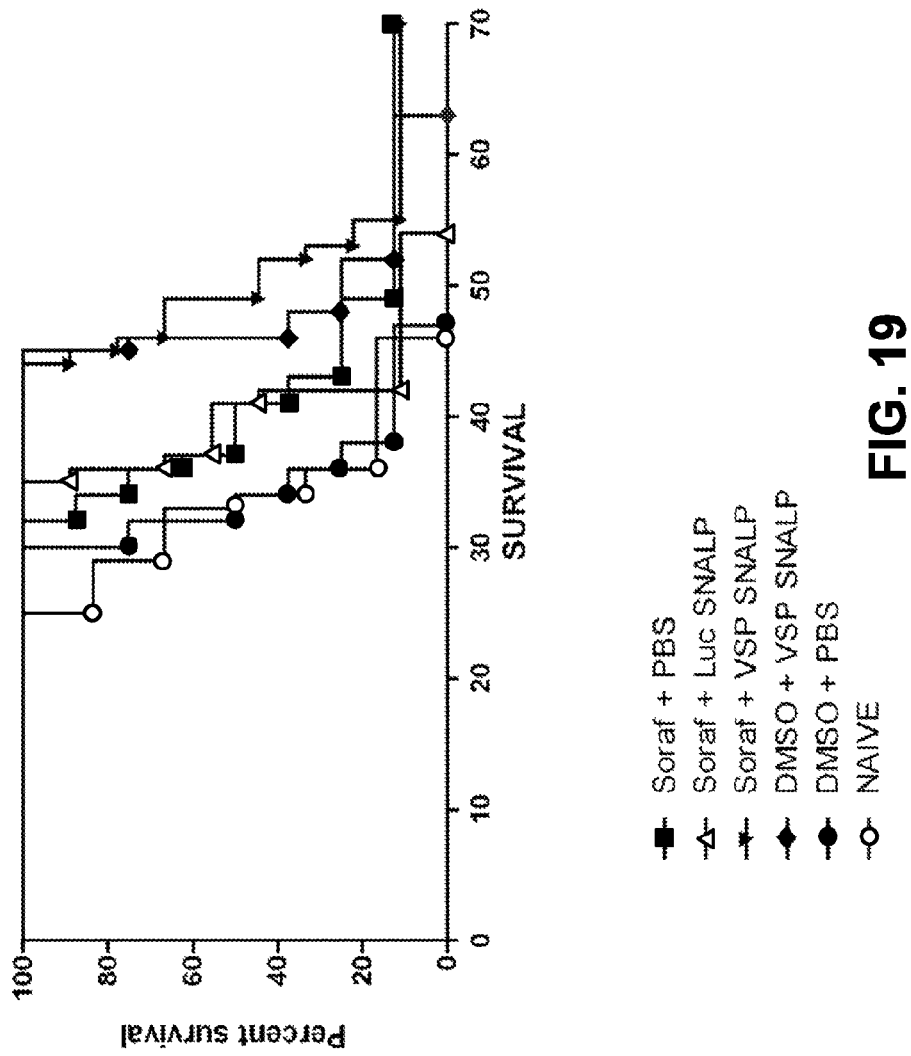
FIG. 19 is a graph illustrating the effects on survival of administration SNALP formulated siRNA and Sorafenib.

Solutions of lipid (in ethanol) and ALN VSPDS01 drug substance (in aqueous buffer) are mixed and diluted to form a colloidal dispersion of siRNA lipid particles with an average particle size of approximately 80-90 nm. This dispersion is then filtered through 0.45/0.2 μm filters, concentrated, and diafiltered by Tangential Flow Filtration. After in process testing and concentration adjustment to 2.0 mg/mL, the product is sterile filtered, aseptically filled into glass vials, stoppered, capped and placed at 5±3° C. The ethanol and all aqueous buffer components are USP grade; all water used is USP Sterile Water For Injection grade. Representative ALN-VSP02 process is shown in flow diagram in FIG. 18.

9.4 Container/Closure System

The ALN VSP02 drug product is packaged in 10 mL glass vials with a fill volume of 5 mL. The container closure system is comprised of a USP/EP Type I borosilicate glass vial, a teflon faced butyl rubber stopper and an aluminum flip off cap. The drug product will be stored at 5±3° C.

9.5 Stability of Drug Product ALN-VSP02

The stability of the drug product was assayed at both storage conditions (2-8° C.) and at 25° C./60% RH. The drug product was stable at storage temperature of 4° C. at 18 months (data not shown).

Example 10

In Vitro Efficacy of ALN-VSP02 in Human Cancer Cell Lines

The efficacy of ALN-VSP02 treatment in human cancer cell lines was determined via measurement of KSP mRNA, VEGF mRNA, and cell viability after treatment. IC50 (nM) values determined for KSP and VEGF in each cell line.

TABLE 11

| cell lines | |
|---|---|
| Cell line tested | ATCC cat number |
| HELA | ATCC Cat N: CCL-2 |
| KB | ATCC Cat N: CCL-17 |
| HEP3B | ATCC Cat N: HB-8064 |
| SKOV-3 | ATCC Cat N: HTB-77 |
| HCT-116 | ATCC Cat N: CCL-247 |
| HT-29 | ATCC Cat N: HTB-38 |
| PC-3 | ATCC Cat N: CRL-1435 |
| A549 | ATCC Cat N: CCL-185 |
| MDA-MB-231 | ATCC Cat N: HTB-26 |

Cells were plated in 96 well plates in complete media at day 1 to reach a density of 70% on day 2. On day 2 media was replaced with Opti-MEM reduced serum media (Invitrogen Cat N: 11058-021) and cells were transfected with either ALN-VSP02 or control SNALP-Luc with concentration range starting at 1.8 μM down to 10 pM. After 6 hours the media was changed to complete media. Three replicate plates for each cell line for each experiment was done.

Cells were harvested 24 hours after transfection. KSP levels were measured using bDNA; VEGF mRNA levels were measured using human TaqMan assay.

Viability was measured using Cell Titer Blue reagent (Promega Cat N: G8080) at 48 and/or 72 h following manufacturer's recommendations.

As shown in Table 12, nM concentrations of VSP02 are effective in reducing expression of both KSP and VEGF in multiple human cell lines. Viability of treated cells was not

TABLE 12

| | Results | |
|---|---|---|
| Cell line | IC50 (nM) KSP | IC50 (nM) VEGF |
| HeLa | 8.79 | 672 |
| SKOV-3 | 142 | 1347 |
| HCT116 | 31.6 | 27.5 |
| Hep3B | 1.3 | 14.5 |
| HT-29 | 262 | ND |
| PC3 | 127 | ND |
| KB | 50.6 | ND |
| A549 | 201 | ND |
| MB231 | 187 | ND |

Example 11

Anti-Tumor Efficacy of VSP SNALP vs. Sorafenib in Established Hep3B Intrahepatic Tumors The anti-tumor effects of multi-dosing VSP SNALP verses Sorafenib in scid/beige mice bearing established Hep3B intrahepatic tumors was studied. Sorafenib is a small molecule inhibitor of protein kinases approved for treatment of hepatic cellular carcinoma (HCC).

Tumors were established by intrahepatic seeding in scid/beige mice as described herein. Treatment was initiated 11 days post-seeding. Mice were treated with Sorafenib and a control siRNA-SNALP, Sorafenib and VSP siRNA-SNALP, or VSP siRNA-SNALP only. Control mice were treated with buffers only (DMSO for Sorafenib and PBS for siRNA-SNALP). Sorafenib was administered intraparenterally from Mon to Fri for three weeks, at 15 mg/kg according to body weight for a total of 15 injections. Sorafenib was administered a minimum of 1 hour after SNALP injections. The siRNA-SNALPS were administered intravenously via the lateral tail vein according at 3 mg/kg based on the most recently recorded body weight (10 ml/kg) for 3 weeks (total of 6 doses) on days 1, 4, 7, 10, 14, and 17.

Mice were euthanized based on an assessment of tumor burden including progressive weight loss and clinical signs including condition, abdominal distension/discoloration and mobility.

The percent survival data are shown in FIG. 21. Co-administration of VSP siRNA-SNALP with Sorafenib increased survival proportion compared to administration of Sorafenib or VSP siRNA-SNALP alone. VSP siRNA-SNALP increased survival proportion compared to Sorafenib.

Example 12

In Vitro Efficacy of VSP Using Variants of AD-12115 and AD-3133

Two sets of duplexes targeted to Eg5/KSP and VEGF were designed and synthesized. Each set included duplexes tiling 10 nucleotides in each direction of the target sites for either AD-12115 and AD-3133.

Sequences of the target, sense strand, and antisense strand for each duplex are shown in the Table below.

Each duplex is assayed for inhibition of expression using the assays described herein. The duplexes are administered alone and/or in combination, e.g., an Eg5/KSP dsRNA in combination with a VEGF dsRNA. In some embodiments, the dsRNA are administered in a SNALP formulation as described herein.

TABLE 13

Sequences of dsRNA targeted to VEGF and Eg5/KSP (tiling)

| Duplex ID | target gene | target sequence 5' to 3' | SEQ ID NO: | Sense Strand Antisense strand 5' to 3' | SEQ ID NO: |
|---|---|---|---|---|---|
| AD-20447.1 | VEGFA | ACCAAGGCCAGCACAUAGG | 14 | AccAAGGccAGcAcAuAGGTsT CCuAUGUGCUGGCCUUGGTsT | 54 55 |
| AD-20448.1 | VEGFA | CCAAGGCCAGCACAUAGGA | 15 | ccAAGGccAGcAcAuAGGATsT UCCuAUGUGCUGGCCUUGGTsT | 56 57 |
| AD-20449.1 | VEGFA | CCAAGGCCAGCACAUAGGA | 16 | ccAAGGccAGcAcAuAGGATsT CUCCuAUGUGCUGGCCUUGTsT | 58 59 |
| AD-20450.1 | VEGFA | AAGGCCAGCACAUAGGAGA | 17 | AAGGccAGcAcAuAGGAGATsT | 60 61 |
| AD-20451.1 | VEGFA | AGGCCAGCACAUAGGAGAG | 18 | AGGccAGcAcAuAGGAGAGTsT CUCUCCuAUGUGCUGGCCUTsT | 62 63 |
| AD-20452.1 | VEGFA | GGCCAGCACAUAGGAGAGA | 19 | GGccAGcAcAuAGGAGAGATsT UCUCCuAUGUGCUGGCCTsT | 64 65 |
| AD-20453.1 | VEGFA | GCCAGCACAUAGGAGAGAU | 20 | GccAGcAcAuAGGAGAGAuTsT AUCUCUCCuAUGUGCUGGCTsT | 66 67 |
| AD-20454.1 | VEGFA | CCAGCACAUAGGAGAGAUG | 21 | ccAGcAcAuAGGAGAGAuGTsT cAUCUCUCCuAUGUGCUGGTsT | 68 69 |
| AD-20455.1 | VEGFA | CAGCACAUAGGAGAGAUGA | 22 | cAGcAcAuAGGAGAGAuGATsT UcAUGUCUGGuAUGUGGUGTsT | 70 71 |
| AD-20456.1 | VEGFA | AGCACAUAGGAGAGAUGAG | 23 | AGcAcAuAGGAGAGAuGAGTsT CUcAUCUCUCCuAUGUGCUTsT | 72 73 |
| AD-20457.1 | VEGFA | CACAUAGGAGAGAUGAGCU | 24 | cAcAuAGGAGAGAuGAGcuTsT AGCUcAUCUCUCCuAUGUGTsT | 74 75 |
| AD-20458.1 | VEGFA | ACAUAGGAGAGAUGAGCUU | 25 | AcAuAGGAGAGAuGAGcuuTsT AAGCUcAUCUCUCCuAUGUTsT | 76 77 |
| AD-20459.1 | VEGFA | CAUAGGAGAGAUGAGCUUC | 26 | cAuAGGAGAGAuGAGcuucTsT GAAGGUcAUCUCUCCuAUGTsT | 78 79 |
| AD-20460.1 | VEGFA | AUAGGAGAGAUGAGCUUCC | 27 | AuAGGAGAGAuGAGcuuccTsT GGAAGCUcAUCUCUCCuAUTsT | 80 81 |
| AD-20461.1 | VEGFA | UAGGAGAGAUGAGCUUCCU | 28 | uAGGAGAGAuGAGcuuccuTsT AGGAAGCUcAUCUCUCCuATsT | 82 83 |
| AD-20462.1 | VEGFA | AGGAGAGAUGAGCUUCCUA | 29 | AGGAGAGAuGAGcuuccuATsT uAGGAAGCUcAUCUCUCCUTsT | 84 85 |
| AD-20463.1 | VEGFA | GGAGAGAUGAGCUUCCUAC | 30 | GGAGAGAuGAGcuuccuAcTsT GuAGGAAGCUcAUCUCUCCTsT | 86 87 |
| AD-20464.1 | VEGFA | GAGAGAUGAGCUUCCUACA | 31 | GAGAGAuGAGcuuccuAcATsT UGuAGGAAGCUcAUCUCUCTsT | 88 89 |
| AD-20465.1 | VEGFA | AGAGAUGAGCUUCCUACAG | 32 | AGAGAuGAGcuuccuAcAGTsT CUGuAGGAAGCUcAUCUCUTsT | 90 91 |
| AD-20466.1 | VEGFA | GAGAUGAGCUUCCUACAGC | 33 | GAGAuGAGcuuccuAcAGcTsT GCUGuAGGAAGCUcAUCUCTsT | 92 93 |
| AD-20467.1 | KSP | AUGUUCCUUAUCGAGAAUC | 34 | AuGuuccuuAucGAGAAucTsT GAUUCUCGAuAAGGAAcAUTsT | 94 95 |
| AD-20468.1 | KSP | UGUUCCUUAUCGAGAAUCU | 35 | uGuuccuuAucGAGAAucuTsT AGAUUCUCGAuAAGGAAcATsT | 96 97 |
| AD-20469.1 | KSP | GUUCCUUAUCGAGAAUCUA | 36 | GuuccuuAucGAGAAucuATsT uAGAUUCUCGAuAAGGAACTsT | 98 99 |
| AD-20470.1 | KSP | UUCCUUAUCGAGAAUCUAA | 37 | uuccuuAucGAGAAucuAATsT UuAGAUUCUCGAuAAGGAATsT | 100 101 |
| AD-20471.1 | KSP | UCCUUAUCGAGAAUCUAAA | 38 | uccuuAucGAGAAucuAAATsT UUuAGAUUCUCGAuAAGGATsT | 102 103 |

TABLE 13-continued

Sequences of dsRNA targeted to VEGF and Eg5/KSP (tiling)

| Duplex ID | target gene | target sequence 5' to 3' | SEQ ID NO: | Sense Strand Antisense strand 5' to 3' | SEQ ID NO: |
|---|---|---|---|---|---|
| AD-20472.1 | KSP | CCUUAUCGAGAAUCUAAAC | 39 | ccuuAucGAGAAucuAAAcTsT GUUuAGAUUCUCGAuAAGGTsT | 104 105 |
| AD-20473.1 | KSP | CUUAUCGAGAAUCUAAACU | 40 | cuuAucGAGAAucuAAAcuTsT AGUUuAGAUUCUCGAuAAGTsT | 106 107 |
| AD-20474.1 | KSP | UUAUCGAGAAUCUAAACUA | 41 | uuAucGAGAAucuAAAcuATsT uAGUUuAGAUUCUCGAuAATsT | 108 109 |
| AD-20475.1 | KSP | UAUCGAGAAUCUAAACUAA | 42 | uAucGAGAAucuAAAcuAATsT UuAGUUuAGAUUCUCGAuATsT | 110 111 |
| AD-20476.1 | KSP | AUCGAGAAUCUAAACUAAC | 43 | AucGAGAAucuAAAcuAAcTsT GUuAGUUuAGAUUCUCGAUTsT | 112 113 |
| AD-20477.1 | KSP | CGAGAAUCUAAACUAACUA | 44 | cGAGAAucuAAAcuAAcuATsT uAGUuAGUUuAGAUUCUCGTsT | 114 115 |
| AD-20478.1 | KSP | GAGAAUCUAAACUAACUAG | 45 | GAGAAucuAAAcuAAcuAGTsT CuAGUuAGUUuAGAUUCUCTsT | 116 117 |
| AD-20479.1 | KSP | AGAAUCUAAACUAACUAGA | 46 | AGAAucuAAAcuAAcuAGATsT | 118 119 |
| AD-20480.1 | KSP | GAAUCUAAACUAACUAGAA | 47 | GAAucuAAAcuAAcuAGAATsT UUCuAGUuAGUUuAGAUUCTsT | 120 121 |
| AD-20481.1 | KSP | AAUCUAAACUAACUAGAAU | 49 | AAucuAAAcuAAcuAGAAuTsT AUUCuAGUuAGUUuAGAUUTsT | 122 123 |
| AD-20482.1 | KSP | AUCUAAACUAACUAGAAUC | 49 | AucuAAAcuAAcuAGAAucTsT GAUUCuAGUuAGUUuAGAUTsT | 124 125 |
| AD-20483.1 | KSP | UCUAAACUAACUAGAAUCC | 50 | ucuAAAcuAAcuAGAAuccTsT GGAUUCuAGUuAGUUuAGATsT | 126 127 |
| AD-20484.1 | KSP | CUAAACUAACUAGAAUCCU | 51 | cuAAAcuAAcuAGAAuccuTsT AGGAUUCuAGUuAGUUuAGTsT | 128 129 |
| AD-20485.1 | KSP | UAAACUAACUAGAAUCCUC | 52 | uAAAcuAAcuAGAAuccucTsT GAGGAUUCuAGUuAGUUuATsT | 130 131 |
| AD-20486.1 | KSP | AAACUAACUAGAAUCCUCC | 53 | AAAcuAAcuAGAAuccuccTsT GGAGGAUUCuAGUuAGUUUTsT | 132 133 |

Example 13

VEGF Targeted dsRNA with a Single Blunt End

A set duplexes targeted to VEGF were designed and synthesized. The set included duplexes tiling 10 nucleotides in each direction of the target sites for AD-3133. Each duplex includes a 2 base overhang at the end corresponding to the 3' end of the antisense strand and no overhang, e.g., a blunt end, at the end corresponding to the 5' end of the antisense strand.

The sequences of each strand of these duplexes are shown in the following table.

Each duplex is assayed for inhibition of expression using the assays described herein. The VEGF duplexes are administered alone and/or in combination with an Eg5/KSP dsRNA (e.g., AD-12115). In some embodiments, the dsRNA are administered in a SNALP formulation as described herein.

TABLE 14

Target sequences of blunt ended dsRNA targeted to VEGF

| duplex ID | SEQ ID NO: | VEGF target sequence 5' to 3' | position on VEGF gene |
|---|---|---|---|
| AD-20447.1 | 134 | ACCAAGGCCAGCACAUAGG | 1365 |
| AD-20448.1 | 135 | CCAAGGCCAGCACAUAGGA | 1366 |
| AD-20449.1 | 136 | CAAGGCCAGCACAUAGGAG | 1367 |
| AD-20450.1 | 137 | AAGGCCAGCACAUAGGAGA | 1368 |
| AD-20451.1 | 138 | AGGCCAGCACAUAGGAGAG | 1369 |
| AD-20452.1 | 139 | GGCCAGCACAUAGGAGAGA | 1370 |
| AD-20453.1 | 140 | GCCAGCACAUAGGAGAGAU | 1371 |
| AD-20454.1 | 141 | CCAGCACAUAGGAGAGAUG | 1372 |
| AD-20455.1 | 142 | CAGCACAUAGGAGAGAUGA | 1373 |

TABLE 14-continued

Target sequences of blunt ended dsRNA targeted to VEGF

| duplex ID | SEQ ID NO: | VEGF target sequence 5' to 3' | position on VEGF gene |
|---|---|---|---|
| AD-20456.1 | 143 | AGCACAUAGGAGAGAUGAG | 1374 |
| AD-20457.1 | 144 | CACAUAGGAGAGAUGAGCU | 1376 |
| AD-20458.1 | 145 | ACAUAGGAGAGAUGAGCUU | 1377 |
| AD-20459.1 | 146 | CAUAGGAGAGAUGAGCUUC | 1378 |
| AD-20460.1 | 147 | AUAGGAGAGAUGAGCUUCC | 1379 |
| AD-20461.1 | 148 | UAGGAGAGAUGAGCUUCCU | 1380 |
| AD-20462.1 | 149 | AGGAGAGAUGAGCUUCCUA | 1381 |
| AD-20463.1 | 150 | GGAGAGAUGAGCUUCCUAC | 1382 |
| AD-20464.1 | 151 | GAGAGAUGAGCUUCCUACA | 1383 |
| AD-20465.1 | 152 | AGAGAUGAGCUUCCUACAG | 1384 |
| AD-20466.1 | 153 | GAGAUGAGCUUCCUACAGC | 1385 |

TABLE 15

Strand sequences of blunt ended dsRNA targeted to VEGF

| duplex ID | Sense strand (5' to 3') | SEQ ID NO: | Antisense strand (5' to 3') | SEQ ID NO: |
|---|---|---|---|---|
| AD-20447.1 | ACCAAGGCCAGCACAUAGGAG | 154 | CUCCUAUGUGCUGGCCUUGGUGA | 155 |
| AD-20448.1 | CCAAGGCCAGCACAUAGGAGA | 156 | UCUCCUAUGUGCUGGCCUUGGUG | 157 |
| AD-20449.1 | CAAGGCCAGCACAUAGGAGAG | 158 | CUCUCCUAUGUGCUGGCCUUGGU | 159 |
| AD-20450.1 | AAGGCCAGCACAUAGGAGAGA | 160 | UCUCUCCUAUGUGCUGGCCUUGG | 161 |
| AD-20451.1 | AGGCCAGCACAUAGGAGAGAU | 162 | AUCUCUCCUAUGUGCUGGCCUUG | 163 |
| AD-20452.1 | GGCCAGCACAUAGGAGAGAUG | 164 | CAUCUCUCCUAUGUGCUGGCCUU | 165 |
| AD-20453.1 | GCCAGCACAUAGGAGAGAUGA | 166 | UCAUCUCUCCUAUGUGCUGGCCU | 167 |
| AD-20454.1 | CCAGCACAUAGGAGAGAUGAG | 168 | CUCAUCUCUCCUAUGUGCUGGCC | 169 |
| AD-20455.1 | CAGCACAUAGGAGAGAUGAGC | 170 | GCUCAUCUCUCCUAUGUGCUGG | 171 |
| AD-20456.1 | AGCACAUAGGAGAGAUGAGCU | 172 | AGCUCAUCUCUCCUAUGUGCUGG | 173 |
| AD-20457.1 | CACAUAGGAGAGAUGAGCUUC | 174 | GAAGCUCAUCUCUCCUAUGUGCU | 175 |
| AD-20458.1 | ACAUAGGAGAGAUGAGCUUCC | 176 | GGAAGCUCAUCUCUCCUAUGUGC | 177 |
| AD-20459.1 | CAUAGGAGAGAUGAGCUUCCU | 178 | AGGAAGCUCAUCUCUCCUAUGUG | 179 |
| AD-20460.1 | AUAGGAGAGAUGAGCUUCCUA | 180 | UAGGAAGCUCAUCUCUCCUAUGU | 181 |
| AD-20461.1 | UAGGAGAGAUGAGCUUCCUAC | 182 | GUAGGAAGCUCAUCUCUCCUAUG | 183 |
| AD-20462.1 | AGGAGAGAUGAGCUUCCUACA | 184 | UGUAGGAAGCUCAUCUCUCCUAU | 185 |
| AD-20463.1 | GGAGAGAUGAGCUUCCUACAG | 186 | CUGUAGGAAGCUCAUCUCUCCUA | 187 |
| AD-20464.1 | GAGAGAUGAGCUUCCUACAGC | 188 | GCUGUAGGAAGCUCAUCUCUCCU | 189 |
| AD-20465.1 | AGAGAUGAGCUUCCUACAGCA | 190 | UGCUGUAGGAAGCUCAUCUCUCC | 191 |
| AD-20466.1 | GAGAUGAGCUUCCUACAGCAC | 192 | GUGCUGUAGGAAGCUCAUCUCUC | 193 |

Example 14

Inhibition of Eg5/KSP and VEGF Expression in Humans

A human subject is treated with a pharmaceutical composition, e.g., ALN-VSP02, having both a SNALP formulated dsRNA targeted to a Eg5/KSP gene and a SNALP formulated dsRNA targeted to a VEGF gene to inhibit expression of the Eg5/KSP and VEGF genes.

A subject in need of treatment is selected or identified. The subject can be in need of cancer treatment, e.g., liver cancer.

At time zero, a suitable first dose of the composition is subcutaneously administered to the subject. The composition is formulated as described herein. After a period of time, the subject's condition is evaluated, e.g., by measurement of tumor growth, measuring serum AFP levels, and the like. This measurement can be accompanied by a measurement of Eg5/KSP and/or VEGF expression in said subject, and/or the products of the successful siRNA-targeting of Eg5/KSP and/or VEGF mRNA. Other relevant criteria can also be measured. The number and strength of doses are adjusted according to the subject's needs.

After treatment, the subject's condition is compared to the condition existing prior to the treatment, or relative to the condition of a similarly afflicted but untreated subject.

Example 15

Clinical Trial of ALN-VSP02 in Humans

A clinical study is performed to assess the safety and tolerability of ALN-VSP02 in patients with advanced solid tumors with liver involvement, to characterize the PK (pharmacokinetics) of ALN-VSP02, and to assess preliminary evidence of antitumor/antiangiogenic activity of ALN-VSP02. The study is an open label, multi-center, with dose-escalation, utilizing up to ~55 patients with primary or secondary liver cancer.

ALN-VSP02 is administered by 15 minute IV infusion every 2 weeks at dose levels: 0.1, 0.2, 0.3, 0.4, 0.7, 1.0, 1.25, 1.5, 1.7, 2.0, 3.0, and 6.0 mg/kg.

Tumor measurements are performed after every 4 doses. Patients continue therapy until disease progression (as defined by RECIST criteria) or unacceptable toxicity is reached.

Example 16

Comparison of PK Data for ALN-12115 from Phase 1 Study: ALN-VSP02 in Humans

A clinical study was begun using the parameters described in Example 15. Three core biopsies were taken per time point from single tumor: pre-treatment and 2 and 7 days post-dose 1. Each biopsy was processed by 2 methods: 1: formalin-fixed, paraffin-embedded and 2, snap-frozen in liquid nitrogen. The PK of ALN-12115 was quantified in the tumors using qRT-PCR.

Allometric scalling and the predicted AUC (are under curve) of ALN-12115 (the KSP duplex in ALN-VSP02) are described as follows. Predicted $C_{max}$, and $AUC_{n-\infty}$ will have actual response ranging from 1.5 to 3.4 times of their predicted values; that is, the error in predicted dose will not be greater than ±)3- to 4-fold (Mordenti et al.).

|    | Unit   | Allometric Equation                | Prediction in an 85 kg Human |
|----|--------|------------------------------------|------------------------------|
| CL | mL/min | LogCL = 1.04 · LogBW + 0.01        | 103 (1.21 mL/min/kg)         |
| Vd | mL     | LogVd = 0.98 · LogBW + 1.98        | 7394 (86.99 mL/kg)           |

Predicted AUC=(D×F)/CL in human (F=1 for IV dosing)

| Phase 1 Infusion Dose | | Predicted Human Vd | Predicted Human CL | HED Exposure (AUC) |
|---|---|---|---|---|
| mg/kg | mg | mL | mL/min | ng * min/mL |
| 0.05 | 4.25 | 7394 | 103 | 41202 |
| 0.1  | 8.5  | 7394 | 103 | 82404 |
| 0.2  | 17   | 7394 | 103 | 164808 |
| 0.4  | 34   | 7394 | 103 | 329616 |
| 0.7  | 59.5 | 7394 | 103 | 576828 |

A comparison of PK data for ALN-12115 obtained from the phase 1 study is shown below. For Cohort 1, the predicted AUC was 41202 ng·min/mL while actual mean ranged 30784 to 37280 ng·min/mL. For cohort 2, the predicted AUC was 82404 ng·min/mL while actual mean ranged from 115469 to 130736 ng·min/mL. The AUC is within the predicted value of not greater than (±) 3 to 4 fold.

| | Cohort 1: 0.1 mg/kg | | | | | | |
|---|---|---|---|---|---|---|---|
| | C1W1 | | | | C2W2 | | |
| Parameter | 001-002 | 002-001 | 002-003 | Mean | 001-002 | 002-001 | Mean |
| Cmax (ng/mL) | 519 | 1167 | 583 | 756 | 673 | 1181 | 927 |
| $AUC_{0\text{-}last}$ (ng * min/mL) | 11407 | 53178 | 27766 | 30784 | 21198 | 53363 | 37280 |
| $AUC_{partial\ (0\text{-}135\ min)}$ (ng * min/mL) | 11407 | 42312 | 22596 | 25558 | 21198 | 45331 | 33265 |
| t½α (min) | 18.2 | 18.6 | 15.5 | 17.4 | 15.6 | 18.2 | 16.9 |

| | Cohort 2: 0.2 mg/kg | | | | | | | |
|---|---|---|---|---|---|---|---|---|
| | C1W1 | | | | C2W2 | | | |
| Parameter | 002-004 | 002-006 | 003-005 | Mean | 002-004 | 002-006 | 003-005 | Mean |
| Cmax (ng/mL) | 2266 | 2803 | 1723 | 2264 | 2684 | 2111 | 1921 | 2239 |
| $AUC_{0\text{-}last}$ (ng * min/mL) | 173850 | 134162 | 84197 | 130736 | 181038 | 110683 | 54686 | 115469 |
| $AUC_{partial\ (0\text{-}135\ min)}$ (ng * min/mL) | 113685 | 124975 | 81186 | 106615 | 127422 | 104407 | 52997 | 94942 |
| t½α (min) | 25.2 | 19.8 | 14.8 | 19.9 | 20.5 | 17.7 | 15.0 | 17.7 |

Abbreviations

CL—clearance—volume of plasma from which the drug is completely removed per unit time. The amount eliminated is proportional to the concentration of the drug in the blood.

Vd—Volume of distribution—amount of drug in the body divided by the concentration in the blood.

AUC—total area under the curve—is very useful for calculating the relative efficiency of different drug products $C_{max}$—highest concentration t½—half-life—time required for a given drug concentration to decrease by 50%. T½ is determined by the clearance and the volume of distribution.

C1W1—Cycle 1, week 1.

C2W2—Cycle 2, week 2.

Example 17

Treatment of Patients with Advanced Cancer with Liver Involvement Using ALN-VSP02

A clinical study was performed to assess the safety and tolerability of ALN-VSP02 in patients with advanced solid tumors with liver involvement, to characterize the PK (pharmacokinetics) of ALN-VSP02, and to assess preliminary evidence of antitumor/antiangiogenic activity of ALN-VSP02 at various dosage levels. The study focused on patients with primary or secondary liver cancer.

Patients having advanced cancer with liver involvement were given a 15 minute IV infusion of ALN-VSP02 every 2 weeks at the following dosage levels: 0.1, 0.2, 0.4, and 0.7 mg/kg. Treatments were given in cycles of 2 doses (1 month), with tumor measurements taken after every 2 cycles. Following administration of each dose, plasma samples were taken at defined time intervals and assayed for levels of ALN-VSP02 concentration to obtain pharmacokinetic information and to observe any evidence of drug accumulation.

$C_{max}$, $t_{max}$, and AUC of KSP siRNA in the patient's plasma for the first dose and the third dose are shown in Tables 16a and 16b respectively. $C_{max}$, $t_{max}$, and AUC for VEGF siRNA in the patient's plasma for the first dose and the third dose are shown in Tables 17a and 17b respectively. These tables show pharmacokinetic data from the first 3 patients enrolled onto each of the dose levels, i.e. N=3 for the first and third dose of ALN-VSP02. ALN-VSP02 treatment resulted in dose-proportional $C_{max}$ and AUC of ALN-VSP02 in human plasma with no evidence of drug accumulation between dose 1 and dose 3.

TABLE 16a

KSP siRNA mean plasma concentration parameter estimates by dose level

| | ALN-VSP Dose 1 (mg/kg) | | | |
|---|---|---|---|---|
| | 0.1 | 0.2 | 0.4 | 0.7 |
| $C_{max}$ (µg/mL) | 0.76 ± 0.36 | 2.3 ± 0.54 | 3.2 ± 1.2 | 9.8 ± 4.1 |
| $t_{max}$ (min) | 18.3 ± 5.8 | 16.7 ± 2.9 | 17 ± 3 | 20 ± 5 |
| $AUC_{0\text{-}last}$ (µg · min/mL) | 30.9 ± 21.1 | 130.7 ± 44.9 | 201.3 ± 38.6 | 501.2 ± 203.9 |

TABLE 16b

KSP siRNA mean plasma concentration parameter estimates by dose level and evidence of drug accumulation

| | ALN-VSP Dose 3 (mg/kg) | | | |
|---|---|---|---|---|
| | 0.1 | 0.2 | 0.4 | 0.7 |
| $C_{max}$ (µg/mL) | 0.93 | 2.2 ± 0.40 | 4.8 | 9.3 |
| $t_{max}$ (min) | 15 | 16.7 ± 2.9 | 18 | 15 |
| $AUC_{0\text{-}last}$ (µg · min/mL) | 37.3 | 130.7 ± 44.9 | 252.3 | 579.3 |

TABLE 17a

VEGF siRNA mean plasma concentration parameter estimates by dose level.

| | ALN-VSP Dose 1 (mg/kg) | | | |
|---|---|---|---|---|
| | 0.1 | 0.2 | 0.4 | 0.7 |
| $C_{max}$ (µg/mL) | 0.86 ± 0.43 | 2.5 ± 0.56 | 3.7 ± 1.2 | 9.7 ± 2.7 |
| $t_{max}$ (min) | 26.7 ± 5.8 | 21.7 ± 2.9 | 15 ± 0 | 18 ± 6 |
| $AUC_{0\text{-}last}$ (ug · min/mL) | 36.9 ± 20.2 | 140.3 ± 56.1 | 207.7 ± 36.3 | 610.9 ± 223.3 |

TABLE 17b

VEGF siRNA mean plasma concentration parameter estimates by dose level and evidence of drug accumulation

| | ALN-VSP Dose 3( mg/kg) | | | |
|---|---|---|---|---|
| | 0.1 | 0.2 | 0.4 | 0.7 |
| $C_{max}$ (µg/mL) | 0.98 | 2.2 ± 0.36 | 5 | 8.8 |
| $t_{max}$ (min) | 15 | 18.3 ± 2.9 | 18 | 20 |

TABLE 17b-continued

VEGF siRNA mean plasma concentration parameter estimates by dose level and evidence of drug accumulation

| | ALN-VSP Dose 3 (mg/kg) | | | |
|---|---|---|---|---|
| | 0.1 | 0.2 | 0.4 | 0.7 |
| $AUC_{0-last}$ (µg · min/mL) | 40.7 | 114.7 ± 62.9 | 330.9 | 622.4 |

DCE-MRI evaluation of one or more evaluable liver tumors was performed in patients at each dosage level. Measurements were obtained once before treatment (baseline), once on Day 3-5 post-dose, and once again on Day 8-10 post-dose. The average change in $K_{trans}$ from baseline was derived form the peak change in $K_{trans}$ for each evaluable tumor following the 2 post-treatment scans. The results are suggestive of an anti-VEGF effect in the majority of treated patients. Some patients also had an associated reduction in plasma VEGF levels.

In the majority of patients, only mild drug-related adverse effects were observed at 0.1 to 0.7 mg/kg dosages, indicating that ALN-VSP02 is generally well tolerated at the doses provided.

The ALN-VSP02 composition is effective for treatment of patients diagnosed with cancer with liver involvement and is well tolerated in patients at least up to dosages of 0.7 mg/kg. ALN-VSP-2 human plasma pharmacokinetics showed dos-proportional $C_{max}$ and AUC with no evidence of drug accumulation.

Those skilled in the art are familiar with methods and compositions in addition to those specifically set out in the present disclosure which will allow them to practice this invention to the full scope of the claims hereinafter appended.

We claim:

1. A method of treating a human having advanced cancer with liver involvement, comprising administering to the human 0.1, 0.2, 0.4, or 0.7 mg/kg ALN-VSP02 via 15 minute intravenous (IV) infusion once every 2 weeks for eight weeks, wherein the ALN-VSP02 provides a mean KSP siRNA $AUC_{0-last}$ from 10 to 800 µg*min/mL, a mean KSP siRNA $C_{max}$ from 0.4 to 13 µg/mL, a mean VEGF siRNA $AUC_{0-last}$ from 10 to 800 µg*min/mL and a mean VEGF siRNA $C_{max}$ from 0.4 to 13 µg/mL.

2. The method of claim 1, further comprising preadministration with at least one compound selected from the group consisting of dexamethasone, H1 and H2 blockers, and acetaminophen.

3. The method of claim 1, wherein the $AUC_{0-last}$ of f KSP siRNA is within about 80% to about 120% of a value selected, wherein said value is 30.9+/−21.1 µg*min/mL, 130.7+/−44.9 µg*min/mL, 201.3+/−38.6 µg*min/mL or 501.2+/−203.9 µg*min/mL.

4. The method claim 1 of, wherein the $AUC_{0-last}$ of f VEGF siRNA is within about 80% to about 120% of a value selected, wherein said value is 36.3+/−20.8 µg*min/mL, 140.3+/−56.1 µg*min/mL, 207.7+/−36.3 µg*min/mL or 610.9+/−223.3 µg*min/mL.

5. The method of claim 1, wherein the $C_{max}$ of KSP siRNA is within about 80% to about 120% of a value selected, wherein said value is 0.76+/−0.36 µg/mL, 2.3+/−0.54 µg/mL, 3.2+/−1.2 µg/mL and 9.8+/−4.1 µg/mL.

6. The method of claim 1, wherein the $C_{max}$ of VEGF siRNA is within about 80% to about 120% of a value selected, wherein said value is 0.86+/−0.43 µg/mL, 2.5+/−0.56 µg/mL, 3.7+/−1.2 µg/mL and 9.7+/−2.7 µg/mL.

7. The method of claim 1, wherein the composition has a dose-proportional maximum concentration ($C_{max}$) and area under curve (AUC) as measurable in the subject's plasma.

8. The method of claim 1, wherein the dose-proportional AUC of KSP siRNA is 10 to 800 µg*min/mL as measurable in the subject's plasma.

9. The method of claim 1, wherein the dose-proportional AUC of VEGF siRNA is 10 to 800 µg*min/mL as measurable in the subject's plasma.

10. The method of claim 1, wherein the dose-proportional $C_{max}$ of KSP siRNA is 0.4 to 13 µg/mL as measurable in the subject's plasma.

11. The method of claim 1, wherein the dose-proportional $C_{max}$ of VEGF siRNA is 0.4 to 13 µg/mL as measurable in the subject's plasma.

12. The method of claim 1, wherein the AUC value of KSP siRNA is within an error of ±3 to 4-fold of a predicted KSP siRNA AUC value.

13. The method of claim 1, wherein the AUC value of VEGF siRNA is within an error of ±3 to 4-fold of a predicted VEGF siRNA AUC value.

14. The method of claim 1, wherein the rate of clearance for the composition (CL) is 103 mL/min as measurable in the subject's plasma.

15. The method of claim 1, comprising administering to the human 0.1 mg/kg ALN-VSP02.

16. The method of claim 1, comprising administering to the human 0.2 mg/kg ALN-VSP02.

17. The method of claim 1, comprising administering to the human 0.4 mg/kg ALN-VSP02.

18. The method of claim 1, comprising administering to the human 0.7 mg/kg ALN-VSP02.

19. The method of claim 1, comprising administering to the human at least 0.4 mg/kg ALN-VSP02.

20. The method of claim 1, comprising administering to the human at least 0.7 mg/kg ALN-VSP02.

* * * * *